US00RE35279E

United States Patent [19]

Mochida et al.

[11] E Patent Number: Re. 35,279

[45] Reissued Date of Patent: Jun. 18, 1996

[54] HYDANTOIN DERIVATIVES

[75] Inventors: Ei Mochida, Toshima; Kimihiro Murakami, Suntou; Kazuo Kato, Mishima; Katsuaki Kato, Koganei; Jun Okuda; Ichitomo Miwa, both of Nagoya, all of Japan

[73] Assignee: Mochida Pharmaceutical Co., Ltd., Tokyo, Japan

[21] Appl. No.: 197,705

[22] Filed: Feb. 17, 1994

Related U.S. Patent Documents

Reissue of:

[64] Patent No.: 5,232,936
Issued: Aug. 3, 1993
Appl. No.: 644,632
Filed: Jan. 23, 1991

U.S. Applications:

[60] Division of Ser. No. 426,021, Oct. 24, 1989, Pat. No. 5,004,751, which is a continuation-in-part of Ser. No. 235, 557, Aug. 24, 1988, Pat. No. 4,914,099.

[30] Foreign Application Priority Data

Aug. 28, 1987 [JP] Japan ..... 62-214549
Feb. 25, 1989 [JP] Japan ..... 1-43422

[51] Int. Cl.[6] ..... A61K 31/44; C07D 211/06

[52] U.S. Cl. ..... 514/315; 514/365; 514/367; 514/373; 514/379; 514/390; 514/395; 514/418; 514/443; 514/445; 514/456; 514/473; 548/302.7; 548/307.1; 548/486; 548/189; 548/165; 548/209; 548/241; 548/256; 548/306.7; 548/309.7; 549/55; 549/65; 549/366; 549/466; 549/479

[58] Field of Search ..... 548/302.7, 307.1, 548/189, 311, 165, 209, 259, 486, 241; 549/55, 65, 366, 466, 479; 514/315, 365, 367, 373, 379, 390, 395, 418, 443, 445, 456, 473

[56] References Cited

U.S. PATENT DOCUMENTS

| | | | |
|---|---|---|---|
| 3,384,643 | 6/1958 | Sayigh | 260/309.7 |
| 3,534,022 | 10/1970 | Umemoto et al. | 260/239.9 |
| 4,056,622 | 11/1977 | Takayama et al. | 424/273 |
| 4,348,519 | 9/1982 | Pfister | 544/33 |
| 4,575,507 | 3/1986 | Lipinski | 514/278 |
| 4,656,169 | 4/1987 | Schnur | 514/235 |
| 4,743,611 | 5/1988 | Malamas et al. | 514/390 |
| 4,791,102 | 12/1988 | Bernat et al. | 514/19 |

FOREIGN PATENT DOCUMENTS

| | | |
|---|---|---|
| 0187387 | 7/1986 | European Pat. Off. . |
| 0251784 | 1/1988 | European Pat. Off. . |
| 0305947 | 3/1989 | European Pat. Off. . |
| 0355827 | 2/1990 | European Pat. Off. . |
| 6097 | 6/1968 | France . |
| 2308626 | 11/1976 | France . |

OTHER PUBLICATIONS

Saito et al., "Synthesis and Antiinflammatory Activity of Pyrido[4,3–e]–1,2–thiazine–3–carboxamide Derivatives", *Yakugaku Zasshi* 106, (1986), pp. 1008–1016.

Zawisza et al., "Synthesis and Properties of 2H–4–Hydroxy–2,5,7–trimethylpyrido[3,2–e]–1,2–thiazine–1,1–dioxide–3–carboxamides", *Il Farmaco Ed. Sci.*, 41, (1986), pp. 892–898.

Zawisza et al., "Synthesis and Properties of Some Derivatives of 2H–4,6–Dimethylpyrido[3,2–d] Isothiazoline–3–one–1,1–dioxide", *Il Farmaco Ed. Sci.*, 41, (1986), pp. 676–883.

Bellemin et al., "Synthesis of Some Pyrazolo[4,3–e][1,2] –and Thiazolo[4,5–e][1,2]thiazine 1,1–Dioxide Derivatives", *J. Heterocyclic Chem.*, 21, 1017 (1984), pp. 1017–1021.

El–Naggar et al, "Snythesis of Some Biologically Active Substituted Thiazole and Thiazoline–Amino Acid Derivatives", *Int. J. Peptide Protein Res.*, 19, 1982, pp. 408–412.

Miwa et al., "Improvement of Nerve Conduction Velocity in Mutant Diabetic Mice", *Chem. Pharm. Bull.*, vol. 37, No. 6, pp. 1581–1582, 1989.

Miwa et al., "Hypoglycemic Activity of Aldose Reductase Inhibitor", *Chem. Pharm. Bull.*, vol. 32, No. 5, pp. 2030–2032, 1984.

Okuda, "Aldose Reductase Inhibitor", Patent Abstracts of Japan, vol. 7, No. 209 (C–186), 1983. JP–58–109418.

Okuda, "Hydantoin Derivative and Aldose Reductase Inhibitor", Patent Abstracts of Japan, vol. 12, No. 56 (C–477), 1988. JP 62–201873.

Okuda, "Hydantoin Derivative and Aldose Reductase Inhibitor", Patent Abstracts of Japan, vol. 11, No. 267 (C–443), 1987. JP 62–67075.

Chemical Abstracts, vol. 106, 1987, Abstract No. 4857q.

Chemical Abstracts, vol. 102, 1985, Abstract No. 6355r.

Chemical Abstracts, vol. 101, 1984, Abstract No. 38464w.

Chemical Abstracts, vol. 101, 1984, Abstract No. 23906t.

Chemical Abstracts, vol. 97, 1982, Abstract No. 128022d.

Chemical Abstracts, vol. 95, 1981, Abstract No. 168034z.

(List continued on next page.)

*Primary Examiner*—Joseph K. McKane
*Attorney, Agent, or Firm*—Oliff & Berridge

[57] ABSTRACT

The present invention relates to novel hydantoin derivatives, processes for producing said hydantoin derivatives, pharmaceutical compositions containing at least one of said hydantoin derivatives as aldose reductase inhibitors and novel intermediate compounds in the synthesis of said hydantoin derivatives.

The present invention is based on the selection of a hydantoin which is bonded by a sulfonyl group to various substituents at the 1-position of the hydantoin skeleton.

The compounds of the present invention have a strong inhibitory activity against aldose reductase. These compounds are extremely useful for the treatment and/or prevention of various forms of diabetic complications based on the accumulation of polyol metabolites.

15 Claims, No Drawings

OTHER PUBLICATIONS

Chemical Abstracts, vol. 94, 1981, Abstract No. 208890p.
Chemical Abstracts, vol. 109, 1988, Abstract No. 38244q.
Chemical Abstracts, vol. 107, 1987, Abstract No. 77727c.
Chemical Abstracts, vol. 107, 1987, Abstract No. 58954h.
Chemical Abstracts, vol. 107, 1987, Abstract No. 7583d.
Chemical Abstracts, vol. 106, 1987, Abstract No. 156380s.
Chemical Abstracts, vol. 106, 1987, Abstract No. 156145u.
Chemical Abstracts, vol. 106, 1987, Abstract No. 119683x.
Chemical Abstracts, vol. 90, 1979, Abstract No. 121208r.
Chemical Abstracts, vol. 87, 1977, Abstract No. 167930m.
Chemical Abstracts, vol. 85, 1976, Abstract No. 63077f.
Chemical Abstracts, vol. 91, 1979, Abstract No. 5233s.
Chemical Abstracts, vol. 87, 1977, Abstract No. 68159k.
Miwa et al., "In Vivo Activities of Aldose Reductase Inhibitors", *Biochemical Pharmacology,* vol. 40, No. 2, pp. 303–307, 1990.
Miwa et al., "Development of Potent Aldose Reductase Inhibitors", *Biochemical Pharmacology,* vol. 36, No. 17, pp. 2789–2794, 1987.

Chemical Abstracts, vol. 99, 1983, Abstract No. 116079f.

Chemical Abstracts, vol. 107, 1987, Abstract No. 59037y.

Chemical Abstracts, vol. 109, 1988, Abstract No. 129004c.

Chemical Abstracts, vol. 95, No. 15, 1981, Abstract No. 132725m.

Chemical Abstracts, vol. 97, No. 1, 1982, Abstract No. 6774e.

Chemical Abstracts, vol. 109, 1988, Abstract No. 211019y.

Chemical Abstracts, vol. 109, 1988, Abstract No. 190818n.

HYDANTOIN DERIVATIVES

Matter enclosed in heavy brackets [ ] appears in the original patent but forms no part of this reissue specification; matter printed in italics indicates the additions made by reissue.

This is a divisional application of U.S. Ser. No. 07/426,021 filed Oct. 24, 1989, now U.S. Pat. No. 5,004,751 which in turn was a continuation-in-part divisional application of U.S. Ser. No. 07/235,557, filed Aug. 24, 1988, now U.S. Pat. No. 4,914,099.

BACKGROUND OF THE INVENTION

The present invention relates to novel hydantoin derivatives, processes for producing hydantoin derivatives, pharmaceutical compositions containing at least one of said hydantoin derivatives as aldose reductase inhibitors and novel intermediate compounds in the synthesis of said hydantoin derivatives.

Cataract, peripheral neuropathy, retinopathy and nephropathy associated with diabetes mellitus result from abnormal accumulation of polyoi metabolites converted from sugars by aldose reductase. For example, sugar cataract results from damage of lens provoked by change in osmotic pressure induced by abnormal accumulation of polyol metabolites converted from glucose or galactose by aldose reductase in lens. [see J. H. Kinoshita et al., Biochim. Biophys. Acta, 158, 472 (1968) and cited references in the report]. And some reports were submitted about undesirable effect of abnormal accumulation of polyol metabolites in lens, peripheral nerve cord and kidney of the diabetic animals [see A. Pirie et al. Exp. Eye Res., 3, 124 (1964) L. T. Chylack Jr. et at., Invest. Opthal., 8,401 (1969) J. D. Ward el al, Diabetologia, 6, 531 (1970)]. Consequently, it is important to inhibit aldose reductase as strongly as possible for treating and/or preventing diabetic complications mentioned above. Although several compounds have been offered as aldose reductase inhibitors, none of them is fully sufficient in inhibitory activity against the enzyme. Therefore, it has been desired to develop new compounds having a stronger inhibitory activity against aldose reduetase.

SUMMARY OF THE INVENTION

An object of the present invention is to provide novel hydantoin derivatives and salts, solvates and solvates of salts thereof.

Another object of the present invention is to provide processes for producing said novel hydantoin derivatives.

A further object of the present invention is to provide pharmaceutical compositions comprising at least one of said novel hydantoin derivatives having an inhibitory activity against aldose reductase.

A further object of the present invention is to provide novel intermediate compounds in the synthesis of said novel hydantoin derivatives.

The present inventors previously found that substituted phenylsulfonylhydantoin derivatives and naphthalenylsulfonylhydantoin derivatives had a strong inhibitory activity against aldose reductase and accomplished an invention on aldore reductase inhibitors. (JP-A-56 213518, 60 207113, 61 43770)

The present inventors previously found that sulfonylhydantoin derivatives had a strong inhibitory activity against aidose reductase and accomplished an invention on aldose reductase inhibitors (JP kokai 58 109418, 62 67075, 62 201873 and 1 61465). And M. S. Malamas et al. U.S. Pat. No. 4,743,611 disclosed naphthalenesulfonyl hydantoin derivatives useful as aldose reductase inhibitors. And Ohishi et al. disclosed benzofuranylsulfonyl glycine derivatives useful as drugs of treatment of diabetic complications (JP Kokai 62 155269).

Furthermore, the present inventors have made extensive researches on a series of compounds having an inhibitory activity against aldose reductase and found novel hydantoin derivatives having an extremely strong inhibitory activity against aldose reductase. They are extremely usful for the treatment and/or prevention of various forms of diabetic complications based on the accumulation of polyol metabolites.

DETAILED DESCRIPTION OF THE INVENTION

As a result of extensive investigations concerning development of hydantoin derivatives having a satisfactory inhibitory activity against aldose reductase, the present inventors have found that novel hydantoin derivatives represented by the general formula (I) satisfy this requirement and have accomplished the present invention.

The present invention is based on the selection of a hydantoin which is bonded by or through a sulfonyl group to various substituents at the 1-position of the hydantoin skeleton.

The present invention is directed to novel hydantoin derivatives represented by the general formula (I):

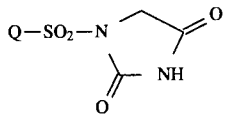

(I)

and non-toxic salts, solvates and solvates of non-toxic salts thereof; wherein Q represents an alkyl group having 1 to 8 carbon atoms, a cycloalkyl group having 3 to 6 carbon atoms, a biphenylyl group, a mono- or a fused heterocyclic group which may be substituted by one or more substituents which are same or different and selected from a group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group, an optionally protected amino group, a carbamoyi group and a phenyl group or a group:

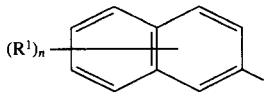

wherein $R^1$ represents an andno group which may be substituted with lower alkyl groups and/or acyl groups, a halogen atom, a lower alkyl group, an alkoxy group, a nitro group or a cyano group, or combination of any of these groups when n represents an integer of 2 or more, and n represents an integer of 1, 2, 3 or 4.

The present invention is also directed to the process for preparing above-mentioned hydantoin derivatives.

The present invention is further directed to pharmaceutical compositions characterized by containing at least one of these hydantoin derivatives as active component(s).

The present invention is further directed to novel intermediate compounds in the synthesis of above-mentioned hydantoin derivatives.

Compounds of the present invention and non-toxic salts, solvates and solvates or non-toxic salts thereof represents a satisfactory inhibitory activity against aldose reductase and a preventing activity against cataracts, neuropathy in experimental animal models.

Compounds of the present invention and non-toxic salts, solvates and non-toxic salts thereof are free of central nervous system side effects such as anti-convulsant activity and low toxicity, so useful for the treatment and/or prevention of various forms of diabetic complications such as neuropathy, autonomic disease, cataract, retinopathy, neuropathy and microvascular disease.

In the hydantoin derivatives of the present invention represented by the general formula (I), it is known that the hydantoin moiety exhibits tautomerism as shown below:

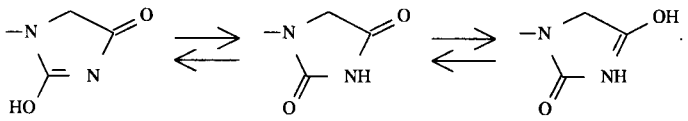

Since these tautomeric isomers are generally deemed to be the same substance, the compounds of the present invention represented by the general formula (I) also include all of these tautomeric isomers.

The compounds represented by the general formula (I) may form salts with base. Typical examples of salts with base of the compounds represented by the general formula (I) include pharmaceutically acceptable salts such as alkali metal salts (such as sodium salts, potassium salts, etc.), alkaline earth metal salts (such as magnesium salts, calcium salts, etc.), salts with organic bases (such as ammonium salts, benzylamine salts, diethylamine salts, etc.) or salts of amino acids (such as arginine salts, lysine salts, etc.). These salts of the compounds represented by the general formula (I) may be mono-salts or di-salts which may be salts of the hydantoin moiety and/or salts of the carboxy group contained in the Q group.

The compounds represented by the general formula (I) may also form acid addition salts. Typical example of acid addition salts of the compounds represented by the general formula I) include pharmaceutically acceptable salts, such as salts of inorganic acids (such as hydrochlorides, hydrobromides, sulfates, phosphates, etc.), salts of organic acids (such as acetates, citrates, maleates, tartrates, benzoates, ascorbate, ethanesulfonates, toluene-sulfonates, etc.) or salts of amino acids (such as aspartates, glutamates, etc.). These salts of the compounds represented by the general formula (I) may be salts of the heterocyclic moiety in the Q group.

In the compounds of the present invention represented by the general formula (I), the lower alkyl group can be defined more specifically as a straight or branched lower alkyl group having 1 to 4 carbon atoms such as methyl, ethyl, isopropyl, tert-butyl, etc. The alkoxy group can be defined more specifically as a straight branched lower alkoxy group having 1 to 4 carbon atoms such as methoxy, ethoxy, tert-butoxy, etc. The acyl group can be defined more specifically as a straight or branched lower acyl group having 1 to 5 carbon atoms such as formyl, acetyl, propanoyl, butanoyl, pivaloyl, etc.

In the compounds of the present invention represented by the general formula (I), the heterocyclic group can be defined as a monocyclic heterocyclic group such as pyrrolyl, pyrrolinyl, imidazolyl, pyrazolyl, triazolyl, tetrazolyl, oxazolyl, isoxazolyl, oxadiazolyl, thiazolyl, isothiazolyl, thiazolinyl, thiadiazolyl, thiatriazolyl, thienyl (thiophenyl), furyl, pyrrolidinyl, imidazolidinyl, thiazolidinyl, pyridyl or its N-oxide, pyrazinyl, pynmidinyl, pyridazinyl, piperidyl, piperazinyl, morpholinyl, triazinyl, etc., or a fused heterocyclic group such as indolyl, isoindolyl, benzimidazolyl, quinolyl, isoquinolyl, quinazolinyl, cinnolinyl, phthalazinyl, quinoxalinyl, indazolyl, benzotriazolyl, benzoxazolyl, benzoxadiazolyl, benzothiazolyl, benzothiadiazolyl, benzisoxazolyl, benzisothiazolyl, benzothiophenyl (benzo[b]thiophenyl or benzo[c]thiophenyl)-(benzothienyl (benzo[b]thienyl or benzo[c]thienyl)), tetrahydrobenzothiophenyl (tetrahydrobenzothienyl), benzofuranyl (benzo[b]furanyl or isobenzofuranyl), chromenyl, chromanyl, coumarinyl, chromonyl, triazolopyridyl, tetrazolopyridyl, purinyl, thiazolopyrimidinyl, triazolopyrimidinyl, thiadiazolopyrmidinyl, thiazolopyridazinyl, naphthyridinyl, xanthenyl, phenoxathiinyl, phenoxazinyl, phenothiazinyl, carbazolyl, etc. preferably indolyl, benzimidazolyl, benzotriazolyl, benzothiazolyl, benzisoxazolyl, benzisothiazolyl, benzothiophenyl, tetrahydrobenzothiophenyl, benzofuranyl, coumarinyl, chromonyl, more preferably benzo[b]thiophenyl or benzo[b]furanyl. The above-mentioned heterocyclic groups may be substituted with a group such as a lower alkyl group (such as methyl, ethyl, isopropyl, tert-butyl, etc.), a lower alkylcarbonyl group (such as acetyl, propanoyl, butanoyl, etc.), a lower alkoxy group (such as methoxy, ethoxy, isopropoxy, tert-butoxy, etc.), a phenyl group, a cyano group, a carbamoyl group, an optionally protected carboxy group, an optionally protected carboxymethyl group, a nitro group, a halogenated lower alkyl group (such as trifluoromethyl, pentafluoroethyl, etc.), an optionally protected hydroxy group, an optionally protected amino group, (such as acyl amino, etc.), a lower alkylthio group, a lower alkylsulfinyl group, a lower alkyl sulfonyl group or a halogen atom (such as fluoro, chloro, bromo, iodo etc.), or combination of any of these groups.

In a mono- heterocyclic group, a compound unsubstituted or substituted with 1 or 2 substituents which are the same or different and selected from a group consisting of a halogen atom or phenyl group, is preferable.

In a fused heterocyclic group, a compound unsubstituted or substituted with 1 to 3 substituents which are the same or different and selected from a group consisting of a halogen atom, a lower alkyl group, a halogenated lower alkyl group, a lower alkylthio group or a cyano group, is preferable.

When a fused heterocyclic group is a benzo[b]furan-2-yl group which may be substituted, the said substituents are preferably 1 to 3 halogen atoms.

The compounds of the present invention represented by the formula (I) can be produced by the processes described as follows.

Namely,

The starting material of sulfonyl halide represented by the formula (II):

$$Q—SO_2—Y \qquad (II)$$

wherein Q has the same significance as defined above, and Y represents a halogen atom, is prepared as follows.

A compound Q—H wherein Q has the same significance as defined above and H represents a hydrogen atom is reacted with a base (such as n-butyllithium or lithium diisopropylamide, etc.) and sulfur dioxide and then reacted with a halogenating reagent (such as chlorine, bromine, phosphorus pentachloride, thionyl chloride, N-chlorosuccinimide or N-bromosuccinimide, etc.) to obtain an objective compound.

Further, Q—H wherein Q has the same significance as defined above is reacted with a halosulfonic acid (preferably chlorosulfonic acid, etc.) to obtain directly an objective compound.

Further, a sulfonic acid derivative of Q—H (Q—$SO_3H$) wherein Q has the same significance as defined above is reacted with sodium bicarbonate to give a corresponding salt, and then reacted with a halogenating reagent (such as phosphorus pentachloride, thionyl chloride or thionyl bromide, etc.) to obtain an objective compound.

Further, a S-benzyl derivative of Q—H (Q—S—$CH_2C_6H_5$) wherein Q has the same significance as defined above is reacted with a halogenating reagent (such as chlorine, etc.) to obtain an objective compound.

Further, an amine derivative of Q—H (Q—$NH_2$) wherein Q has the same significance as defined above is reacted whh a nitrite salt (such as sodium nitrite, etc.), and then reacted with sulfur dioxide and a halogcnating reagent (such as copper (I) chloride or copper (II) chloride, etc.) to obtain an objective compound.

The sulfonyl halide derivative, obtained above mentioned procedure is reacted with a glycine derivative represented by the formula (III):

$$NH_2CH_2CO—R \quad (III)$$

wherein R represents a hydroxy group, an alkoxy group or an amino group which may be substituted by an alkoxycarbonyl group, to give the corresponding sulfonylglycine derivative represented by the formula (IV):

$$Q—SO_2NHCH_2CO—R \quad (IV)$$

wherein Q and R have the same significance as defined above. Such a condensation reaction is carried out generally in an aqueous solution, in an organic solvent (such as dichloromethane, chloroform, dioxane, tetrahydrofuran, acetonitrile, ethyl acetate, acetone, N,N-dimethylformamide, etc.) or in a mixed solvent of an aqueous solution and an organic solvent, preferably in the presence of deacidifying agent. As the deacidifying agent, triethylamine, diethylaniline, pyridine, etc. is employed in the organic solvent system, and in the aqueous system, aqueous alkali (such as sodium carbonate, sodium bicarbonate, potassium carbonate, sodium hydroxide, etc.) is employed. The condensation reaction is carried out at temperatures ranging from about −20° to 80° C., preferably 0° C. to room temperature.

When R represents an amino group in the formula (IV), the sulfonylglycine derivative is represented by the formula (V):

$$Q—SO_2NHCH_2CONH_2 \quad (V)$$

wherein Q has the same significance as defined above.

The sulfonylglycine derivative represented by the formula (V) is cyclized using a haloformic acid ester (such as methyl chloroformate, ethyl chloroformate, etc.) in the presence of a base (such as sodium hydride, potassium hydride, butyllithium, etc.) to give the corresponding hydantoin derivative of the present invention represented by the formula (I). The cyclization reaction is carried out generally in an inert solvent (such as N,N-dimethylformamide, dimethylsulfoxide, ethyl ether, tetrahydrofuran, dioxane, dichloromethane, etc.) and at temperatures ranging from about −20° to 120° C., preferably 0° to 80° C.

When R represents an amino group protected with an alkoxycarbonyl group, the sulfonylglycine derivative is cyclized in the presence of a base (such as sodium hydride etc.) to give the corresponding hydantoin derivative of the present invention represented by the formula (I).

When R represents a hydroxy group or an alkoxy group in the formula (IV), the sulfonylglycine derivative is represented by the formula (VI):

$$Q—SO_2NHCH_2CO—R^1 \quad (VI)$$

wherein Q has the same significance as defined above and $R^1$ represents a hydroxy group or an alkoxy group. The sulfonylglycine derivative represented by the formula (VI) is cyclized with a thiocyanate derivative (such as ammonium thiocyanate, potassium thiocyanate, etc.) in the presence of an acid anhydride (such as acetic anhydride, propionic anhydride. etc.) and. if necessary and desired, a base (such as pyridine, triethylamine, etc.) to give the corresponding 2-thiohydantoin derivative. If necessary and desired, the cyclization reaction is carried out after hydrolysis of ester when $R^1$ represents an alkoxy group. The cyclization reaction is carried out generally in an inert solvent (such as pyridine, triethylamine, N,N-dimethylformamide, dimethylsulfoxide, etc.) and at temperatures ranging from 0° to 120° C., preferably room temperature to 100° C. Further, the 2-thiohydantoin derivative obtained by said cyclization is oxidized using oxidizing agent (such as nitric acid, chlorine, iodine chloride, potassium permanganate, hydrogen peroxide, dimethylsulfoxide-sulfuric acid, etc.) to give the corresponding hydantoin derivatives of the present invention represented by the formula (I).

To demonstrate the utility of the compounds of the present invention, experimental examples of representative compounds are shown below.

Compounds in the present invention

Compound 1: 1-(1-chloronaphthalen-2-ylsulfonyl)-hydantoin

Compound 2: 1-(3-chloronaphthalen-2-ylsulfonyl)-hydantoin

Compound 3: 1-(5-chloronaphthalen-2-ylsulfonyl)-hydantoin

Compound 4: 1-(6-chloronaphthalen-2-ylsulfonyl)-hydantoin

Compound 5: 1-(7-chloronaphthalen-2-ylsulfonyl)-hydantoin

Compound 6: 1-(8-chloronaphthalen-2-ylsulfonyl)-hydantoin

Compound 7: 1-(3,6-dichloronaphthalen-2-ylsulfonyl)-hydantoin

Compound 8: 1-(1-bromonaphthalen-2-ylsulfonyl)-hydantoin

Compound 9: 1-(3-bromonaphthalen-2-ylsulfonyl)-hydantoin

Compound 10: 1-(6-bromonaphthalen-2-ylsulfonyl)-hydantoin

Compound 11: 1-(5-nitronaphthalen-2-ylsulfonyl)-hydantoin

Compound 12: 1-(3-methylnaphthalen-2-ylsulfonyl)-hydantoin

Compound 13: 1-(6-methyl-5-nitronaphthalen-2-ylsulfonyl) hydantoin

Compound 14: 1-(7-methylnaphthalen-2-ylsulfonyl)-hydantoin

Compound 15: 1-(6-methoxy-5-nitronaphthalen-2-ylsulfonyl)hydantoin

Compound 16: 1-(benzo[b]thiophen-2-ylsulfonyl)-hydantoin

Compound 17: 1-(3-chlorobenzo[b]thiophen-2-ylsulfonyl) hydantoin

Compound 18: 1-(5-chlorobenzo[b]thiophen-2-ylsulfonyl) hydantoin

Compound 19: 1-(benzo[b]furan-2-ylsulfonyl)hydantoin

Compound 20: 1-(5-chlorobenzo[b]furan-2-ylsulfonyl)-hydantoin

Compound 21: 1-(5-bromobenzo[b]furan-2-ylsulfonyl)-hydantoin

Compound 22: 1-(benzothiazol-2-ylsulfonyl)hydantoin

Compound 23: 1-(coumarin-6-ylsulfonyl)hydantoin

Compound 24: 1-(2,5-dichlorothiophen-3-ylsulfonyl)-hydantoin

Compound 25: 1-(4,5-dibromothiophen-2-ylsulfonyl)-hydantoin

Compound 26: 1-(6-chlorobenzo[b]thiophen-2-ylsulfonyl) hydantoin

Compound 27: 1-(7-chlorobenzo[b]thiophen-2-ylsulfonyl) hydantoin

Compound 28: 1-(3-isopropylbenzo[b]thiophen-2-ylsulfonyl)hydantoin

Compound 29: 1-(3-trifluoromethylbenzo[b]thiophen-2-ylsulfonyl)hydantoin

Compound 30: 1-(3-bromobenzo[b]thiophen-2-ylsulfonyl) hydantoin

Compound 31: 1-(3-methoxybenzo[b]thiophen-2-ylsulfonyl)hydantoin

Compound 32: 1-(3-methylsulfonylbenzo[b]thiophen-2-ylsulfonyl)hydantoin

Compound 33: 1-(3-cyanobenzo[b]thiophen-2-ylsulfonyl) hydantoin

Compound 34: 1-(3-bromo-7-fluorobenzo[b]thiophen-2-ylsulfonyl)hydantoin

Compound 35: 1-(2-chlorobenzo[b]thiophen-3-ylsulfonyl) hydantoin

Compound 36: 1-(4-iodobenzo[b]furan-2-ylsulfonyl)hydantoin

Compound 37: 1-(4,6-dichlorobenzo[b]furan-2-ylsulfonyl) hydantoin

Compound 38: 1-(3-bromobenzo[b]furan-2-ylsulfonyl)hydantoin

Compound 39: 1-(5-fluorobenzo[b]thiophen-2-ylsulfonyl) hydantoin

Compound 40: 1-(4-chlorobenzo[b]thiophen-2-ylsulfonyl) hydantoin

Compound 41: 1-(benzo[b]isothiazol-3-ylsulfonyl)hydantoin

Compound 42: 1-(5-nitrobenzo[b]thiophen-2-ylsulfonyl)hydantoin

Compound 43: 1-(5-carboxybenzo[b]thiophen-2-ylsulfonyl) hydantoin

Compound 44: 1-(4,5-dichlorobenzo[b]furan-2-ylsulfonyl) hydantoin

Compound 45: 1-(5,6-dichlorobenzo[b]furan-2-ylsulfonyl) hydantoin

Compound 46: 1-(3-bromo-4,6-dichlorobertzo[b]furan-2-ylsulfonyl)hydantoin

Compound 47: 1-(3-chlorobenzo[b]furan-2-ylsulfonyl)hydantoin

Compound 48: 1-(7-fluorobenzo[b]furan-2-ylsulfonyl)hydantoin

Compound 49: 1-(3-bromo-7-fluorobenzo[b]furan-2-ylsulfonyl)hydantoin

REFERENCE COMPOUNDS

Compound A: 1-(naphthalene-2-ylsulfonyl)hydantoin

Compound B: sorbinil: [(S)-6-Fluoro-2,3-dihydrospiro(4H-1-benzopyran4,4'-imidazolidine)-2', 5'-dione] (synthesized by the method of R. S. sarges et al.: see J. Med. Chem., 28, 1716 (1985))

EXPERIMENTAL EXAMPLE 1

The inhibitory activities of hydantoin derivatives on rat lens aldose reductase were measured according to the procedure of Inagaki et al. CK. Inagaki et al., Arch. Biochem. Biophys., 216, 337 (1982)) with slight modifications. Assays were performed in 0.1 M phosphate buffer (pH 6.2) containing 0.4 M ammonium sulfate, 10 mM DL-glyceraldehyde, 0.16 mM nicotinamide adenine dinucleotide phosphate, reduced form (NADPH) and aldose reductase (0.010–0.016 units) in a total volume of 1.0 mi. To this mixture was added 10 μl of the solution of each hydantoin derivative to be tested, and the decrease in absorbance at 340 nm was measured with a spectrophotometer.

The concentrations of typical hydantoin derivatives of the present invention required to produce 50% inhibition are shown in table 1.

TABLE 1

| Compounds | $IC_{50}$ (μmol/l) |
|---|---|
| 1 | 0.29 |
| 2 | 0.16 |
| 3 | 0.19 |
| 4 | 0.14 |
| 5 | 0.39 |
| 6 | 0.46 |
| 7 | 0.24 |
| 8 | 0.094 |
| 9 | 0.35 |
| 10 | 0.17 |
| 11 | 0.10 |
| 12 | 0.14 |
| 13 | 0.027 |
| 14 | 0.35 |
| 15 | 0.038 |
| A | 0.66 |

Compounds 1 to 15 of the present invention showed stronger inhibitory activities against aldose reductase than reference compound A did. Above all, compound 13 and 15 were ten times or more potent than reference compound A.

EXPERIMENTAL EXAMPLE 2

The inhibitory activities of hydantoin derivatives on bovine lens aldose reductase were measured according to the procedure of Inagaki et al. (K. Inagaki et al., Arch. Blochcm. Biophys., 216, 337 (1982)) with slight modifications. Assay procedure was the same as described in Experimental example 1 except that bovine lens aldose reductsse preparation was used instead of rat lens aldose reductase preparation.

The concentrations of the typical hydantoin derivatives of the present invention required to produce 50% inhibition are shown in table 2.

TABLE 2

| Compounds | $IC_{50}$ (μmol/l) |
|---|---|
| 13 | 0.10 |
| 15 | 0.23 |
| 16 | 0.39 |
| 17 | 0.12 |
| 18 | 0.24 |
| 20 | 0.36 |
| 21 | 0.30 |
| 22 | 0.34 |
| 23 | 0.22 |
| 24 | 0.29 |
| 25 | 0.26 |
| 26 | 0.27 |
| 27 | 0.19 |
| 28 | 0.14 |
| 29 | 0.13 |
| 30 | 0.12 |
| 31 | 0.27 |
| 32 | 0.38 |
| 33 | 0.19 |
| 34 | 0.085 |
| 35 | 0.30 |
| 36 | 0.24 |
| 37 | 0.17 |
| 38 | 0.16 |
| 39 | 0.32 |
| 40 | 0.17 |
| 41 | 0.47 |
| 42 | 0.27 |
| 43 | 0.40 |
| 44 | 0.061 |
| 45 | 0.083 |
| 46 | 0.054 |
| B | 0.65 |

Compounds 13, 15, 16 to 18, 20 to 46 of the present invention showed stronger inhibitory activities against aldose reductase than reference compound B did, which is a well known potent aldose reductase inhibitor. Compound 17, 18, 23 and 24 were as potent as compound 13 and 15, which showed strongest inhibitory activities in experimental example 1. Above all, several compounds were ten times or more potent than reference compound B.

EXPERIMENTAL EXAMPLE 3

Hydantom derivatives of the present invention were examined for acute toxicity. Groups of 5 ICR strain mice were orally administered with compound 7, 13 to 17, 19, 20, 21, 24, 38, 40, 44, 45, 47 to 49 of the present invention in a dose of 1 g/kg, and no change was observed in any of the groups over the one-week period after the administration.

Since the compounds of the present invention have strong inhibitory activities against aldose reductase, show lower toxicity and show stronger preventing activities against cataracts, neuropathy in animal models than known compounds, pharmaceutical compositions containing at least one of these compounds as active component(s) are useful for the treatment and/or prevention of diabetic complication based on the accumlation of polyol metabolites.

The hydantoin derivatives provided by the present invention can be employed as pharmaceutical compositions, for example, in the form of pharmaceutical compositions containing hydantoin derivatives together with appropriate pharmaceutically acceptable carrier or medium such as sterilized water, edible oils, non-toxic organic solvents or non-toxic solubilizer such as glycerin or propylene glycol. They may be mixed with excipients, binders, lubricants, coloring agents, corrigents, emulsifying agents or suspending agents such as Tween 80 or arabic gum to prepare tablets, capsules, powders, granules, subtilized granules, syrups, eye drops, suppositories, ointments, inhalants, aqueous or oily solutions or emulsion or suspensions for injections. These agents can be administered either orally or parenterally (such as intravenous administration, intramuscular administration, subcutaneous administration, intrarectal administration, percutaneous administration or permucosal administration etc.), and the amount of administration may be in the range of 1 to 3000 mg/day, preferably 10 to 500 rag/day when the preparation is tablets, capsules, powders, injections, suppositories, syrups, inharants or ointments, 1 μg to 10 mg/day, preferably 10 μmg to 1 mg/day when the preparation is eye drops, and 1 to 10% composition when the preparation is ointments, and may also be adjusted according to the patient conditions and can administered once or divided 2 to 6 times or by instillation, etc.

Hereafter the present invention will be described with references to the examples below but is not deemed to be limited thereof.

EXAMPLE 1

Preparation of 1-(1-chloronaphthalen-2-ylsulfonyl)hydantoin (compound I)

Step 1

Preparation of N-(1-chloronaphthalen-2-ylsulfonyl)glycine

To a solution of potassium carbonate (21 g) and glycine (11 g) in water (300 ml) was added 1-chloronaphthalen-2-ylsulfonyl chloride (31 g) at room temperature, and the mixture was stirred under reflux for 30 minutes.

After cooling to room temperature, the resultant solution was acidified with 2 N hydrochloric acid to a pH in the range of 1 to 2, and the formed precipitate was separated by filtration to give 33 g of the objective compound.

Melting point: 185.5°–200.7° C.

IR (KBr, $cm^{-1}$): 3380, 1720, 1325, 1135

NMR (DMSO-$d_6$, ppm): 3.63 (2H, s), 7.59–8.51 (7H, m)

Step 2

Preparation of 1-(1-chloronaphthalen-2-ylsulfonyl)-2-thiohydantoin

Anhydrous pyridine (19 ml), ammonium thiocyanate (17 g) and acetic arthydride (50 ml) were added to the product obtained in Step 1 (30 g), and the mixture was heated with stirring on a boiling water bath for 15 minutes. After cooling to room temperature, the resultant solution was poured into ice-water (300 ml), and the formed precipitate was separated by filtration to give 30.6 g of the objective compound.

Melting point: 268.6° C. (decomposition)

IR (KBr, $cm^{-1}$: 3150, 1790, 1765, 1380, 1190

NMR (DMSO-$d_6$, ppm): 4.93 (2H, s), 7.66–8.53 (5H, m), 8.78 (1H, s)

Step 3

Preparation of
1-(1-chloronaphthalen-2-ylsulfonyl)hydantoin

A mixture of the product obtained in Step 2 (20 g) and 50% (w/v, nitric acid (100 ml) was heated with stirring on a boiling water bath for 40 minutes, and the resultant solution was cooled in an ice bath. The formed precipitate was separated by filtration and washed successively with water, ethyl alcohol, methyl alcohol and dichloromethane to give 4.8 g of the objective compound.

Melting point: 258.3°–260.5° C.

IR (KBr, $cm^{-1}$): 3140, 1740, 1310, 1180

NMR (DMSO-$d_6$, ppm): 4.74 (2H, s), 7.80–8.39 (6H, m), 11.77 (1H, s)

EXAMPLE 2

Preparation of
1-(1-bromonaphthalen-2-ylsulfonyl)hydantoin
(compound 8)

Step 1

Preparation of
N-(1-bromonaphthalen-2-ylsulfonyl)glycine

Starting from 1-bromonaphthalen-2-ylsulfonyl chloride, the objective compound was obtained in a manner similar to Step 1 of Example 1.

Melting point: 199.7°–204.1° C.

NMR (DMSO-$d_6$, ppm): 3.77 (2H, d, J=6.0 Hz), 7.49–8.47 (7H, m)

Step 2

Preparation of
1-(1-bromonaphthalen-2-ylsulfonyl)-2-thiohydantoin

Starting from the product obtained in Step 1, the objective compound was obtained in a manner similar to Step 2 of Example 1.

Melting point: 253.7° C. (decomposition)

NMR (DMSO-$d_6$, ppm): 5.01 (2H, s), 7.71–8.80 (6H, m)

Step 3

Preparation of
1-(1-bromonaphthalen-2-ylsulfonyl)hydatoin

A mixture of the product obtained in Step 2 (7.5 g) and 50% (w/v) nitric acid (50 ml) was heated with stirring on a boiling water bath for 30 minutes and 60% (w/v) nitric acid (25 ml) was added. The reaction mixture was heated with stirring on a boiling water bath for 2 hours. The resultant solution was cooled in an ice bath, and the formed precipitate was sepanted by filtration and washed successively with water, methyl alcohol and dichloromethane to give 2.7 g of the objective compound.

Melting point: 287.4–292.5° C.

IR (KBr, $cm^{-1}$): 3200, 1740, 1310, 1180

NMR (DMSO-$d_6$, ppm): 4.78 (2H, s), 7.79–8.52 (6H, m), 11.75 (1H, s)

EXAMPLE 3

Preparation of
1-(3,6-dichioronaphthalen-2-ylsulfonyl)hydantein
(compound 7)

Step 1

Preparation of
N-(3,6-dichloronaphthalen-2-ylsulfonyl)glycine

To a solution of potassium carbonate (11.7 g) and glycine (6.4 g) in water (140 ml) were added 3,6-dichloronaphthalen-2-ylsulfonyl chloride (20.8 g) and dioxane (50 ml) at room temperature, and the mixture was stirred under reflux for 2 hours. After cooling to room temperature, the resultant solution was acidified with 2N hydrochloric acid to a pH in the range of 1 to 2, and extracted with ethyl acetate. The organic layer was washed with water, then with saturated aqueous NaCl solution, and dried over anhydrous sodium sulfate. Ethyl acetate was removed in vacuo to give 19.0 g of the objective compound.

Melting point: 185.0°–188.2° C.

NMR (DMSO-$d_6$, ppm): 3.82 (2H, d, J=8.0 Hz), 7.49–8.34 (5H, m), 8.63 (1H, s)

Step 2

Preparation of
1-(3,6-dichloronaphthalen-2-ylsulfonyl)-2-thiohydantoin

Starting from the product obtained in Step 1, the objective compound was obtained in a manner similar to Step 2 of Example 1.

Melting point: 252.8° C. (decomposition)

NMR (DMSO-$d_6$, ppm): 4.92 (2H, s), 7.38–8.32 (4H, m), 8.90 (1H, s)

Step 3

Preparation of
1-(3,6-dichloronaphthalen-2-ylsulfonyl)hydantoin

Starting from the product obtained in Step 2, the objective compound was obtained in a manner similar to Step 3 of Example 1.

Melting point: 263.1°–266.5° C.

IR (KBr, $cm^{-1}$): 3220, 1740, 1355, 1170

NMR (DMSO-$d_6$, ppm): 4.67 (2H, s). 7.74 (1H, d), 8.18–8.43 (3H, m), 8.98 (1H, s), 11.77 (1H, bs)

EXAMPLE 4

Preparation of
1-(5-nitronaphthalen-2-ylsulfonyl)hydantoin
(compound 11)

Step 1

Preparation of
N-(5-nitronaphthalen-2-ylsuifonyl)glycine

To a solution of potassium carbonate (3.2 g) and glycine (1.7 g) in water (50 ml) was added 5-nitronaphthalen-2-ylsulfonyl chloride (5 g) at room temperature, and the mixture was stirred under reflux for 5 minutes. After cooling to room temperature, the resultant solution was acidified with 2N hydrochloric acid to a pH in the range of 1 to 2, and the formed precipitate was separated by filtration to give 5.4 g of the objective compound.

Melting point: 235.7°–240.7° C.

IR (KBr, $cm^{-1}$): 3353, 1718, 1519, 1335, 1143

NMR (DMSO-$d_6$, ppm): 3.70 (2H, d, J=5.9 Hz), 7.73–8.64 (7H, m), 12.60 (1H, bs)

Step 2

Preparation of
1-(5-nitronaphthalen-2-ylsulfonyl)-2-thiohydantoin

Starting from the product obtained in Step 1, the objective compound was obtained in a manner similar to Step 2 of Example 1.

Melting point: 249.6°–254.8° C.

IR (KBr, $cm^{-1}$): 3303, 1794, 1767, 1519, 1453, 1343, 1163

NMR (DMSO-$d_6$, ppm): 4.88 (2H, s), 7.8C–9.03 (6H, m), 12.67 (1H, bs)

Step3

Preparation of
1-(5-nitronaphthalen-2-ylsulfonyl)hydantoin

Starting from the product obtained in Step 2, the objective compound was obtained in a manner similar to Step 3 of Example 1.

Melting point: 241.6°–245.6° C.

IR (KBr, $cm^{-1}$): 3265, 1801, 1737, 1523, 1340 1170

NMR (DMSO-$d_6$, ppm): 4.58 (2H, s), 7.81–8.96 (6H, m), 11.64 (1H, bs)

EXAMPLE 5

Preparation of
1-(6-acetamidonaphthalen-2-ylsulfonyl)hydantoin

Step 1

Preparation of
N-(6-acetamidonaphthalen-2-ylsulfonyl)glycine

Starting from 6-acetamidonaphthalen-2-ylsulfonyl chloride, the objective compound was obtained in a manner similar to Step 1 of Example 1.

Melting point: 202.2°–204.0° C.

NMR (DMSO-$d_6$, ppm): 2.11 (3H, s), 3.36 (2H, s), 5.01 (1H, bs), 7.58–8.40 (7H, m), 10.38 (1H, bs)

Step 2

Preparation of
1-(6-acetamidonaphthalen-2-ylsulfonyl)-2-thiohydantoin

Starting from the product obtained in Step 1, the objective compound was obtained in a manner similar to Step 2 of Example 1.

Melting point: 274.0°–276.9° C.

NMR (DMSO-$d_6$, ppm): 2.13 (3H, s), 4.85 (2H, s), 7.74–8.65 (6H, m), 10.30 (1H, s), 12.60 (1H, bs)

Step 3

Preparation of
1-(6-acetamidonaphthalen-2-ylsulfonyl)hydantoin

To a mixture of the product obtained in Step 2 (1.45 g), sodium bicarbonate (16 g), carbon tetrachloride (40 ml) and water (120 ml) was added slowly a solution of iodine monochloride (6.9 ml) in 1N hydrochloric acid (40 ml) at room temperature. After stirring at room temperature for 10 minutes, 6N hydrochloric acid (320 ml) was added, and the resultant solution was extracted with ethyl acetate. The organic layer was washed with saturated aqueous sodium sulfite solution, then with saturated aqueous NaCl solution, and dried over anhydrous sodium sulfate. Ethyl acetate was removed in vacuo, and the residue was washed with dichloromethane to give 1.0 g of the objective compound.

Melting point: > 300° C.

IR (KBr, $cm^{-1}$): 3400, 3250, 1740, 1360, 1165

NMR (DMSO-$d_6$, ppm): 2.14 (3H, s), 4.55 (2H, 7.60–8.56 (6H, m), 10.49 (1H, s), 11.60 (1H, s)

Compounds of Example 6 to 25 prepared in a manner similar to Example 1 are summarized in the following table 3 together with corresponding IR and NMR data and melting points.

TABLE 3

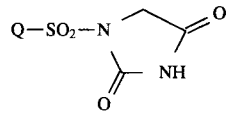

| Ex. No. | Q | IR(KBr, $cm^{-1}$) | NMR(DMSO-$d_6$, ppm) | M.P. (°C.) |
|---|---|---|---|---|
| 6 | 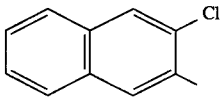 | 3250, 1735, 1350, 1160 | 4.57(2H, s), 7.67~8.34(5H, m), 8.74(1H, s), 11.60(1H, bs) | 259.6~262.0 |

TABLE 3-continued
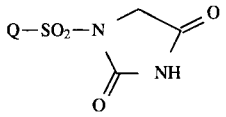
| Ex. No. | Q | IR(KBr, $cm^{-1}$) | NMR(DMSO-$d_6$, ppm) | M.P. (°C.) |
|---|---|---|---|---|
| 7 | 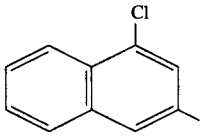 | 3250, 1735, 1350, 1165 | 4.58(2H, s), 7.89~8.73(6H, m), 11.62(1H, bs) | 256.7~261.0 |
| 8 | 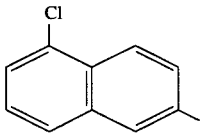 | 3230, 1730, 1350, 1160 | 4.57(2H, s), 7.62~8.80(6H, m), 11.62(1H, bs) | 293.0~299.5 |
| 9 | 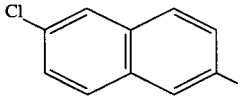 | 3230, 1720, 1350, 1150 | 4.57(2H, s), 7.69~8.75(6H, m), 11.61(1H, bs) | 238.7~241.4 |
| 10 | 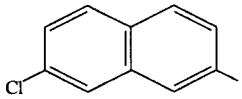 | 3160, 1730, 1375, 1170 | 4.56(2H, s), 7.71~8.70(6H, m), 11.62(1H, bs) | 261.0~263.9 |
| 11 | 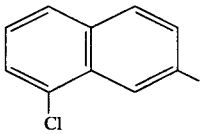 | 3230, 1730, 1350, 1160 | 4.56(2H, s), 7.69~8.82(6H, m), 11.61(1H, bs) | 233.7~235.3 |
| 12 | 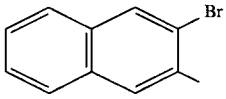 | 3240, 1730, 1360, 1180 | 4.72(2H, s), 7.74~8.26(4H, m), 8.54(1H, s), 8.96(1H, s), 11.77(1H, bs) | 298.0~303.0 |
| 13 | 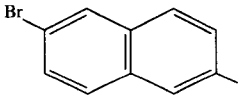 | 3220, 1730, 1350, 1160 | 4.57(2H, s), 7.80~8.74(6H, m), 11.61(1H, bs) | 255.6~258.6 |
| 14 | 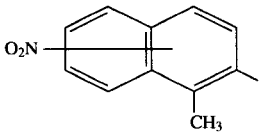 | 3250, 1735, 1520, 1340, 1150 | 3.08(3H, s), 4.58(2H, s), 7.90~8.73(5H, m), 11.69(1H, bs) | 232.0~236.5 |
| 15 | 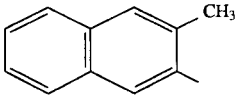 | 3200, 1725, 1340, 1160 | 2.70(3H, s), 4.55(2H, s), 7.62~8.14 (5H, m), 8.75(1H, s), 11.65(1H, bs) | 271.4~277.3 |
| 16 | 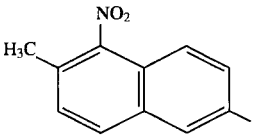 | 3170, 1730, 1530, 1370, 1170 | 2.52(3H, s), 4.55(2H, s), 7.74~8.48 (4H, m), 8.85(1H, s), 11.62(1H, bs) | 295.0~296.1 |
| 17 | 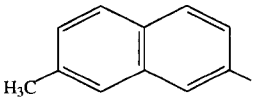 | 3240, 1735, 1350, 1160 | 2.53(3H, s), 4.56(2H, s), 7.51~8.63(6H, m), 11.58(1H, bs) | 212.1~215.3 |

TABLE 3-continued

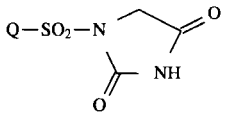

| Ex. No. | Q | IR(KBr, $cm^{-1}$) | NMR(DMSO-$d_6$, ppm) | M.P. (°C.) |
|---|---|---|---|---|
| 18 | 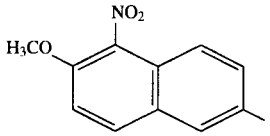 | 3180, 1740, 1530, 1370, 1170 | 4.11(3H, s), 4.54(2H, s), 7.75~8.83(5H, m), 11.61(1H, bs) | 285.9~286.4 |
| 19 | 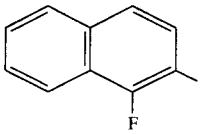 | 3170, 1720, 1365, 1180 | 4.56(2H, s), 7.78~8.20(6H, m), 11.67(1H, bs) | 231.0~234.0 |
| 20 | 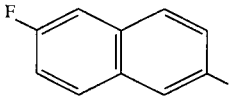 | 3230, 1730, 1350, 1150 | 4.50(2H, s), 7.78~8.39(6H, m), 11.60(1H, bs) | 162.6~166.0 |
| 21 | 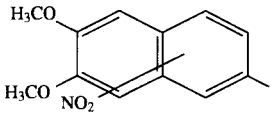 | 3250, 1735, 1365, 1165 | 4.02(3H, s), 4.06(3H, s), 4.54(2H, s), 7.72~8.80(4H, m), 11.65(1H, bs) | 228.0~230.0 |
| 22 | 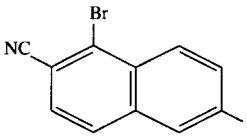 | 3150, 2230, 1735, 1380, 1170 | 4.57(2H, s), 8.01~8.91(5H, m), 11.65(1H, bs) | 279.0~285.0 |
| 23 | 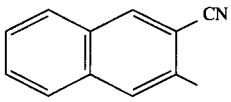 | 3230, 2240, 1740, 1380, 1160 | 4.58(2H, s), 7.93~8.49(4H, m), 8.75 (1H, s), 8.84(1H, s), 11.63(1H, bs) | 261.6~264.6 |
| 24 | 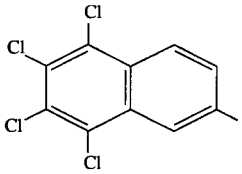 | 3230, 1740, 1380, 1170 | 4.54(2H, s), 8.27~8.87(3H, m), 11.60(1H, bs) | >300 |
| 25 | 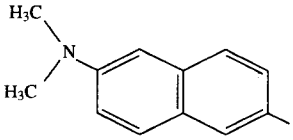 | 3240, 1740, 1370, 1170 | 2.94(6H, s), 4.53(2H, s), 7.35~8.59(6H, m), 11.56(1H, bs) | 102.9~104.5 |

EXAMPLE 26

Preparation of 1-(benzo[b]thiophen-2-ylsulfonyl)hydantoin (compound 16)

Step 1

Preparation of benzo[b]thiophen-2-ylsulfonyl chloride

To a solution of benzo[b]thiophen (38.3 g) in anhydrous ether (180 ml) was added dropwise 1.6 M solution of n-butyllithium in hexane (220 ml) under ice-cooling and nitrogen atmosphere. After refluxing for 40 minutes, into the solution was bubbled sulfur dioxide for 2.75 hours with stirring at −30° C. Then the solution was stirred for 1 hour and the formed precipitate was separated by filtration to give lithium benzo[b]thiophen-2-ylsulfinate. Into the suspension of the product in concentrated hydrochloric acid (400 ml) and water (100 ml) was bubbled chlorine gas for 1.5 hours with stirring at −5° C. The resulting solution was poured into ice-water (500 ml) and extracted with dichloromethane (1.51×2) and the organic layer was washed with saturated aqueous NaCl solution. After drying over anhydrous magnesium sulfate, dichloromethane was removed in vacuo, and the residue was purified by silica gel column chromatography to give 40.4 g of the objective compound.

IR (KBr, $cm^{-1}$): 1495, 1384, 1189, 1168, 1155

NMR ($CDCl_3$, ppm): 7.49–7.68 (2H, m), 7.86–8.03 (2H, m), 8.14 (1H, s)

Step 2

Preparation of N-(benzo[b]thiophen-2-ylsulfonyl)glycine

Starting from benzo[b]thiophen-2-ylsulfonyl chloride, the objective compound was obtained in a manner similar to Step 1 of Example 1.

Melting point: 171.3°–172.4° C.

IR (KBr, $cm^{-1}$): 3267, 1735, 1352, 1258, 1115, 1115

NMR (DMSO-$d_6$, ppm): 3.73 (2H, d, J=6.0 Hz), 7.39–7.61 (2H, m), 7.77–8.13 (3H, m), 8.51 (1H, d, J=6.0 Hz), 12.68 (1H, bs)

Step 3

Preparation of 1-(benzo[b]thiophen-2-ylsulfonyl)-2-thiohydantoin

Starting from the product obtained in Step 2, the objective compound was obtained in a manner similar to Step 2 or Example 1.

Melting point: 218.6° C. (decomposition)

IR (KBr, $cm^{-1}$): 1759, 1374, 1255, 1171, 1157

NMR (DMSO-$d_6$, ppm): 4.74 (2H, s), 7.35–7.69 (2H, m), 8.04–8.21 (2H, m), 8.45 (1H, s), 12.72 (1H, bs)

Step 4

Preparation of 1-(benzo[b]thiophen-2-ylsulfonyl)hydantoin

To a suspension of iodine monochloride (7.12 ml) in 1 N hydrochloric acid (200 ml) were added successively the product obtained in Step 3 (8.50 g) and dichloromethane (200 ml). The mixture was stirred for 20 minutes at room temperature. After adding sodium bicarbonate (6.85 g), the reaction mixture was stirred for 15 minutes and extracted twice with ethyl acetate (11+300 ml). The organic layer was washed with saturated aqueous sodium bisulfite solution and then saturated aqueous NaCl solution, and dried over anhydrous magnesium sulfate. Ethyl acetate was removed in vacuo, the residue was washed with dichloromethane to give 4.83 g of the objective compound.

Melting point: 251.8°–254 2° C.

IR (KBr, $cm^{-1}$): 3245, 1803, 1740, 1376, 1352, 1167

NMR (DMSO-$d_6$, ppm): 4.48 (2H, s), 7.51–7.63 (2H, m), 8.05–8.20 (2H, m), 8.33 (1H, s), 11.71 (1H, bs)

EXAMPLE 27

Preparation of 1-(benzo[b]furan-2-ylsulfonyl)hydantoin (compound 19)

Step 1

Preparation of benzo[b]furan-2-ylsulfonyl chloride

Starting from benzo[b]furan, the objective compound was obtained in a manner similar to Step 1 of Example 26.

IR (KBr, $cm^{-1}$): 1533, 1389, 1244, 1193, 1166

NMR ($CDCl_3$, ppm): 7.32–7.82 (5H, m)

Step 2

Preparation of N-(benzo[b]furan-2-ylsulfonyl)glycine

Starting from benzo[b]furan-2-ylsulfonyl chloride, the objective compound was obtained in a manner similar to Step 1 of Example 1.

Melting point: 177.0°–178.2° C.

IR (KBr, $cm^{-1}$): 3289, 1724, 1347, 1162

NMR (DMSO-$d_6$, ppm): 3.77 (2H, d, J=6.3 Hz), 7.35–7.81 (5H, m), 8.72 (1H, t, J=6.3 Hz), 12.69(1H, bs)

Step 3

Preparation of 1-(benzo[b]furan-2-ylsulfonyl)-2-thiohydantoin

To a suspension of the product obtained in Step 2 (37.0 g) and ammonium thiocyanate (24. 3 g) in acetic anhydride (100 ml) was added dropwise anhydrous pyridine (30.5 ml), and the mixture was heated with stirring for 1.5 hours at 70°–80° C. After cooling to room temperature, the resultant solution was poured into ice (800 g), and the formed precipitate was separated by decantation. The precipitate was washed with water and dried to give 18.5 g of the objective compound.

Melting point: 213.0° C. (decomposition)

IR (KBr, $cm^{-1}$): 3080, 1759, 1386, 1255. 1167 1096

NMR (DMSO-$d_6$, ppm): 4.76 (2H, s), 7.34–8.04 (5H, m), 12.81 (1H, bs)

Step 4

Preparation of 1-(benzo[b]furan-2-ylsulfonyl) hydantoin

Starting from the product obtained in Step 3, the objective compound was obtained in a manner similar to Step 4 of Example 26.

Melting point: 255.9°–256.4° C.

IR(KBr, $cm^{-1}$): 1803, 1735, 1398, 1360, 1166

NMR (DMSO-$d_6$, ppm): 4.49 (2H, s), 7.33–8.08

Compounds of Example 28 to 52 prepared in a manner similar to Example 26 are summarized in the following table 4 together with corresponding IR and NMR data and melting points.

TABLE 4
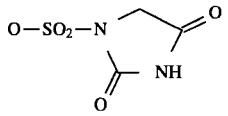
| Ex. No. | Q | IR(KBr, $cm^{-1}$) | NMR(DMSO-$d_6$, ppm) | M.P. (°C.) |
|---|---|---|---|---|
| 28 | 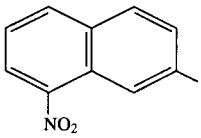 | 1803, 1755, 1516, 1372, 1350, 1165 | 4.55(2H, s), 7.86~9.10(6H, m), 11.62(1H, bs) | 284.6 (dec.) |
| 29 | 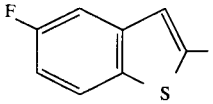 | 1735, 1508, 1382, 1167 | 4.47(2H, s), 7.40~8.30(3H, m), 8.30(1H, s), 11.73(1H, bs) | 275.2 (dec) |
| 30 | 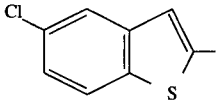 | 1739, 1380, 1192 | 4.45(2H, s), 7.57~7.69(1H, m), 8.15~8.25(2H, m), 8.29(1H, s), 11.70(1H, bs) | >300 |
| 31 | 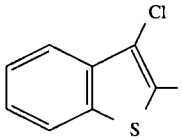 | 1728, 1381, 1183, 1162 | 4.64(2H, s), 7.58~7.81(2H, m), 7.96~8.06(1H, m), 8.18~8.29(1H, m), 11.82(1H, bs) | 278.3 (dec.) |
| 32 | 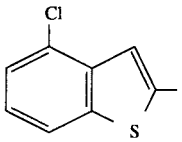 | 3270, 1741, 1379, 1162 | 4.51(2H, s), 7.52~7.67(2H, m), 8.16~8.23(2H, m), 11.74(1H, bs) | 271.1~272.2 |
| 33 | 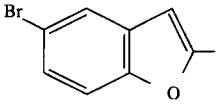 | 3400, 1730, 1663, 1614, 1380, 1169 | 3.96(2H, s), 7.61~8.06(4H, m) | 270.2 (dec.) |
| 34 | 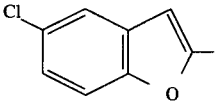 | 3379, 1616, 1608, 1381, 1233, 1166. | 3.98(2H, s), 7.47~7.90(4H, m) | 290.0 (dec.) |
| 35 | 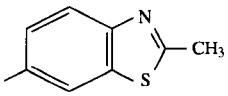 | 1740, 1376, 1166 | 2.88(3H, s), 4.53(2H, s), 8.10(2H, s), 8.80(1H, s), 11.59(1H, bs) | 258.0 (dec.) |
| 36 | 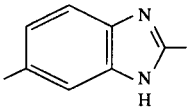 | 3328, 1740, 1390, 1159 | 4.60(2H, s), 7.33~7.78(5H, m), 11.85(1H, bs) | 222.8 (dec.) |
| 37 | 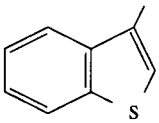 | 1741, 1380, 1162 | 4.54(2H, s), 7.52~7.63(2H, m), 8.10~8.29 (2H, m), 8.86(1H, s), 11.58(1H, bs) | 218.3~226.7 |
| 38 | 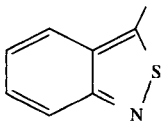 | 1739, 1377, 1165 | 4.49(2H, s), 7.50~8.28(4H, m), 11.68(1H, bs) | 237.8~243.0 |

TABLE 4-continued
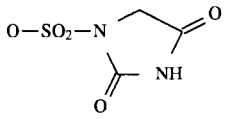
| Ex. No. | Q | IR(KBr, $cm^{-1}$) | NMR(DMSO-$d_6$, ppm) | M.P. (°C.) |
|---|---|---|---|---|
| 39 | 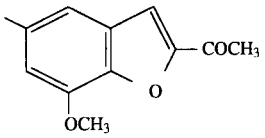 | 1746, 1682, 1363, 1158 | 2.59(3H, s), 4.07(3H, s), 4.51(2H, s), 7.57~8.13(3H, m), 11.55(1H, bs) | 263.0 (dec.) |
| 40 | 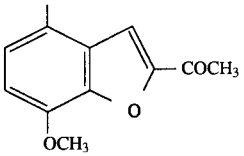 | 1735, 1691, 1387, 1173 | 2.63(3H, s), 4.10(3H, s), 4.54(2H, s), 7.36(1H, d, J=8.6Hz), 8.02(2H, m), 11.56(1H, bs) | 242.3~244.1 |
| 41 | 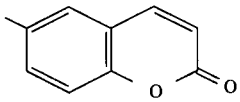 | 1803, 1746, 1716, 1377, 1164 | 4.51(2H, s), 6.64(1H, d, J=9.9Hz), 7.62(1H, d, J=8.9Hz), 8.11~8.46(3H, m), 11.60(1H, bs) | 262.8~267.8 |
| 42 | 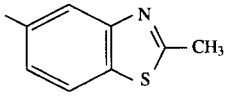 | 1741, 1371, 1169 | 2.87(3H, s), 4.55(2H, s), 7.95~8.51(3H, m), 11.59(1H, bs) | 245.2~246.3 |
| 43 | 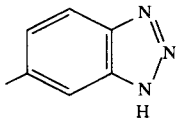 | 1741, 1362, 1168 | 4.55(2H, s), 8.12(2H, s), 8.82(1H, s), 12.67(1H, bs) | |
| 44 | 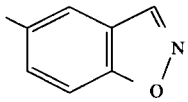 | 3098, 1743, 1385, 1364, 1186, 1162, 1067 | 4.52(2H, s), 7.99~8.66(3H, m), 9.45(1H, d, J=1.0Hz), 11.59(1H, bs) | 203 (dec.) |
| 45 | 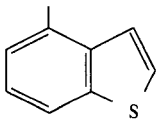 | 3095, 1741, 1373, 1360, 1177, 1150 | 4.56(2H, s), 7.51~8.51(5H, m), 11.59(1H, bs) | 238.7~244.9 |
| 46 | 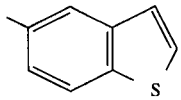 | 1729, 1362, 1166 | 4.54(2H, s), 7.66~8.59(5H, m), 11.56(1H, bs) | 268.4~271.4 |
| 47 | 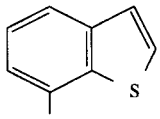 | 3174, 1735, 1390, 1170 | 4.61(2H, s), 7.57~7.74(2H, m), 7.95~8.34(3H, m), 11.55(1H, bs) | 242.9~244.3 |
| 48 | 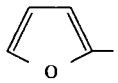 | 1800, 1742, 1396, 1162 | 4.43(2H, s), 6.78(1H, m), 7.45(1H, d, J=3.6Hz), 8.09(1H, m), 11.72(1H, bs) | 243.0~244.2 |
| 49 | 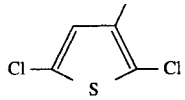 | 3227, 1735, 1365, 1183, 1171 | 4.51(2H, s), 7.55(1H, s), 11.76(1H, bs) | 251.2~251.3 |

TABLE 4-continued

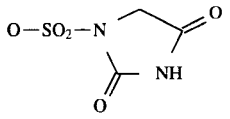

| Ex. No. | Q | IR(KBr, $cm^{-1}$) | NMR(DMSO-$d_6$, ppm) | M.P. (°C.) |
|---|---|---|---|---|
| 50 | 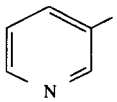 | 1742, 1375, 1174 | 4.53(2H, s), 7.71(1H, m), 8.40(1H, m), 8.89~9.14(2H, m), 11.65(1H, bs) | 175.5 (dec.) |
| 51 | $CH_3-$ | 1744, 1384, 1359, 1164, 1153 | 3.35(3H, s), 4.33(2H, s), 11.65(1H, bs) | 196.2~198.3 |
| 52 | 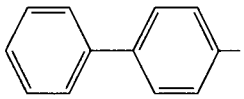 | 1749, 1727, 1371, 1170 | 4.55(2H, s), 7.38~8.16(9H, m), 11.63(1H, bs) | 261.0~261.5 |

EXAMPLE 53

Preparation of 1-(4,5-diphenythiophen-2-ylsulfonyl)hydantoin

Step 1

Preparation of 4,5-diphenylthiophen-2-ylsulfonyl chloride

Starting from 2,3-diphenyhhiophen, the objective compound was obtained in a manner similar to Step 1 of Example 26.

IR (KBr, $cm^{-1}$): 1382, 1172, 1038, 698, 583

NMR ($CDCl_3$, ppm): 7.27–7.33 (10H, m), 7.89 (1H, s)

Step 2

Preparation of N-(4,5-diphenyhhiophen-2-ylsulfonyl)glycine ethyl ester

To a suspension of 4,5-diphenyhhiophen-2-ylsulfonyl chloride (36.5 g) and glycine ethyl ester hydrochloride (30.4 g) in dichloromethane (320 ml) was added slowly triethylamine (3.03 mi) under ice-cooling, and the mixture was stirred for 160 minutes at room temperature. Water (200 ml) was added to the resultant solution, and extracted with dichloromethane. The organic layer was washed successively with 1N hydrochloric acid, water and saturated aqueous NaCl solution, and dried over anhydrous magnesium sulfate. Dichloromethane was removed in vacuo, and the residue was reprecipitated from ethyl acetate and hexane to give 41.1 g of the objective compound.

Melting point: 151.2°–152.7° C.

IR (KBr, $cm^{-1}$): 3266, 1734, 1354, 1231, 1215, 1164, 1127

NMR (DMSO-$d_6$, ppm): 1.12 (3H, t, J= 7.1 Hz), 3.88 (2H, d, J=6.3 Hz), 4.04 (2H, q, J=7.1 Hz), 6.84–7.44 (10H, m), 7.67 (1H, s), 8.57 (1H, t, J=6.3 Hz)

Step 3

Preparation of N-(4,5-diphenylthiophen-2-ylsuifonyl)glycine

A solution of sodium hydroxide (12.4 g) in water (73 ml) was added to a solution of the product obtained in Step 2 (41.4 g) in tetrahydrofuran (730 ml), and the mixture was stirred for 25 minutes at 60° C. After removing the solvent, water (300 ml) was added to the residue, and the resultant solution was acidified with concentrated hydrochloric acid to a pH 1 under ice-cooling. The acidified solution was extracted thrice with ethyl acetate (800 ml), the organic layer was washed with water, then with maturated aqueous NaCl solution, and dried over anhydrous sodium sulfate. Ethyl acetate was removed in vacuo, the residue was reprecipitated from ethyl acetate and hexane to give 37.6 g of the objective compound.

Melting point: 172.2°–174.4° C.

IR (KBr, $cm^{-1}$): 3268, 1736, 1353, 1159

NMR (DMSO-$d_6$, ppm): 3.78 (2H, d, J=5.9 Hz), 7.12–7.42 (10H, m), 7.67 (1H, s), 8.39 (1H, t, J=5.9 Hz), 12.78 (1H, bs)

Step 4

Preparation of 1-(4,5-diphenylthiophen-2-ylsulfonyl-2-thiohydantoin

Starting from the product obtained in Step 3, the objective compound was obtained in a manner similar to Step 2 of Example 1.

Melting point: 213.2°–215.4° C.

IR (KBr, $cm^{-1}$): 1752, 1446, 1376, 1168, 1083

NMR (DMSO-$d_6$, ppm): 4.77 (2H, s), 7.32–7.46 (10H, m), 8.12 (1H, s), 12.73 (1H, bs)

Step 5

Preparation of 1-(4,5-diphenylthiophen-2-ylsulfonyl)hydantoin

Starting from the product obtained in Step 4, the objective compound was obtained in a manner similar to Step 4 of Example 26.

Melting point: 242.5°–243.9° C.

IR (KBr, $cm^{-1}$): 1737, 1386, 1165

NMR (DMSO-$d_6$, ppm): 4.53 (2H, s), 7.32–7.45 (10H, m), 8.00 (1H, s), 11.72 (1H, bs)

Compounds of Example 54 and 55 prepared in a manner similar to Example 53 are summarized in the following table 5 together with corresponding IR and NMR data and melting points.

TABLE 5

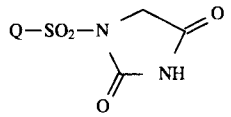

| Ex. No. | Q | IR(KBr, $cm^{-1}$) | NMR(DMSO-$d_6$, ppm) | M.P. (°C.) |
|---|---|---|---|---|
| 54 | 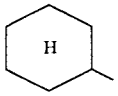 | 1721, 1367, 1349, 1172, 1161 | 0.96~2.40(10H, m), 3.30~3.69(1H, m), 4.31(2H, s), 11.61(1H, bs) | 154.9~156.7 |
| 55 | 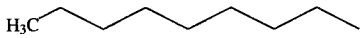 | 1735, 1725, 1359, 1163 | 0.69~1.98(15H, m), 3.42~3.59(2H, m), 4.33(2H, s), 11.64(1H, bs) | 141.3~143.2 |

EXAMPLE 56

Preparation of 1-(5-nitrobcnzo[b]thlophen-2-ylsulfonyl)hydantoin. (compound 42)

Step 1

Preparation of 5-nitrobenzo[b]thiophen-2-ylsulfonyl chloride

To a solution of 5-nitrobenzo[b]thiophen (60 g) in anhydrous tetrahydrofuran (2 l) was added dropwise a solution of lithium diisopropylamide comprising 1.6M n-butyllithium in hexane (240 ml) and diisopropylamine (57.8 ml) and anhydrous ether (170 ml) with stirring at −70° C. under nitrogen atmosphere. After stirring for 30 minutes into the solution was bubbled sulfur dioxide for 90 minutes with stirring at −70° C. Then the solution was stirred for 1 hour at room temperature and the formed precipitate was separated by filtration to give lithium 5-nitrobenzo[b]-thiophen-2-ylsulfinate. Into the suspension of the product in concentrated hydrochloric acid (500 ml) and water (125 ml) was bubbled chlorine gas for 3 hours with sufficiently stirring at below 0° C. After stirring for 1 hour at room temperature, the resulting suspension was extracted with dichloromethane (400 ml×2) and the organic layer was washed with successive water and saturated aqueous NaCl solution. After drying over anhydrous sodium sulfate, dichloromethane was removed in vacuo, and the residue was purified by silica gel column chromatography to give 21 g of the objective compound.

IR (KBr, $cm^{-1}$): 1602. 1519, 1378, 1340, 1172

NMR ($CDCl_3$, ppm): 8.10 (1H, d, J=8.9 Hz), 8.31 (1H, s), 8.46 (1H, dd, J=8.9, 2.0 Hz), 8.90 (1H, d, J=2.0 Hz)

Step 2

Preparation of N-(5-nitrobenzo[b]thiophen-2-ylsulfonyl)glycine

Starting from 5-nitrobenzo[b]thiophen-2-ylsulfonyl chloride, the objective compound was obtained in a manner similar to Step 1 or Example 1.

Melting point: 187.2°–194.8° C.

IR (KBr, $cm^{-1}$): 3325, 1734, 1530, 1377, 1351, 1159

NMR (DMSO-$d_6$, ppm): 3.76 (2H, d, J= 5.9 Hz), 8.22 (1H, s), 8.32–8.91 (4H, m), 12.72 (1H, bs)

Step 3

Preparation of 1-(5-nitrobenzo[b]thiophen-2-ylsulfonyl)-2-thiohydantoin

Starting from the product obtained in Step 2, the objective compound was obtained in a manner similar to Step 2 of Example 1.

Melting point: 217.4° C. (decomposition)

IR (KBr, $cm^{-1}$): 1762, 1521, 1470. 1389, 1347, 1248, 1173, 1087

NMR (DMSO-$d_6$, ppm): 4.73 (2H, s), 8.25–9.09 (4H, m), 12.78 (1H, bs)

Step 4

Preparation of 1-(5-nitrobenzo[b]thiophen-2-ylsulfonyl)hydantoin

A mixture of the product obtained in Step 3 (1.66 g) and 50% (w/v) nitric acid (35 ml) was heated with stirring for 6 hours at 60° C, and the resultant solution was poured into ice-water (150 ml). The formed precipitate was separated by filtration and washed with acetone to give 0.47 g of the objective compound.

Melting point: 282.4° C. (decomposition)

IR (KBr, $cm^{-1}$): 3100, 1737, 1522, 1385, 1349, 1176

NMR (DMSO-$d_6$, ppm): 4.47 (2H, s), 8.22–9.05 (4H, m), 11.70 (1H, bs)

EXAMPLE 57

Preparation of
1-(5-cyanobenzo[b]thiophen-2-ylsulfonyl)hydantoin

Step 1

Preparation of
5-cyanobenzo[b]thiophen-2-ylsulfonyl chloride.

Starting from benzo[b]thiophen-5-ylcarbonitrile, the objective compound was obtained in a manner similar to Step 1 of Example 56.

IR (KBr, $cm^{-1}$): 2236, 1500, 1376, 1171, 577

NMR (DMSO-$_6$, ppm): 7.56 (1H, s), 7.70 (1H, dd, J=8.9, 2.0 Hz), 8.15 (1H, d, J=8.9 Hz), 8.37 (1H, d, J=2.0 Hz)

Step 2

Preparation of
N-(5-cyanobenzo[b]thiophen-2-ylsulfonyl)glycine

Starting from 5-cyanobenzo[b]thiophen-2-ylsulfonyl chloride, the objective compound was obtained in a manner similar to Step 1 of Example 1.

IR (KBr, $cm^{-1}$): 3289, 2235. 1714, 1350, 1153

NMR (DMSO-$d_6$, ppm): 3.75 (2H, d, J=5.6 Hz), 7.87 (1H, dd, J=8.6, 1.3 Hz), 8.06 (1H, s), 8.34 (1H, d, J=8.6 Hz), 8.56 (1H, d, J= 1.3 Hz), 8.70 (1H, t, J=5.6 Hz), 12.69 (1H, bs)

Step 3

Preparation of
1-(5-cyanobenzo[b]thiophen-2-ylsulfonyl)-
2-thiohydantoin

Starting from the product obtained in Step 2, the objective compound was obtained in a manner similar to Step 2 of Example 1.

IR (KBr, $cm^{-1}$): 2231, 1762, 1451, 1243, 1173, 1077

NMR (DMSO-$d_6$, ppm): 4.73 (2H, s), 7.95 (1H, dd, J=8.6, 1.7 Hz), 8.41 (1H, d, J=8.6 Hz), 8.53 (1H, s), 8.63 (1H, d, J=1.7 Hz), 12.72 (1H, bs)

Step 4

Preparation of
1-(5-cyanobenzo[b]thiophen-2-ylsulfonyl)hydantoin

A mixture of the product obtained in Step 3 (0.39 g) and 50% (w/v) nitric acid (8.2 mi) was heated with stirring for 5 minutes at 80° C., then for 30 minutes at room temperature, and the resultant solution was poured into ice-water (35 ml). The formed precipitate was separated by filtration and washed with acetone (100 ml) to give 0.11 g of the objective compound.

Melting point: 276.3° C. (decomposition)

IR (KBr, $cm^{-1}$): 3100, 2231, 1740, 1386, 1172

NMR DMSO-$d_6$, ppm) 4.47 (2H, s), 7.95 (1H, dd, J=8.6, 1.7 Hz), 8.41 (1H, s), 8.42 (1H, d, J=8.6 Hz), 8.65 (1H, d, J=1.7 Hz), 11.75(1H, bs)

EXAMPLE 58

Preparation of
1-(5-carboxybenzo[b]thiophen-2-ylsulfonyl)hydantoin

To the suspension of the product obtained in Step 4 of Example 57 (0.1 g) in water (1.5 ml) was added slowly concentrated sulfuric acid (1.5 ml) and acetic acid (1.5 ml) under ice-cooling, and the mixture was stirred under reflux for 2 hours. After cooling to room temperature, the formed precipitate was separated by filtration and washed with acetone (20 ml). The washings were concentrated in vacuo, and the residue was triturated with ether (2 ml) to give 0.02 g of the objective compound.

Melting point: >300° C.

IR (KBr, $cm^{-1}$): 1743, 1690, 1380. 1163

NMR (DMSO-$d_6$, ppm): 4.46 (2H, s), 8.07 (1H, dd, J=8.6, 1.7 Hz), 8.28 (1H, d, J=8.6 Hz), 8.48 (1H, s), 8.69(1H, d, J=1.7 Hz)

EXAMPLE 59

Preparation of 1-(indol-2-ylsulfonyl)hydantoin

Step 1

Preparation of 1-benzenesulfonylindol-2-ylsulfonyl chloride

To a solution of lithium diisopropylamide comprising 1.6M n-butyllithium in hexane (422 ml), diisopropylamine (101 ml) and anhydrous ether (260 ml) was added dropwise, solution of 1-benzenesulfonylindole (150 g) in anhydorous ether (2060 ml) with stirring at 0° C. After stirring for 15 mlnutes at 0° C., the solution was poured into sulfuryl chloride (125 ml) at −50° C. and stirred for 2 hours. The resulting solution was poured into ice-water (2.51) and stirred sufficiently and then the organic layer was extracted. The aqueous layer was extracted with ethyl acetate (2l) and the combined organic layer was washed with successive water and saturated aqueous NaCl solution. After drying over anhydrous sodium sulfate, ether and ethyl acetate were removed in vacuo and the residue was triturated with ether to give 146 g of the objective compound.

IR (KBr, $cm^{-1}$): 1513, 1387, 1378, 1245, 1188

NMR ($CDCl_3$, ppm): 7.29–8.36 (10 H, m)

Step 2

Preparation of

N-(1-benzenesulfonylindol-2-ylsulfonyl)glycine ethyl ester

Starting from 1-benzenesulfonylindol-2-ylsulfonyl chloride, the objective compound was obtained in a manner similar to Step 2 of Example 53.

IR (KBr, $cm^{-1}$): 3335, 1746, 1346, 1338, 1171

NMR(DMSO-$d_6$, ppm): 1.11 (3H, t, J=7.3 Hz),3.94 (2H, d, J=5.6 Hz), 4.06 (2H, q, J=7.3 Hz), 6.38 (1H, t. J=5.6 Hz), 7.14–8.32 (10H, m)

Step 3

Preparation of N-(indol-2-ylsulfonyl)glycine

A solution of sodium hydroxide (1.6 g) in water (7 ml) was added to a solution of the product obtained in Step 2 (4.22 g) in tetrahydrofuran (70 ml) at room temperature, and the mixture was stirred for 5 mlnutes at 65°–75° C. After removing tetrahydofuran in vacuo, a solution of sodium hydroxide (0.4 g) in water (23 ml) was added to the residue, and the mixture was stirred for 5 hours at 65°–75° C. After cooling to room temperature, the resultant solution was washed with ether, acidified with 6N hydrochloric acid to a pH 1 under ice-cooling, and extracted with ethyl acetate (15 ml×3). The organic layer was washed with water and saturated aqueous NaCl solution, and dried over anhydrous sodium sulfate. Ethyl acetate was removed in vacuo, and the residue was triturated with ethyl acetate and hexane to give 1.66 g of the objective compound.

Melting point: 170.2°–171.9° C.

IR (KBr, $cm^{-1}$): 3328, 1707, 1340, 1155, 1145

NMR (DMSO-$d_6$, ppm): 3.73 (2H, d, J=6.3 Hz), 6.94–7.70 (5H, m), 8.05 (1H, t, J=6.3 Hz), 11.90 (1H, bs), 12.67 (1H, bs)

Step 4

Preparation of 1-(indol-2-ylsulfonyl)-2-thiohydantoin

Starting from the product obtained in Step 3, the objective compound was obtained in a manner similar to Step 2 of Example 1.

Melting point: 209.2°–210.4° C.

IR (KBr, $cm^{-1}$): 3131, 3103, 1755, 1473, 1367, 1249, 1197, 1165, 1147, 1079

NMR (DMSO-$d_6$, ppm): 4.81 (2H, s), 7.08–7.78 (5H, m), 12.33 (1H, bs), 12.66 (1H, bs)

Step 5

Preparation of 1-(indol-2-ylsulfonyl)hydantoin

Starting from the product obtained in Step 4, the objective compound was obtained in a manner similar to Step 4 of Example 26.

Melting point: 287.1° C. (decomposition)

IR (KBr, $cm^{-1}$): 3290, 1787, 1725, 1389, 1365, 1156

NMR ($DMSO_6$, ppm): 4.67 (2H, s), 7.29–7.58 (5H, m), 11.67 (1H, bs), 12.63 (1H, bs)

EXAMPLE 60

Preparation of 1-(2-carboxychromon-6-ylsulfonyl)hydantoin

Step 1

Preparation of 2-methoxycarbonylchromon-6-ylsulfonyl chloride

To a solution of methyl 6-aminochromon-2-carboxylate (20 g) in water (132 ml) was added concentrated sulfuric acid (26.4 m') and then sodium nitrite (9.0 g) at 0° C. After stirring for 30 mlnutes, to the solution was added sulfur dioxide (19.7 ml), acetic acid (112 ml), concentrated hydrochloric acid (26 ml) and copper (II) chloride dihydrate (11.2 g) and then the mixture was stirred for 15 mlnutes. The formed precipitate was separated by filtration and dissolved in dichloromethane (600 ml) and the resulting solution was washed with saturated aqueous NaCl solution. After drying over anhydrous sodium sulfate, dichloromethane was removed in vacuo to give 22 g of the objective compound.

IR (KBr, $cm^{-1}$): 1744, 1661, 1381, 1287, 1174. 600

NMR (DMSO-$d_6$, ppm): 6.96 (1H, s), 7.70 (1H, d, J=8.6 Hz). 8.04 (1H, dd, J=8.6, 2.0 Hz), 8.25 (1H, d, J=2.0 Hz)

Step 2

Preparation of N-(2-methoxycarbonylchromon-6-ylsulfonyl)glycine

To a suspension of 2-methoxycarbonylchromon-6-ylsulfonyl chloride (20.0 g) in acetone (600 ml) was added slowly a solution of glycine (6.15 g), sodium hydroxide (3.28 g) and sodium bicarbonate (6.11 g) in water (300 ml), and the mixture was stirred for 85 mlnutes at room temperature. After adjusting a pH of the resultant solution to ca. 6 with 6 N hydochloric acid, acetone was removed in vacuo, and insoluble matters were filtered off. The filtrate was acidified with 2 N hydrochloric acid to a pH 1 under ice-cooling. The acidified solution was extracted with ethyl acetate (350 ml×3), the organic layer was washed with water, then saturated aqueous NaCl solution. and dried over anhydrous sodium sulfate. Ethyl acetate was removed in vacuo, the residue was purified by silica-gel column chromatography to give 5.45 g of the objective compound.

Melting point: 210.6°–212.8° C.

IR (KBr, $cm^{-1}$): 3327, 1746, 1716, 1659, 1288, 1266, 1165

NMR (DMSO-$d_6$, ppm): 3.67 (2H, d, J= 5.9 Hz), 3.96 (3H, s), 7.04 (1H, s), 7.89–8.42 (4H, m)

Step 3

Preparation of 1-(2-methoxycarbonylchromon-6-ylsulfonyl)-2-thiohydantoin

Starting from the product obtained in Step 2, the objective compound was obtained in a manner similar to Step 2 of Example 1.

Melting point: 217.4° C. (decomposition)

IR (KBr, $cm^{-1}$): 1746. 1660, 1443, 1374, 1282, 1260, 1174

NMR (DMSO-$d_6$, ppm): 3.96 (3H, s), 4.84 (2H, s), 7.07 (1H, s), 7.9–8.71 (3H, m), 12.68 (1H, bs)

Step 4

Preparation of 1-(2-methoxycarbonylchromon-6-ylsulfonyl)hydantoin

Starting from the product obtained in Step 3, the objective compound was obtained in a manner similar to Step 4 of Example 26.

Melting point: >300° C.

IR (KBr, $cm^{-1}$): 1751, 1741, 1664, 1617, 1375. 1177,

NMR (DMSO-$d_6$, ppm): 3.96 (3H, s), 4.52 (2H, s) 7.07 (1H, s), 7.98–8.64 (3H, m)

Step 5

Preparation of
1-(2-carboxychromon-6-ylsulfonyl)hydantoin

A solution of the product obtained in Step 4 (2.27 g) in a saturated aqueous sodium bicarbonate solution (22.7 ml) was stirred for 2 hours at 40° C. The resultant solution was washed with ethyl acetate and acidified with 2 N hydrochloric acid to a pH 1 under ice-cooling, and the formed precipitate was separated by filtration to give 0.82 g of the objective compound.

Melting point: 279.3° C. (decomposition)

IR, (KBr, $cm^{-1}$): 3220, 1751, 1663, 1376, 1172

NMR (DMSO-$d_6$, ppm): 4.54 (2H, s), 7.02 (1H, s), 7.95–8.61 (3H, m), 11.63 (1H, bs)

EXAMPLE 61

Preparation of
1-(benzothiazol-2-ylsulfonyl)hydantoin (compound 22)

Step 1

Preparation of 2-benzylthiobertzothiazole

To a solution of 2-benzothiazolthlol (250 g) in N,N-dimethylformamide (1l) was added triethylamine (208 ml) under ice-cooling and dropwise a solution of benzyl bromide (178 ml) in N,N-dimethylformamide (300 ml) and the mixture was stirred for 40 minutes. The resulting solution was poured into water (10l) and the formed precipitate was separated by filtration and dissolved in dichloromethane (3 l). After drying over anhydorpus magnesium sulfate, dichloromethane was removed in vacuo to give 378 g of the objective compound.

Step 2

Preparation of benzothlazol-2-ylsulfonyl chloride

Into a mixture of 2-benzylthiobenzothiazole (100 g) and acetic acid (500 ml) in water (500 ml) was bubbled chlorine gas for 1.5 hours with stirring at −1:5° C. The resulting solution was poured into icewater (1.5 l), the formed precipitate was separated by filtration to give 90.9 g of the objective compound.

Step 3

Preparation of
N-(benzothiazol-2-ylsulfonyl)glycinamide

To a suspension of glycinamide hydrochloride (43 g) in dioxane (1 l) was added benzothiazol-2-ylsulfonyl chloride (90.9 g) under ice-cooling, and a pH of the mixture was adjusted to 8 with saturated aqueous sodium carbonate solution. After stirring for 1.5 hours, the resultant solution was concentrated in vacuo. Water (1.5 l) was added to the residue, and the solution was acidified with concentrated hydrochloric acid to pH 2. The formed precipitate was separated by filtration to give 59.8 g of the objective compound.

Melting point: 179.7°–181.8° C.

IR (KBr, $cm^{-1}$): 3426, 1682. 1345, 1165

NMR (DMSO-$d_6$, ppm): 3.73 (2H, s), 7.08 (1H, bs), 7.50 (1H, bs). 7.52–8.29 (4H, m), 8.80 (1H, bs)

Step 4

Preparation of N-(benzothiazol-2-ylsulfonyl)N-methoxycarbonylglycinamide

To a solution of the product obtained in Step 3 (102.3 g) in N,N-dimethylformamide 0.2l) was added slowly 60% sodium hydride (16.7 g) under ice-cooling, and the mixture was stirred for 1 hour at room temperature. Methyl chlorocarbonate (35.8 g) was added to the above-mentioned mixture followed by stirring for 1 hour at room temperature. After removing the solvent, water (3.5 l) was added to the residue, and the formed precipitate was separated by filtration to give 60.5 g of the objective compound.

Melting point: 153.1° C. (decomposition)

IR (KBr, $cm^{-1}$): 3459, 3346, 1737, 1689, 1386, 1343, 1250, 1171

NMR (DMSO-$d_6$, ppm): 3.10 (3H, s), 4.51 (2H, s), 7.30 (1H, bs), 7.60–7.76 (3H, m), 8.20–8.39 (2H, m)

Step 5

Preparation of
1-(benzothiazol-2-ylsulfonyl)hydantoin

To a solution of the product obtained in Step 4 (20.0 g) in N,N-dimethylformamide (200 ml) added slowly 60% sodium hydride (2.67 g), and the mixture was stirred for 13.5 hours at 70° C. After removing the solvent, water (1) was added to the residue, and the solution was extracted with ethyl acetate (1.5 l). The organic layer was washed with saturated aqueous NaCl solution, and dried over anhydrous sodium sulfate. Ethyl acetate was removed in vacuo, and the residue was washed with acetone-chloroform ( 100 ml+ 200 ml) to give 2.12 g of the objective compound.

Melting point: 260.4°–261 9° C.

IR (KBr, $cm^{-1}$): 3200, 3105, 1739, 1393, 1355, 1173

NMR (DMSO-$d_6$, ppm): 4.55 (2H, s), 7.61–7.81 (2H, m), 8.18–8.40 (2H, m). 11.88 (1H, bs)

EXAMPLE 62

Preparation of
1-(benzo[c]thiophen-1-ylsulfonyl)hydantoin

Step 1

Preparation of
$N^2$-(benzo[c]thiophen-1-ylsulfonyl)glycinamide

To a solution ot benzo[c]thiophen (5.5 g) in anhydrous ether (50 ml) was added 1.6 M solution of n-butyllithium in hexane (52.2 ml) at −20° C. under nitrogen atmosphere. After stirring for 1 hour, into the solution was bubbled sulfur dioxide for 1 hour with stirring at −20° C. Ether was removed in vacuo and the residue was suspended in isopropanol (200 ml) and water (200 ml). To the suspension was added N-chlorosuccinimide (6.5 g) at 0° C. After stirring for 30 minutes at 0° C., N-chlorosuccinimide (1.63 g) was added and the mixture was stirred for additional 1 hour. The resulting solution was extracted with dichloromethane (1 l×2) and the organic layer was washed with successive water and saturated aqueous NaCl solution. After drying over anhydrous sodium sulfate, dichloromcthane was removed in vacuo under cooling. Using this residue and glycinamide hydrochloride, the objective compound was obtained in a manner similar to Step 3 of Example 50.

NMR (DMSO-$d_6$, ppm): 3.40 (2H, d, J=6.9 Hz), 7.06–8.22 (5H, m), 8.49 (1H, s)

Step 2

Preparation of N-(benzo[c]thiophen-1-ylsulfonyl)-N 2-methoxycarbonylglycinamide

To a solution of the product obtained in Step 1 (0.45 g) in N,N-dimethylformamide (5 ml) was added slowly (60% sodium hydride (75 mg) under ice-oooling, and the mixture was stirred for 30 minutes at room temperature. Methyl chloroformate (0.14 ml) was added to the above-mentioned mixture followed by stirring for 20 minutes at room temperature. 60% sodium hydride (75 mg) was added to the solution, and the mixture was stirred for 1.5 hours at room temperature, then 15 minutes at 70° C. After cooling to room temperature, water (20 ml) was added to the resultant mixture and this aqueous solution was extracted with ethyl acetate (20 ml×3). The organic layer was washed with water, then saturated aqueous NaCl solution. After drying over anhydrous magnesium sulfate, ethyl acetate was removed in vacuo and the residue was purified by silica-gel columun chromatography to give 0.18 g of the objective compound.

NMR ($CDCl_3$, ppm): 3.74 (3H, s), 4.24 (2H, d, J=5.3 Hz), 5.92 (1H, t, J=5.3 Hz), 7.17–8.31 (6H, m)

Step 3

Preparation of 1-(bennzo[c]thiophen-1-ylsulfonyl)hydantoin

To a solution of the product obtained in Step 2 (0.18 g) in N,N-dimethylformamide (3 ml) added slowly 60% sodium hydride (48 mg), and the mixture was stirred for 2.5 hours at 70° C. After removing the solvent, ice water (20 ml) was added to the residue, and pH of the solution was adjusted to 4 with 1 N hydrochloric acid. The resultant solution was extracted with ethyl acetate (20 ml×3), and the organic layer was washed with saturated aqueous NaCl solution, and dried over anhydrous magnesium sulfate. Ethyl acetate was removed in vacuo, and the residue was triturated with dichloromethane to give 0.03 g of the objective compound.

Melting point: 223.6°–226.9° C.

IR (KBr, $cm^{-1}$): 1736, 1378, 1185, 1162, 1152

NMR (DMSO-$d_6$, ppm): 4.51 (2H, s), 7.20–8.16 (4H, m)8.82 (1H, s), 11.54 (1H, bs)

Intermediate compounds of Example 6 to 25, 28 to 52, 54 and 55 are summarized to the following table 6 and 7 together with corresponding IR and NMR data and melting points.

TABLE 6

$Q-SO_2NHCH_2CO_2H$

| Ex. No. | Q | IR(KBr, $cm^{-1}$) | NMR(DMSO-$d_6$, ppm) | M.P. (°C.) |
|---|---|---|---|---|
| 6 | 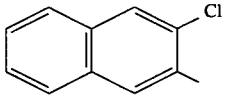 | 3345, 1710, 1315, 1140 | 3.69(2H, d), 7.61~8.37(6H, m), 8.49(1H, s) | 174.5~182.1 |
| 7 | 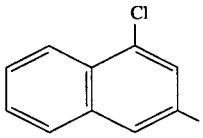 | | 3.70(2H, d, J=5.9Hz), 7.72~8.50(7H, m) | 185.2~186.4 |
| 8 | 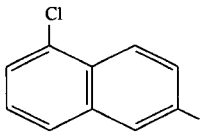 | | 3.44(2H, s), 7.52~8.60(7H, m) | >300 |
| 9 | 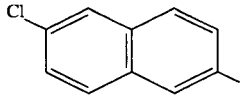 | 3350, 1715, 1320, 1145 | 3.55(2H, d, J=5.8Hz), 7.51~8.30(6H, m), 8.48(1H, s) | 158.8~165.7 |
| 10 | 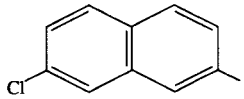 | | 3.73(2H, s), 7.51~8.53(7H, m) | 247.8~254.7 |
| 11 | 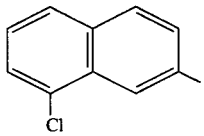 | | 3.69(2H, d, J=6.0Hz), 7.58~8.71(7H, m) | 157.8~162.1 |
| 12 | 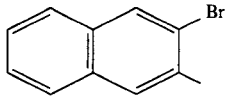 | 3345, 1715 1330, 1165 | 3.78(2H, d, J=5.9Hz), 7.61~8.22(5H, m), 8.42(1H, s), 8.64(1H, s) | 210.0~214.4 |

TABLE 6-continued
| Ex. No. | Q — $SO_2NHCH_2CO_2H$ | IR(KBr, $cm^{-1}$) | NMR(DMSO-$d_6$, ppm) | M.P. (°C.) |
|---|---|---|---|---|
| 13 | 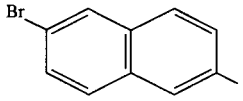 | 3350, 1715, 1320, 1145 | 3.48(2H, s), 7.52~8.48(7H, m) | 257.2~265.7 |
| 14 | 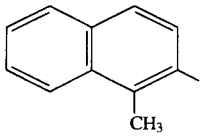 | | 2.98(3H, s), 3.62(2H, d, J=5.9Hz), 7.52~8.35(7H, m) | 179.0~182.7 |
| 15 | 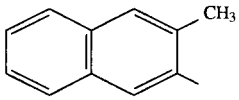 | | 2.79(3H, s), 3.73(2H, d, J=6.1Hz), 7.43~8.35(6H, m), 8.53(1H, s) | 155.5~160.5 |
| 16 | 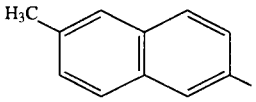 | | 2.49(3H, s), 3.40(2H, s), 7.35~8.39(7H, m) | 225.7~230.6 |
| 17 | 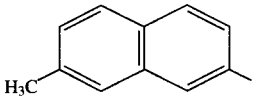 | | 2.49(3H, s), 3.65(2H, s), 7.35~8.45(7H, m) | 147.4~152.0 |
| 18 | 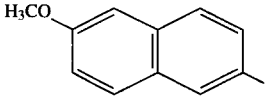 | 3340, 1710, 1325, 1155 | 3.62(2H, d, J=6.0Hz), 3.91(3H, s), 7.19~8.15(6H, m), 8.31(1H, s) | 161.4~163.6 |
| 19 | 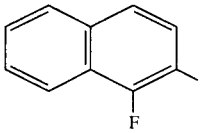 | | 3.78(2H, d, J=5.9Hz), 7.67~8.45(7H, m) | 163.5~168.5 |
| 20 | 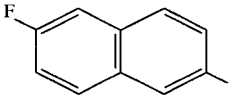 | | 3.62(2H, s), 7.05~8.50(7H, m) | 109.0~109.5 |
| 21 | 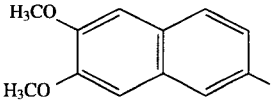 | | 3.55(2H, s), 3.93(6H, s), 7.35~7.98(5H, m), 8.24(1H, s) | 212.6~217.1 |
| 22 | 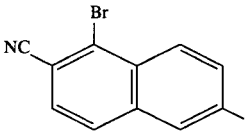 | 3280, 2230, 1760, 1155 | 3.71(2H, d, J=6.0Hz), 7.87~8.65(6H, m) | 231.9~234.9 |
| 23 | 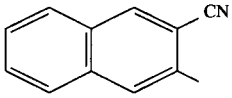 | 3260, 2240, 1740, 1155 | 3.69(2H, d, J=6.0Hz), 7.82~8.73(7H, m) | 186.2~192.0 |
| 24 | 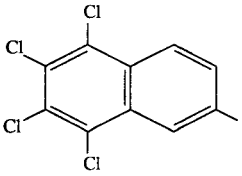 | | 3.72(2H, d, J=5.7Hz), 8.09~8.68(4H, m) | 258.8~261.5 |

TABLE 6-continued
| Ex. No. | Q | IR(KBr, $cm^{-1}$) | NMR(DMSO-$d_6$, ppm) | M.P. (°C.) |
|---|---|---|---|---|
| | $Q-SO_2NHCH_2CO_2H$ | | | |
| 25 | 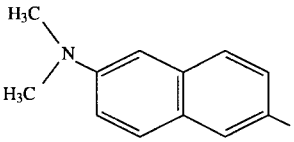 | | 3.06(6H, s), 3.55(2H, d, J=6.0Hz), 6.91~8.21(7H, m) | 148.0~152.0 |
| 28 | 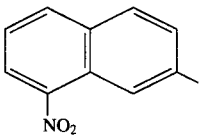 | 3348, 1710, 1518, 1334, 1142 | 3.68(2H, d, J=6.3Hz), 7.78~8.89(7H, m), 12.63(1H, bs) | 224.9~227.7 |
| 29 | 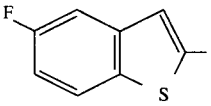 | 3290, 1709, 1342, 1156 | 3.73(2H, d, J=5.9Hz), 7.31~8.22(4H, m), 8.59(1H, t, J=5.9Hz), 12.72(1H, bs) | 162.7~164.2 |
| 30 | 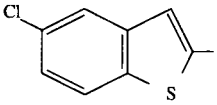 | 3295, 1709, 1343, 1156 | 3.73(2H, d, J=5.9Hz), 7.49~8.17(4H, m), 8.59(1H, t, J=5.9Hz), 12.54(1H, bs) | 186.9~189.1 |
| 31 | 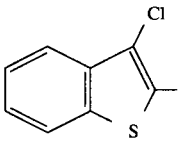 | 3337, 1716, 1342, 1257, 1162 | 3.83(2H, d, J=6.3Hz), 7.52~8.24(4H, m), 8.87(1H, t, J=6.3Hz), 12.63(1H, bs) | 156.6~161.0 |
| 32 | 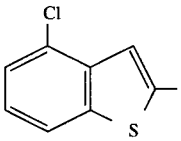 | 3255, 1710, 1356, 1248, 1160 | 3.78(2H, d, J=5.9Hz), 7.44~8.13(4H, m), 8.66(1H, t, J=5.9Hz), 12.68(1H, bs) | 197.0~199.2 |
| 33 | 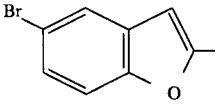 | 3334, 1717, 1437, 1352, 1241, 1152 | 3.78(2H, s), 7.49(1H, s), 7.68(2H, s), 8.00(1H, s), 8.83(1H, bs) | 192.4~194.1 |
| 34 | 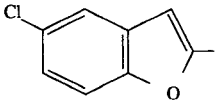 | 3377, 1718, 1358, 1247, 1157 | 3.76(2H, s), 7.44~7.89(4H, m) | 191.5~193.8 |
| 35 | 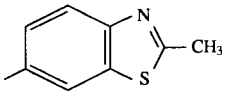 | 3290, 1720, 1340, 1170 | 2.86(3H, s), 3.63(2H, d, J=6.3Hz), 7.79~8.54(4H, m), 12.48(1H, bs) | 237.7 (dec.) |
| 36 | 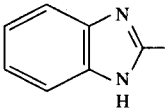 | 3068, 1718, 1617, 1349, 1155 | 3.78(2H, s), 7.25~7.70(4H, m) | 133.5~135.9 |
| 37 | 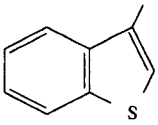 | 3318, 1724, 1339, 1241, 1152 | 3.64(2H, d, J=5.9Hz), 7.36~7.60(2H, m), 7.97~8.45(4H, m) | |
| 38 | 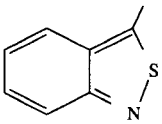 | 3094, 1721, 1358, 1164 | 3.82(2H, s), 7.43~8.17(4H, m), 9.09(1H, bs), 12.51(1H, bs) | 212.5~214.4 |

TABLE 6-continued
| Ex. No. | Q | IR(KBr, $cm^{-1}$) | NMR(DMSO-$d_6$, ppm) | M.P. (°C.) |
|---|---|---|---|---|
| | $Q-SO_2NHCH_2CO_2H$ | | | |
| 39 | 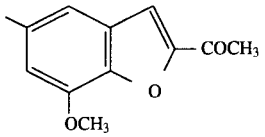 | 3290, 1733, 1655, 1331, 1158 | 2.58(3H, s), 3.61(2H, d, J=5.9Hz), 4.03(3H, s), 7.49~8.17(4H, m), 12.50(1H, bs) | 215.0~217.6 |
| 41 | 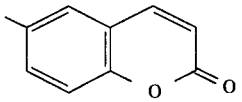 | 3265, 1748, 1711, 1316, 1205, 1154 | 3.65(2H, d, J=5.9Hz), 6.62(1H, d, J=9.9Hz), 7.57(1H, d, J=8.6Hz), 7.92~8.25(4H, m), 12.69(1H, bs) | 235.0 (dec) |
| 42 | 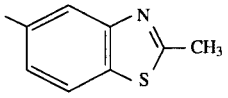 | 3302, 1727, 1330, 1216, 1154 | 2.85(3H, s), 3.63(2H, d, J=5.9Hz), 7.73~8.29(4H, m) | 257.2 (dec.) |
| 43 | 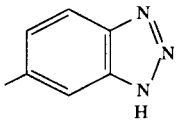 | 3213, 1718, 1317, 1255, 1164, 1153 | 3.64(2H, d, J=5.6Hz), 7.78~8.38(4H, m) | 243.5~245.3 |
| 44 | 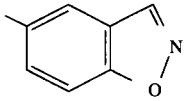 | 3271, 1742, 1316, 1149 | 3.64(2H, d, J=6.3Hz), 7.90~8.63(4H, m), 9.38(1H, s), 12.57(1H, bs) | 165.3~168.5 |
| 45 | 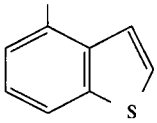 | 3097, 1741, 1316, 1209, 1148 | 3.57(2H, d, J=5.9(Hz), 7.39~8.33(6H, m) | |
| 46 | 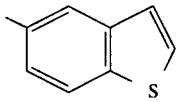 | 3186, 1765, 1751, 1732, 1335, 1145 | 3.60(2H, d, J=6.3Hz), 7.61~8.35(6H, m), 12.58(1H, bs) | |
| 47 | 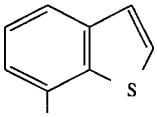 | 3282, 1727, 1309, 1161, 1137 | 3.65(2H, d, J=5.9Hz), 7.47~8.18(5H, m), 8.33(1H, t, J=5.9Hz), 12.64(1H, bs) | |
| 48 | 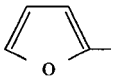 | 3307, 1725, 1340, 1329, 1157 | 3.66(2H, d, J=6.3Hz), 6.58~7.90(3H, m), 8.38(1H, t, J=6.3(Hz), 12.63(1H, bs) | |
| 49 | 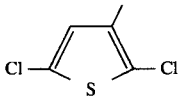 | 3358, 1728, 1348, 1236, 1166 | 3.76(2H, d, J=5.9Hz), 7.28(1H, s), 8.45(1H, t, J=5.9Hz), 12.76(1H, bs) | |
| 50 | 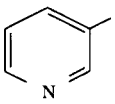 | 3236, 1701, 1341, 1174 | 3.70(2H, d, J=5.9Hz), 7.54~8.24(2H, m), 8.33(1H, t, J=5.9Hz), 8.76~8.96(2H, m), 12.70(1H, bs) | 220.4~223.8 |
| 51 | $CH_3-$ | 3258, 1711, 1320, 1247, 1148 | 2.92(3H, s), 3.72(2H, d, J=5.9Hz), 7.39(1H, t, J=5.9Hz), 12.71(1H, bs) | 168.0~171.0 |
| 52 | 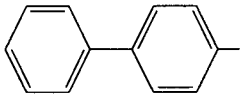 | 3348, 1714, 1323, 1152 | 3.62(2H, d, J=6.3Hz), 7.44~7.87(9H, m), 8.06(1H, t, J=6.3Hz) | |

TABLE 6-continued
| Ex. No. | Q | IR(KBr, $cm^{-1}$) | NMR(DMSO-$d_6$, ppm) | M.P. (°C.) |
|---|---|---|---|---|
| | $Q-SO_2NHCH_2CO_2H$ | | | |
| 54 | 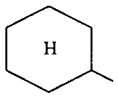 | 3308, 1714, 1319, 1147, 1126 | 1.18~2.06(10H, m), 2.64~3.19(1H, m), 3.69(2H, d, J=6.0Hz), 7.33(1H, t, J=6.0Hz) | 96.0~100.9 |
| 55 | 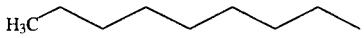 | 3314, 3256, 2921, 1716, 1313, 1141 | 0.80~1.86(15H, m), 2.91~3.09(2H, m), 3.70(2H, d, J=5.9Hz), 7.39(1H, t, J=5.9Hz), 12.69(1H, bs) | |
TABLE 7
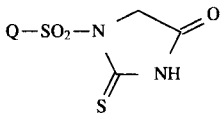
| Ex. No. | Q | IR(KBr, $cm^{-1}$) | NMR(DMSO-$d_6$, ppm) | H.P. (°C.) |
|---|---|---|---|---|
| 6 | 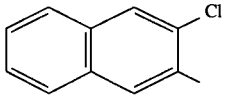 | 3130, 1785, 1760, 1165 | 4.90(2H, s), 7.69~8.45(5H, m), 8.88(1H, s) | 212.9~222.8 |
| 7 | 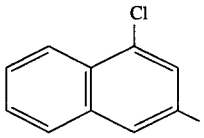 | | 4.88(2H, s), 7.74~8.83(6H, m) | 250.1 (dec.) |
| 8 | 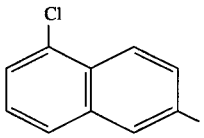 | | 4.89(2H, s), 7.59~8.43(5H, m), 8.70~8.96(1H, m) | 231.4 (dec.) |
| 9 | 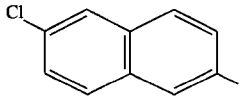 | 3150, 1795, 1770, 1170 | 4.93(2H, s), 7.61~8.35(5H, m), 8.89(1H, s) | 211.4~221.9 |
| 10 | 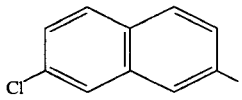 | | 4.88(2H, s), 7.68~8.39(5H, m), 8.80(1H, s) | 227.8 (dec.) |
| 11 | 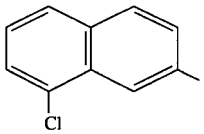 | | 4.89(2H, s), 7.60~8.29(5H, m), 8.69~8.87(1H, m) | 190.5 (dec.) |
| 12 | 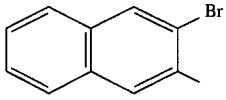 | 3270, 1795, 1770, 1170 | 4.94(2H, s), 7.65~8.51(5H, m), 8.99(1H, s) | 248.5~255.7 |
| 13 | 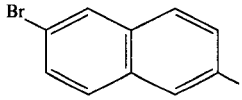 | 3120, 1785, 1755, 1165 | 4.85(2H, s), 7.70~8.40(5H, m), 8.67~8.84(1H, m) | 198.5~209.5 |

TABLE 7-continued
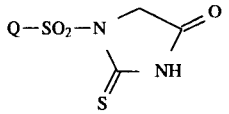
| Ex. No. | Q | IR(KBr, $cm^{-1}$) | NMR(DMSO-$d_6$, ppm) | H.P. (°C.) |
|---|---|---|---|---|
| 14 | 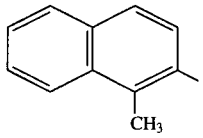 | | 2.97(3H, s), 4.86(2H, s), 7.55~8.47(6H, m) | 243.9 (dec.) |
| 15 | 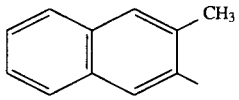 | | 2.64(3H, s), 4.80(2H, s), 7.47~8.26(5H, m), 8.81(1H, s) | 242.0~244.7 |
| 16 | 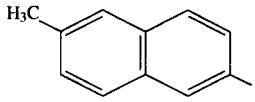 | | 2.53(3H, s), 4.91(2H, s), 7.45~8.68(5H, m), 8.70(1H, s) | 234.8~237.6 |
| 17 | 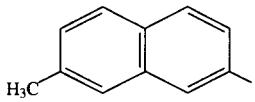 | | 2.52(3H, s), 4.71(2H, s), 7.29~8.03(5H, m), 8.58~8.69(1H, m) | 232.7~238.2 |
| 18 | 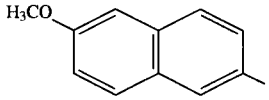 | 3250, 1790, 1755, 1165 | 3.94(3H, s), 4.85(2H, s), 7.23~7.51(2H, m), 7.87~8.17(3H, m), 8.67(1H, s) | 236.4 (dec.) |
| 19 | 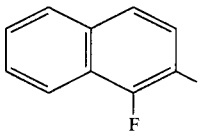 | | 4.82(2H, s), 7.67~8.33(6H, m) | 248.0 (dec.) |
| 20 | 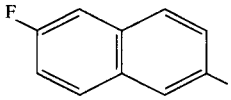 | | 4.86(2H, s), 7.23~8.61(6H, m) | 177.1~184.7 |
| 21 | 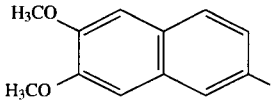 | | 3.95(6H, s), 4.86(2H, s), 7.45~7.97(4H, m), 8.45~8.59(1H, m) | 260.7 (dec.) |
| 22 | 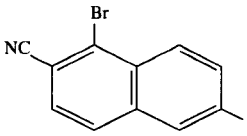 | 2230, 1760, 1350, 1170 | 4.88(2H, s), 7.88~8.55(4H, m), 8.73~9.00(1H, m) | 223.9 (dec.) |
| 23 | 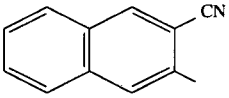 | 2225, 1760, 1350, 1170 | 4.88(2H, s), 7.81~8.46(4H, m), 8.64~8.92(2H, m), 12.60(1H, bs) | 131.0~135.8 |
| 24 | 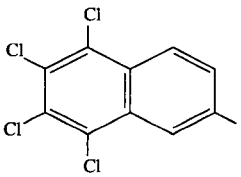 | | 4.86(2H, s), 8.46~8.99(3H, m), 12.60(1H, bs) | 270.0 (dec.) |

TABLE 7-continued
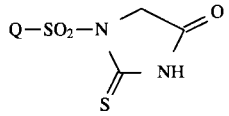
| Ex. No. | Q | IR(KBr, $cm^{-1}$) | NMR(DMSO-$d_6$, ppm) | H.P. (°C.) |
|---|---|---|---|---|
| 25 | 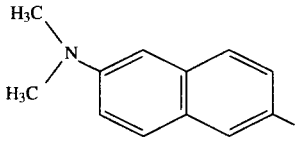 | | 3.10(6H, s), 4.82(2H, s), 6.93~8.03(5H, m), 8.47(1H, s) | 256.4 (dec.) |
| 28 | 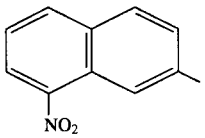 | 1793, 1764, 1527, 1345 1172 | 4.85(2H, s), 7.80~9.24(6H, m), 12.67(1H, bs) | 229.6 (dec.) |
| 29 | 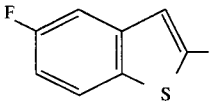 | 1757, 1391, 1253, 1176 | 4.74(2H, s), 7.41~8.50(4H, m), 12.76(1H, bs) | 240.4~ 242.5 |
| 30 | 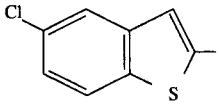 | 1761, 1468, 1385, 1249, 1170 | 4.73(2H, s), 7.50~8.46(4H, m), 12.77(1H, bs) | 208.3 (dec.) |
| 31 | 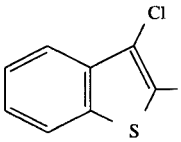 | 1784, 1756, 1462, 1374, 1245, 1173 | 4.92(2H, s), 7.50~8.34(4H, m), 12.95(1H, bs) | 275.3 (dec.) |
| 32 | 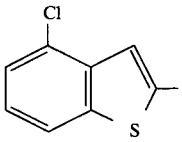 | 1746, 1467, 1382, 1257, 1171 | 4.79(2H, s), 7.53~8.40(4H, m), 12.76(1H, bs) | 221.2~ 224.6 |
| 33 | 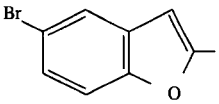 | 1751, 1436, 1392, 1237, 1165 | 4.74(2H, s), 7.65~8.10(4H, m), 12.72(1H, bs) | 186.7~ 187.7 |
| 34 | 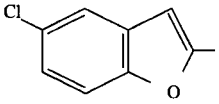 | 1750, 1458, 1394, 1164 | 4.74(2H, s), 7.50~8.07(4H, m), 12.83(1H, bs) | 213.9 (dec.) |
| 35 | 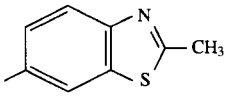 | 1748, 1378, 1245, 1175 | 2.88(3H, s), 4.83(2H, s), 8.13(2H, s), 8.87(1H, s), 12.62(1H, bs) | 240.4 (dec.) |
| 36 | 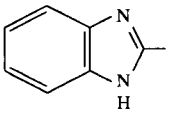 | 1785, 1758, 1449, 1388, 1255, 1185, 1160 | 4.84(2H, s), 7.26~7.86(4H, m), 12.94(1H, bs) | |
| 37 | 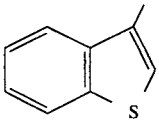 | 3111, 1793, 1762, 1463, 1374, 1174 | 4.87(2H, s); 7.47~7.68(2H, m), 8.04~8.28(2H, m), 9.01(1H, s), 12.64(1H, bs) | |

TABLE 7-continued
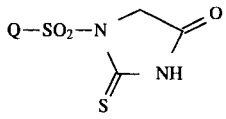
| Ex. No. | Q | IR(KBr, $cm^{-1}$) | NMR(DMSO-$d_6$, ppm) | H.P. (°C.) |
|---|---|---|---|---|
| 38 | 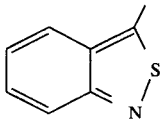 | 1757, 1386, 1167 | 4.83(2H, s), 7.50~8.34(4H, m), 12.77(1H, bs) | 203.1 (dec.) |
| 39 | 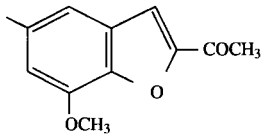 | 1764, 1680, 1475, 1361, 1319, 1162 | 2.59(3H, s), 4.08(3H, s), 4.77(2H, s), 7.50~8.28(3H, m), 12.51(1H, bs) | 244.0 (dec.) |
| 40 | 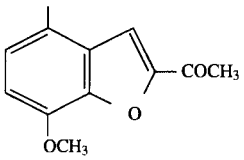 | 1746, 1671, 1362, 1305, 1186, 1167 | 2.63(3H, s), 4.10(3H, s), 4.85(2H, s), 7.32(1H, d, J=8.9Hz), 7.95(1H, s), 8.14(1H, d, J=8.9Hz), 12.54(1H, bs) | |
| 41 | 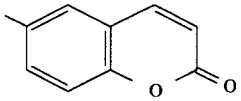 | 1745, 1467, 1385, 1360, 1170 | 4.81(2H, s), 6.65(1H, d, J=9.6Hz), 7.62(1H, d, J=8.9Hz), 8.04~8.58(3H, m), 12.66(1H, bs) | 230.2 (dec.) |
| 42 | 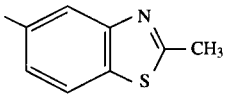 | 1762, 1613, 1370, 1241, 1174 | 2.87(3H, s), 4.85(2H, s), 7.92~8.64(3H, m), 12.61(1H, bs) | 226.0 (dec.) |
| 43 | 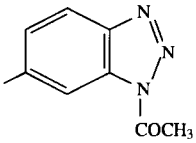 | 1755, 1459, 1380, 1169 | 2.96(3H, s), 4.89(2H, s), 8.41(2H, s), 9.06(1H, s), 12.60(1H, bs) | 222.7 (dec.) |
| 44 | 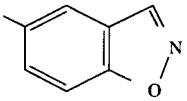 | 1759, 1459, 1370, 1243, 1189, 1162 | 4.83(2H, s), 7.99~8.75(3H, m), 9.46(1H, s), 12.64(1H, bs) | 264.0 (dec.) |
| 45 | 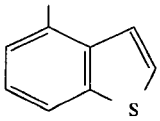 | 1745, 1476, 1362, 1267, 1199, 1170 | 4.90(2H, s), 7.46~8.55(5H, m), 12.63(1H, bs) | |
| 46 | 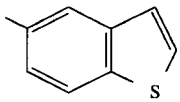 | 1755, 1474, 1364, 1256, 1200, 1169 | 4.84(2H, s), 7.50~8.73(5H, m), 12.58(1H, bs) | |
| 47 | 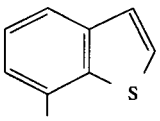 | 1743, 1459, 1390, 1346, 1172 | 4.91(2H, s), 7.55~8.31(5H, m), 12.71(1H, bs) | |
| 48 | 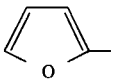 | 1753, 1431, 1381, 1191, 1166 | 4.68(2H, s), 6.72~6.86(1H, m), 7.54(1H, d, J=3.6Hz), 8.10(1H, d, J=1.8Hz), 12.75(1H, bs) | |

TABLE 7-continued

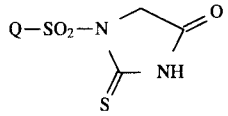

| Ex. No. | Q | IR(KBr, $cm^{-1}$) | NMR(DMSO-$d_6$, ppm) | H.P. (°C.) |
|---|---|---|---|---|
| 49 | 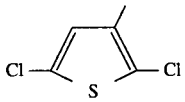 | 1795, 1758, 1452, 1432, 1374, 1177 | 4.77(2H, s), 7.65(1H, s), 12.85(1H, bs) | |
| 50 | 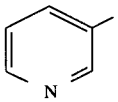 | 1788, 1755, 1378, 1263, 1173 | 4.82(2H, s), 7.62~9.22(4H, m), 12.69(1H, bs) | 221.0 (dec.) |
| 51 | $CH_3-$ | 1745, 1470, 1424, 1361, 1165 | 3.57(3H, s), 4.52(2H, s), 12.70(1H, bs) | 213.4~216.0 |
| 52 | 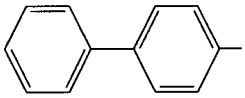 | 1743, 1456, 1374, 1171 | 4.84(2H, s), 7.47~8.23(9H, m), 12.65(1H, bs) | |
| 54 | 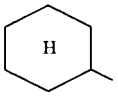 | 1791, 1757, 1735, 1453, 1353, 1236, 1169 | 1.24~2.23(10H, m), 3.90~4.32(1H, m), 4.50(2H, s), 12.70(1H, bs) | |
| 55 | 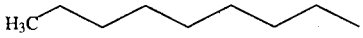 | 1748, 1735, 1454, 1363, 1235, 1157 | 0.54~2.04(15H, m), 3.60~4.02(2H, m), 4.51(2H, s), 12.68(1H, bs) | |

Now, typical but non-limiting examples of formulations of the compound of this invention will be shown below.

Formulation A (Capsules)

Compound 13, 300 g of weight, 685 g of lactose and 15 g of magnesium stearate were weighed and mixed until the mixture became homogeneous. The mixture was then filled in No. 1 hard gelatin capsule at 200 mg each to obtain capsule preparation.

Formulation B (Tablets)

Compound 15, 300 g of weight, 550 g of lactose, 120 g of potato starch. 15 g of polyvinyl alcohol and 15 g of magnesium stearate were weighed. The weighed amount of compound 15, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation C (Powder)

Compound 8, 200 g of weight, 790 g of lactose and 10 g of magnesium stearate were weighed and mixed until the mixture became homogeneous to obtain 20% powder preparation.

Formulation D (Capsules)

Compound 16, 300 g of weight, 685 g of lactose and 15 g of magnesium stearate were weighed and mixed until the mixture became homogeneous. The mixture was then filled in No. 1 hard gelatin capsule at 200 mg each to obtain capsule preparation.

Formulation E (Tablets)

Compound 19, 300 g of weight, 550 g of lactose, 120 g of potato starch, 15 g of polyvinyl alcohol and 15 g of magnesium stearate were weighed. The weighed amount of compound 19, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Compounds of Example 63 to 77 prepared in a manner similar to Example 26 are summarized in the following table 8 together with corresponding IR and NMR data and melting points.

TABLE 8
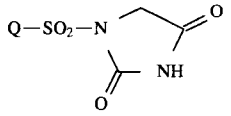
| Ex. No. | Q | IR(KBr, $cm^{-1}$) | NMR(DMSO-$d_6$, ppm) | M.P. (°C.) |
|---|---|---|---|---|
| 63 | 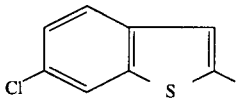 | 1800, 1750, 1739, 1381, 1160 | 4.46(2H, s), 7.57(1H, dd, J=8.6, 1.7Hz), 8.11(1H, d, J=8.6Hz), 8.33(2H, s) | 249.1~251.3 |
| 64 | 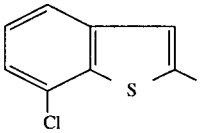 | 3096, 1786, 1734, 1376, 1166 | 4.48(2H, s), 7.50~7.81(1H, m), 8.11(1H, dd, J=6.6, 1.3Hz), 8.44(1H, s), 11.74(1H, bs) | 285.0 (dec.) |
| 65 | 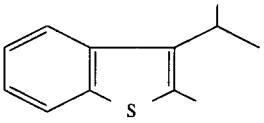 | 3210, 1809, 1728, 1392 1160 | 1.46(6H, d, J=7.3Hz), 3.96~4.28(1H, m), 4.52(2H, s), 7.48~7.67(2H, m), 8.07~8.32(2H, m), 11.76(1H, bs) | 174.1~176.6 |
| 66 | 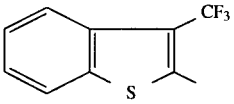 | 1733, 1379, 1180 | 4.53(2H, s), 7.66~8.38(4H, m), 11.95(1H, bs) | 243.2 (dec.) |
| 67 | 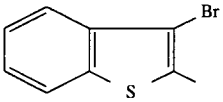 | 3160, 1805, 1725, 1379, 1183 | 4.70(2H, s), 7.57~8.28(4H, m), 11.86(1H, bs) | 288.0~289.5 |
| 68 | 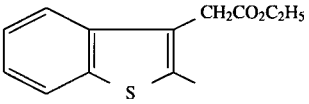 | 1804, 1744, 1378, 1178 | 1.16(3H, t, J=7.0Hz), 4.07(2H, q, J=7.0Hz), 4.42(2H, s), 4.47(2H, s), 7.53~7.66(2H, m), 7.99~8.20(2H, m), 11.73(1H, bs) | 196.0~197.5 |
| 69 | 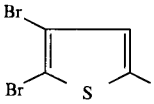 | 3300, 1779, 1729, 1382, 1173, 1167 | 4.44(2H, s), 7.95(1H, s), 11.75(1H, bs) | 283.2 (dec.) |
| 70 | 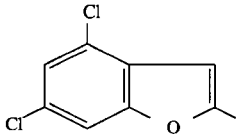 | 3270, 1807, 1742, 1389, 1169 | 4.45(2H, s), 7.72(1H, d, J=1.6Hz), 7.96(1H, d, J=1.0Hz), 8.07(1H, dd, J=1.6, 1.0Hz), 11.78(1H, bs) | 290.8 (dec.) |
| 71 | 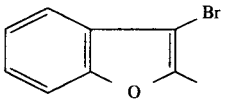 | 3220, 1800, 1783, 1397, 1176, 1154 | 4.52(2H, s), 7.43~7.91(4H, m) | 265.7~267.9 |
| 72 | 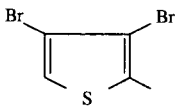 | 3080, 1805, 1725, 1378, 1187, 1177 | 4.62(2H, s), 8.40(1H, s), 11.84(1H, bs) | 278.0 (dec.) |
| 73 | 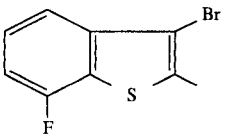 | 3209, 3177, 1812, 1726, 1490, 1379, 1305, 1176, 1162 | 4.69(2H, s), 7.51~7.90(3H, m), 11.90(1H, bs) | 286.0 (dec.) |

TABLE 8-continued

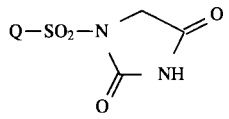

| Ex. No. | Q | IR(KBr, $cm^{-1}$) | NMR(DMSO-$d_6$, ppm) | M.P. (°C.) |
|---|---|---|---|---|
| 74 | 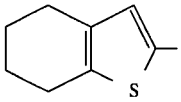 | 3210, 1806, 1735, 1364, 1158. | 1.62~1.92(4H, m), 2.46~2.91(4H, m), 4.40(2H, s), 7.60(1H, s), 11.61(1H, bs) | 248.3~249.5 |
| 75 | 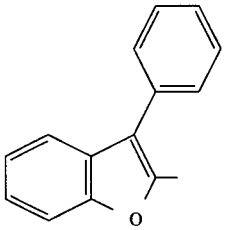 | 1810, 1793, 1396, 1177 | 4.34(2H, s), 7.43~7.88(9H, rc), 11.76(1H, bs) | 220.4 (dec.) |
| 76 | 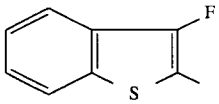 | 3230, 1742, 1389, 1183 | 4.47(2H, s), 7.53~8.13(4H, m), 11.72(1H, bs) | 256.0~258.0 |
| 77 | 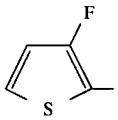 | 3103, 1805, 1787, 1729, 1534, 1426, 1383, 1366, 1169 | 4.41(2H, s), 7.21(1H, d, J=5.6Hz), 8.12(1H, dd, J=5.6, 4.3Hz), 11.73(1H, bs) | 238.2~240.9 |

Compounds of Example 78 to 81 prepared in a manner similar to Example 53 are summarized in the following table 9 together with corresponding IR and NMR data and melting points.

TABLE 9

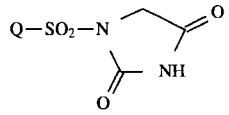

| Ex. No. | Q | IR(KBr, $cm^{-1}$) | NMR(DMSO-$d_6$, ppm) | M.P. (°C.) |
|---|---|---|---|---|
| 78 | 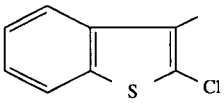 | 3170, 1787, 1732, 1365, 1171 | 4.61(2H, s), 7.50~7.61(2H, m), 8.04~8.26(2H, m), 11.72(1H, bs) | 215.0~219.0 |
| 79 | 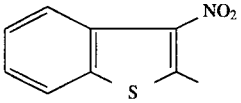 | 3214, 1778, 1725, 1528, 1439, 1346 | 4.53(2H, s), 7.49~7.68(2H, m), 8.03~8.17(2H, m), 11.87(1H, bs) | 221.1~223.2 |
| 80 | 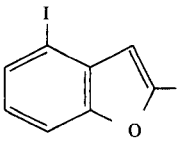 | 1810, 1742, 1391, 1165, 1139 | 4.48(2H, s), 7.28~7.89(4H, m), 11.61(1H, bs) | 277.0 (dec.) |

TABLE 9-continued

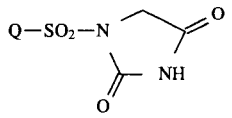

| Ex. No. | Q | IR(KBr, $cm^{-1}$) | NMR(DMSO-$d_6$, ppm) | M.P. (°C.) |
|---|---|---|---|---|
| 81 | 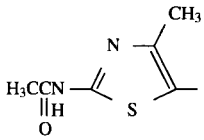 | 3190, 3040, 1795, 1750, 1372, 1170 | 2.19(3H, s), 2.54(3H, s), 4.41(2H, s), 11.61(1H, bs), 12.73(1H, bs) | >300 |

Compounds of Example 82 and 83 prepared in a manner similar to Example 61 are summarized in the following table 10 together with corresponding IR and NMR data and melting points.

TABLE 10

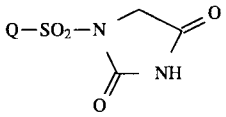

| Ex. No. | Q | IR(KBr, $cm^{-1}$) | NMR(DMSO-$d_6$, ppm) | M.P. (°C.) |
|---|---|---|---|---|
| 82 | 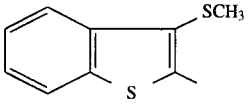 | 3200, 1801, 1724, 1374, 1180 | 2.47(3H, s), 4.77(2H, s), 7.60~7.76(2H, m), 8.09~8.25(2H, m), 11.83(1H, bs) | 213.2~222.0 |
| 83 | 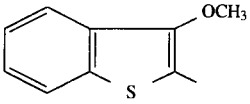 | 3240, 1990, 1728, 1371, 1163 | 4.18(3H, s), 4.55(2H, s), 7.55~7.66(2H, m), 8.06~8.14(2H, m), 11.70(1H, bs) | 239.7~241.3 |

EXAMPLE 84

Preparation of 1-(3-carboxymethylbenzo[b]thiophen-2-ylsulfonyl)hydantoin

A mixture of the product obtained in Step 4 of Example 68 (0.85 g) and 60% (w/v) nitric acid (9 ml) was heated with stirring for 140 minutes at 70° C. After cooling to room temperature, the formed precipitate was separated by filtration and washed with ether to give 0.21 g of the objective compound.

Melting point: 224.4° C. (decomposition)

IR (KBr $cm^{-1}$): 3220, 1800, 1736, 1718, 1374, 1170

NMR (DMSO-$d_6$, ppm): 4.32 (2H, s), 4.47 (2H, s), 7.55–7.65 (2H, m), 7.99–8.19 (2H, m), 11.71 (1H, bs)

EXAMPLE 85

Preparation of 1-(3-methylsulfinylbenzo[b]thiophen-2-ylsulfonyl)hydamtoin

To a suspension of the product obtained in Example 82 (0.65 g) in dichloromethanc (26 ml) was added m-chloroperbenzoic acid (0.41 g) and the mixture was stirred for 1.5 hours at room temperature. The resulting solution was concentrated in vacuo and the residue was washed with ether (30 ml). The residue was purified by silica gel column chromatography to give 0.48 g of the objective compound.

Melting point: 215.0°–221.0° C.

IR (KBr, $cm^{-1}$): 1792, 1743, 1379, 1180

NMR (DMSO-$d_6$, ppm): 3.10 (3H, s), 4.57 (2H, S), 7.51–8.89 (4H, m), 11.81 (1H, bs)

EXAMPLE 86

Preparation of 1-(3-methylsulfonylbenzo[b]thiophen-2-ylsulfonyl)hydantoin (compound 32)

To a suspension of the product obtained in Example 82 (0.65 g) in ethyl acetate (26 ml) was added m-chloroperbenzoic acid (0.82 g) and the mixture was stirred under reflux for 1.5 hours. Additional m-chloroperbenzoic acid (0.16 g) was added and the mixture was stirred under reflux for more 1.5 hours. The resulting solution was concentrated in vacuo and the residue was washed with successive methanol and ether to give 0.40 g of the objective compound.

Melting point: 224.0°–245.0° C.

IR (KBr, $cm^{-1}$): 1771. 1372, 1324, 1179

NMR (DMSO-$d_6$, ppm): 3.47 (3H, s), 4.63 (2H, s), 7.66–8.59 (4H, m), 11.90 (1H, bs)

EXAMPLE 87

Preparation of 1-(3-cyanobenzo[b]thiophen-2-ylsulfonyl)hydantoin (compound 33)

To a mixture of the product obtained in Example 67 (11.3 g) and copper (I) cyanide (4.1 g) was added pyridine (42 ml). After stirring at 70° C. for 17 hours, a solution of Iron (III) chloride hexahydrate (15.7 g) in concentrated hydrochloric acid (3.9 ml) and water (23.6 ml) was added slowly to the solution and the resultant mixture was heated with stirring for 5 minutes at 50° C. The formed precipitate was separated by filtration and the filtrate was extracted with ethyl acetate (300 ml) and the organic layer was washed with successive water and saturated aqueous NaCl solution and dried over anhydrous sodium sulfate. Above mentioned precipitate was extracted by ethanol and this ethanol solution was combined with above mentioned organic layer. The resulting solution was concentrated in vacuo and purified by silica gel column chromatography to give 1.21 g of the objective compound.

Melting point: 238.9°–242.5° C.

IR (KBr, $cm^{-1}$): 2233, 1807, 1746, 1736, 1388, 1167

NMR (DMSO-$d_6$, ppm): 4.51 (2H, s), 7.70–8.47 (4H, m), 11.83 (1H, bs)

EXAMPLE 88

Preparation of 1-(3-hydroxybenzo[b]thlophen-2-ylsulfonyl)hydantoin

A mixture of the product obtained in Example 83 (2.5 g), acetic acid (7 ml) and 47% hydrobromic acid (8.9 ml) was stirred for 1 hour at room temperature and heated for 1 hour at 40° C., for more 1 hour at 50° C. To the mixture was added additional acetic acid (7 ml) and 47% hydrobromic acid (8.9 ml) and heated with stirring for 1 hour at 60° C., for 2 hours at 80° C. The resulting solution was poured into water (300 ml) and extracted with ethyl acetate (1.2 l). After drying over anhydrous magnesium sulfate, ethyl acetate was removed in vacuo and the residue was dissolved in acetone (800 ml). After decoloring with activated charcoal, acetone was removed in vacuo and the residue was washed with successive ethyl acetate and ether to give 1.13 g of the objective compound.

Melting point: 171.8° C. (decomposition)

IR (KBr, $cm^{-1}$): 3260, 1800, 1735, 1358, 1185, 1164

NMR (DMSO-$d_6$, ppm): 4.60 (2H, s), 7.46–8.19 (4H, m), 11.70 (1H, bs)

EXAMPLE 89

Preparation of 1-(3-carbamoylbenzo[b]thiophen-2-ylsulfonyl)hydantoin

A mixture of the product obtained in Example 87 (0.84 g) and 80% (v/v) sulfuric acid (16.3 ml) was heated with stirring for 8 hours at 70° C. and the resulting solution was poured into ice-water (200 ml). The formed precipitate was separated by filtration and washed with successive water, ethanol and acetone to give 0.16 g of the objective compound.

Melting point: 241.9°–244.6° C.

IR (KBr, $cm^{-1}$): 3412, 3197, 1795, 1741, 1376, 1162

NMR (DMSO-$d_6$, ppm): 4.51 (2H, s), 7.56–8.44 (6H, m), 11.73 (1H, bs)

EXAMPLE 90

Preparation of 1-(3-carboxybenzo[b]thiophen-2-ylsulfonyl)hydantoin

To a suspension of the product obtained in Example 89 (0.60 g) in concentrated sulfuric acid (18 ml) was added sodium nitrite (2.4 g) under cooling at −15° C. and the resulting suspension was stirred for 15 minutes at −15° C., for 30 minutes at 0° C. and for 50 minutes at room temperaiure. To the mixture was added additional sodium nitrite (1.2 g) and stirred for 30 minutes at room temperature. After adjusting a pH of the resulting solution to ca. 9 with 0.1 M sodium bicarbonate, the resulting solution was washed with ethyl acetate and acidified with concentrated hydrochloric acid to a pH about 2 and extracted with ethyl acetate (200 ml). The organic layer was washed with successive water and saturated aqueous NaCl solution. After drying over anhydrous sodium sulfate, ethyl acetate was removed in vacuo and the residue was purified by silica gel column chromatography to give 0.18 g of the objective compound.

Melting point: 228.8°–235.1° C.

IR (KBr, $cm^{-1}$): 3450, 1739, 1735, 1380, 1175

NMR (DMSO-$d_6$, ppm): 4.73 (2H, s), 7.45–8.17 (4H, m), 11.76 (1H, bs)

EXAMPLE 91

Preparation of 1-(3-chlorobenzo[b]furan-2-ylsulfonyl)hydantoin (compound 47)

Step 1

Preparation of 3-chlorobenzo[b]furan-2-yl-sulfonyl chloride

To a solution of 3-chlorobenzo[b]furan (11.4 g) in anhydrous ether (62 ml) was added dropwise 1.5M lithium diisopropylamide mono(tetrahydrofuran) in hexane (62 ml) under nitrogen atmosphere at −70° C. After stirring for 30 minutes, into the solution was bubbled sulfur dioxide for 1 hour with stirring at −60° C. Then the solution was stirred for 1 hour at room temperature and the formed precipitate was separated by filtration to give lithium 3-chlorobenzo[b]furan-2-sulfidate. To the suspension of the product in dichloromethane (250 ml) was added N-chlorosuccinimide (11.0 g) at −50° C. and stirred for 3 hours. After stirring for 2 hours under ice-cooling. insoluble matters were filtered off. Dichloromethane was removed in vacuo and the residue was purified by silica gel column chromatography to give 8.8 g of the objective compound.

Melting point: 60.6°–68.2° C.

IR (KBr, $cm^{-1}$): 1538, 1402, 1232, 1183, 1151, 1039

NMR ($CDCl_3$, ppm): 7.40–7.98 (4H, m)

Step 2

Preparation of N-(3-chlorobenzo[b]furan-2-ylsulfonyl)glycine ethyl ester

To a suspension of 3-chlorobenzo[b]furan-2-ylsulfonyl chloride (8.6 g) and glycine ethyl ester hydrochloride (9.6 g) in dichloromethane (83 ml) was added slowly triethylamine (10.4 ml) under ice-cooling and then the resulting mixture was stirred for 30 minutes at room temperature. Water (150 ml) was added to the resultant solution and acidified with 1M hydrochloric acid to a pH 2, and the acidified solution was extracted with ethyl acetate (300 ml). After drying over anhydrous magnesium sulfate, ethyl acetate was removed in vacuo to give 10.2 g of the objective compound.

Melting point: 104.5°–110.8° C.

IR (KBr, $cm^{-1}$): 3203, 1736, 1365, 1230, 1149

NMR (DMSO-$d_6$, ppm): 1.01 (3H, t, J=7.1 Hz), 3.89 (2H, q, J=7.1 Hz), 3.94 (2H, s), 7.50–7.73 (4H, m), 9.12 (1H, bs)

Step 3

Preparation of N-(3-chlorobenzo[b]furan-2-ylsulfonyl)glycine

To a solution of N-(3-chlorobenzo[b]furan-2-ylsulfonyl)glycine ethyl ester (10.2 g) in tetrahydrofuran (160 ml) was added dropwise a solution of sodium hydroxide (4.9 g) in water (16 ml) under ice-cooling and the resulting solution was stirred for 1 hour. After stirring for 30 minutes at room temperature, tetrahydrofuran was removed in vacuo. Water (200 ml) was added to the residue and then acidified with concentrated hydrochloric acid under ice-cooling to a pH1 and the acidified solution was extracted with ethyl acetate (500 ml). The organic layer was washed with saturated aqueous NaCl solution. After drying over anhydrous magnesium sulfate, ethyl acetate was removed in vacuo to give 9.2 g of the objective compound.

Melting point: 163.8°–167.9° C.

IR (KBr, $cm^{-1}$: 3236, 1709, 1369, 1232, 1153

NMR (DMSO-$d_6$, ppm): 3.84 (2H, d, J=5.9 Hz), 7.38–7.81 (4H, m), 9.03 (1H, t, J=5.9 Hz), 12.67 (1H, bs)

Step 4

Preparation of 1-(3-chlorobenzo[b]furan-2-ylsulfonyl)-2-thiohydantoin

To a mixture of N-(3-chlorobenzo[b]furan-2-ylsulfonyl)glycine (9.2 g), ammonium thiocyanate (5.32 g) and acetic anhydride (18 ml) was added dropwise pyridine (6.68 ml) under ice-cooling and resulting mixture was stirred for 30 minutes at room temperature, for 30 minutes at 40° C. and for 2 hours at 70°–80° C. After coolivg to room temperature, the resulting solution was poured into ice-water (300 ml) and the formed precipitate was separated by filtration and washed with water-ethanol to give 6.73 g of the objective compound.

Melting point: 195.4°–204.7° C.

IR (KBr, $cm^{-1}$): 3158, 1758, 1393, 1234, 1179

NMR (DMSO-$d_6$, ppm): 4.83 (2H, s), 7.56–7.90 (4H, m)

Step 5

Preparation of 1-(3-chlorobenzo[b]furan-2-ylsulfonyl)hydantoin

To a suspension of iodine monochloride (5.3 ml) in 1M hydrochloric acid (160 ml) was added 1-(3-chlorobenzo[b]furan-2-ylsulfonyl)-2-thiohydantoin (6.7 g) and then dichloromethane (200 ml) dropwise. The mixture was stirred for 1.5 hours under ice-cooling and for 1.5 hours at room temperature. After adding saturated aqueous sodium sulfite solution, the reaction mixture was extracted with ethyl acetate (600 ml). The organic layer was washed with successive saturated aqueous sodium sulfite solution and saturated aqueous NaCl solution. After drying over anhydrous magnesium sulfate, ethyl acetate was removed in vacuo and the residue was washed with successive ether and ether-ethyl acetate to give 3.15 g of the objective compound.

Melting point: 246.6°–256.8° C.

IR (KBr, $cm^{-1}$): 3226, 1744, 1397, 1363, 1174, 1156

NMR (DMSO-$d_6$, ppm): 4.51 (2H, s), 7.54–7.89 (4H, m), 11.81 (1H, bs)

EXAMPLE 92

Preparation of 1-(4-bromobenzo[b]furan-2-ylsulfonyl)hydantoin

Step 1

Preparation of (3-bromophenyloxy)acetaldehyde dimethyl acetal

To a suspension of 60% sodium hydride. (60 g) in N,N-dimethylformamide (1.4 l) was added dropwise 3-bromophenol (260 g) under ice-cooling. After stirring for 10 minutes, to the solution was added dropwise bromoacetaldehyde dimethyl acetai (318 g) and the mixture was heated with stirring for 3 hours at 90° C. After cooling, water was added to the resulting solution and acidified with 1 M hydrochloric acid and then extracted with ether (3l). The organic layer was washed with successive water, saturated aqueous sodium bicarbonate solution and saturated aqueous NaCl solution. After drying over anhydrous sodium sulfate, ether was removed in vacuo and the residue was purified by silica gel column chromatography to give 363.3 g of the objective compound.

IR (neat, $cm^{-1}$): 2941, 2835, 1615, 1506, 1458

NMR ($CDCl_3$, ppm): 3.44 (6H, s), 3.96 (2H, d, J=5.0 Hz), 4.69 (1H, t, J=5.0 Hz), 6.77–7.26 (4H, m)

Step 2

Preparation of mixture of 4-bromobenzo[b]furan and 6-bromobenzo[b]furan

Under ice-cooling, to phosphoric acid (413.5 ml) was added phosphorus pentoxide (344.2 g) and then chlorobenzene (870 ml). The resulting mixture was heated up to 125° C. To the mixture was added dropwise the solution of the product obtained in Step 1 (181.7 g) in chlorobenzene (150 ml) at 125° C. and heated with stirring for 1 hour at 12:5° C. After cooling, the resulting mixture was poured into ice-water (2l) and extracted with ether (2l). The organic layer was washed with successive saturated aqueous sodium bicarbonate solution and saturated aqueous NaCl solution. After drying over anhydrous sodium suifate, ether and chlorobenzene were removed in vacuo and the residue was purified by silica gel column chromatography to give 116 g of the objective compound.

Step 3

Preparation of 4-bromobenzo[b]furan-2-ylsulfonyl chloride

To a solution of the mixture obtained in Step 2 (100 g) in anhydrous ether (430 ml) was added dropwise 1.5 M lithium diisopropylamide mono(tetrahydrofuran) in cyclohexane (430 ml) under nitrogen atmosphere at –70° C. After stirring for 30 minutes, into the solution was bubbled sulfur dioxide for 1 hour with stirring at –60° C. Then the solution was stirred for 3 hours at room temperature and the formed precipitate was separated by filtration to give a mixture of lithium 4-bromobenzo[b]furan-2-sulfinate and lithium 6 bromobenzo[b]furan-2-sulfinate. To the suspension of the products in dichloromethane (2l) was added N-chlorosuccinimide (96 g) at –50° C. and stirred for 3 hours under ice-cooling. Insoluble matters were filtered off and dichloromethane was removed in vacuo and the residue was purified by silica gel column chromatography to give 14.1 g of the objective compound.

Melting point: 87.2° C.

IR (KBr, $cm^{-1}$): 1603, 1578, 1389, 1175, 1165

NMR ($CDCl_3$, ppm): 7.43–7.67 (4H, m)

Step 4

Preparation of N-(4-bromobenzo[b]furan-2-ylsulfonyl)glycine ethyl ester

Starting from the product obtained in Step 3 (14.1 g), the objective compound (16.8 g) was obtained in a manner similar to Step 2 of Example 91.

Melting point: 115.6°–117.3° C.

IR (KBr, $cm^{-1}$): 3199, 1361, 1221, 1158

NMR ($CDCl_3$, ppm): 1.18 (3H, t, J=7.1 Hz), 3.97 (2H, d, J=5.3 Hz), 4.09 (2H, q, J=7.1 Hz), 5.45 (1H, t, J=5.3 Hz), 7.26–7.58 (4H, m)

Step 5

Preparation of N-(4-bromobenzo[b]furan-2-ylsulfonyl)glycine

Starting from the product obtained in Step 4 (16.8 g), the objective compound (14.4 g) was obtained in a manner similar to Step 3 of Example 91.

Melting point: 180.0°–182.1° C.

IR (KBr, $cm^{-1}$): 3253, 1738, 1361, 1262, 1165

NMR (DMSO-$d_6$, ppm): 3.81 (2H, s), 7.38–7.81 (4H, m), 8.85 (1H, bs)

Step 6

Preparation of 1-(4-bromobenzo[b]furan-2-ylsulfonyl)-2-thiohydantoin

To a suspension of the product obtained in Step 5 (14.4 g) and ammonium thiocyanate (7.2 g) in acetic anhydride (28 ml) was added dropwise pyridine (9.1 ml) and the mixture was heated with stirring for 2 hours at 60°–70° C. After cooling to room temperature, the resulting solution was poured into ice-water (500 ml) and the formed precipitate was separated and washed with ethanol to give 10.7 g of the objective compound.

Melting point: 253.3° C.

IR (KBr, $cm^{-1}$): 3140, 1756, 1391, 1248, 1166

NMR (DMSO-$d_6$, ppm): 4.77 (2H, s), 7.45–7.88 (3H, m), 7.95 (1H, s), 12.86 (1H, bs)

Step 7

Preparation of 1-(4-bromobenzo[b]furan-2-ylsulfonyl)hydantoin

Starting from the product obtained in Step 6 (10.7 g), the objective compound (4.3 g) was obtained in a manner similar to Step 5 of Example 91.

Melting point: 291.7°–293.5° C.

IR (KBr, $cm^{-1}$): 3240, 1741, 1390, 1355, 1167

NMR (DMSO-$d_6$, ppm): 4.48 (2H, s), 7.45–7.90 (4H, m), 11.78 (1H, t,s)

EXAMPLE 93

Preparation of 1-(7-fluorobenzo[b]furan-2-ylsulfonyl)hydantoin (compound 48)

Step 1

Preparation of 7-fluorobenzo[b]furan-2-ylsulfonyl chloride

Starting from 7-fluorobenzo[b]furan (10.4 g), the objective compound (5.7 g) was obtained in a manner similar to Step 1 of Example 91.

Melting point: 114° C.

IR (KBr, $cm^{-1}$): 1596, 1546, 1372, 1267, 1178

NMR ($CDCl_3$, ppm): 7.24–7.69 (4H, m)

Step 2

Preparation of N-(7-fluorobenzo[b]furan-2-ylsulfonyl)glycine ethyl ester

Starting from the product obtained in Step 1 (5.7 g), the objective compound (6.45 g) was obtained in a manner similar to Step 2 of Example 91.

Melting point: 84.5° C.

IR (KBr, $cm^{-1}$): 3238, 1734, 1376, 1232. 1165

NMR (DMSO-$d_6$, ppm): 1.03 (3H, t, J=7.1 Hz), 3.89 (2H, d, J=6.3 Hz), 3.92 (2H, q. J=7.1 Hz), 7.32–7.66 (4H, m), 9.05 (1H, t, J=6.3 Hz)

Step 3

Preparation of N-(7-fluorobenzo[b]furan-2-ylsulfonyl)glycine

Starting from the product obtained in Step 2 (6.4 g), the objective compound (5.42 g) was obtained in a manner similar to Step 3 of Example 91.

Melting point: 140.1° C. (decomposition)

IR (KBr, $cm^{-1}$): 3303, 1734, 1349, 1262, 1160

NMR (DMSO-$d_6$, ppm): 3.80 (2H, d, J=5.0 Hz), 728–7.66 (4H, m), 8.90 (1H, t, J=5.0 Hz)

Step 4

Preparation of 1-(7-fluorobenzo[b]furan-2-ylsulfonyl)-2-thiohydantoin

To a suspension of the product obtained in Step 3 (5.4 g) and ammonium thiocyanate (3.32 g) in acetic anhydride (12.7 ml) was added dropwise pyridine (4.16 ml) under ice-cooling and nitrogen atmosphere. The mixture was heated with stirring for 2 hours at 70° C. After cooling to room temperature, the resulting solution was poured into ice-water (200 ml) and added small amount of ethanol and the formed precipitate was separated and dissolved in ethyl acetate (200 ml) and the solution was washed with successive water and saturated aqueous NaCl solution. After drying over anhydrous sodium sulfate, ethyl acetate was removed in vac and the residue was washed with ethanol to give 2.83 g of the objective compound.

Melting point: 229.9°–232.0° C.

IR (KBr, $cm^{-1}$): 3258, 1765, 1744, 1448, 1177

NMR (DMSO-$d_6$, ppm): 4.73 (2H, s), 7.39–7.77 (3H, m), 8.13 (1H, d, J=2.6 Hz), 12.83 (1H, bs)

Step 5

Preparation of
1-(7-fluorobenzo[b]furan-2-ylsulfonyl)hydantoin

Starting from the product obtained in Step 4 (2.8 g), the objective compound (1.1 g) was obtained in a manner similar to Step 5 of Example 91.

Melting point: >300° C.

IR (KBr, $cm^{-1}$): 5381, 1735, 1610, 1383, 1166

NMR (DMSO-$d_6$, ppm): 3.98 (2H, s), 7.34–7.71 (3H, m), 7.78 (1H, d, J=3.0 Hz)

EXAMPLE 94

Preparation of
1-(4,5-dichlorobenzo[b]furan-2-ylsulfonyl)hydantoin
(compound 44)

Step 1

Preparation of (3,4-dichlorophenyloxy)acetaldehyde dimethyl acetal

Starting from 3,4-dichlorophenol (200 g), the objective compound (218.8 g) was obtained in a manner similar to Step 1 of Example 92.

IR (neat, $cm^{-1}$): 2940, 2830, 1595, 1475, 1297, 1235

NMR ($CDCl_3$, ppm): 3.45 (6H, s), 3.96 (2H, d, J=5.3 Hz), 4.69 (1H, t, J=5.3 Hz), 6.78 (1H, dd, J=8.9, 3.0 Hz), 7.02 (1H, d, J=3.0 Hz), 7.31 (1H, d, J=8.9 Hz)

Step 2

Preparation of mixture of 4,5-dichlorobenzo[b]furan and 5,6-clichlorobenzo[b]furan Starting from the product obtained in Step 1 (218.8 g), the mixture of the objective compounds (102.1 was obtained in a manner similax to Step 2 of Example 92.

Step 3

Preparation of
4,5-dichlorobenzo[b]furan-2-ylsulfonyl chloride and
5,6-dichlorobenzo[b]furan-2-ylsulfonyl chloride To a solution of the mixture obtained in Step 2 (100 g) in anhydrous ether (440 ml) was added dropwise 1.5 M lithium diisopropylnmide mono(tetrahydrofuran) in cyclohexane (440 ml) under nitrogen atmosphere at −70° C. over 1 hour, then into the solution was bubbled sulfur dioxide for 1.5 hours at −70° C. After stirring for 1 hour at room temperature, the solvent was removed in vacuo and ether was added to the residue. The formed precipitate was separated by filtration to give a mixture of lithium 4,5-dichlorobenzo[b]furan-2-sulfinate and lithium 5,6-dichlorobenzo[b]furan-2-sulfinate. To the suspension of the products in dichloromethane (1.8 l) was added N-chlorosuccimimide (92.1 g) at −50° C. and stirred for 1.5 hours. At room temperature, insoluble matters were filtered off and dichloromethane was removed in vacuo and the residue was purified by silica gel column chromatography to give 17.4 g of 4,5-dichlorobenzo[b]furan-2-ylsulfonyl chloride and 7.4 g of 5,6-dichlorobenzo[b]furan-2-ylsulfonyl chloride, respectively. 4,5-dichlorobenzo[b]furan-2-ylsulfonyl chloride Melting point: 114.6° C.

IR (KBr, $cm^{-1}$, ppm), 1529, 1444, 1401, 1191

NMR (DMSO-$d_6$, ppm): 6.87 (1H, d, J=1.0 Hz), 7.55 (1H, d, J=8.9 Hz), 7.69 (1H, dd, J=8.9, 1.0 Hz) 5,6-dichlorobenzo[b]furan-2-ylsulfonyl chloride Melting point: 159.8° C.

IR (KBr, $cm^{-1}$): 1537, 1390, 1163, 1081

NMR (DMSO-$d_6$, ppm): 6.87 (1H, d, J=1.0 Hz), 7.92 (1H, s), 8.02 (1H, d, J=1.0 Hz)

Step 4

Preparation of
N-(4,5-dichlorobenzo[b]furan-2-ylsulfon)glycine ethyl ester

Starting from 4,5-dichlorobenzo[b]furan-2-ylsulfonyl chloride obtained in Step 3 (17 g), the objective compound (18.2 g) was obtained in a manner similar to Step 2 of Example 91.

Melting point: 155.2°–155.5° C.

IR (KBr, cm-$^{-1}$): 3199, 1737, 1225, 1160

NMR ($CDCl_3$, ppm): 1.05 (3H, t, J=7.1 Hz), 3.92 (2H, s), 3.95 (2H, q, J=7.1 Hz), 7.56 (1H, s), 7.78 (2H, s), 9.09 (1H, bs)

Step 5

Preparation of
N-(4,5-dichlorobenzo[b]furan-2-ylsulfonyl)glycine

Starting from the product obtained in Step 4 (18 g), the objective compound (16.2 g) was obtained in a manner similar to Step 3 of Example 91.

Melting point: 189.8°–194.7° C.

IR (KBr, $cm^{-1}$): 3320, 1719, 1366, 1256, 1162

NMR (DMSO-$d_6$, ppm): 3.83 (2H, d, J=6.3 Hz), 7.56 (1H, s), 7.76 (2H, s), 8.97 (1H, t, J=6.3 Hz)

Step 6

Preparation of 1-(4,5-dichlorobenzo[b]furan-2-ylsulfonyl)-2-thiohydantoin

Starting from the product obtained in Step 5 (16 g), the objective compound (7.4 g) was obtained in a manner similar to Step 4 of Example 91.

Melting point: 214.6°–217.5° C.

IR (KBr, $cm^{-1}$): 1793, 1762, 1445, 1167

NMR (DMSO-$d_6$, ppm): 4.77 (2H, s), 7.85 (2H, s), 8.11 (1H, s), 12.95 (1H, bs)

Step 7

Preparation of
1-(4,5-dichlorobenzo[b]furan-2-ylsulfonyl)hydantoin

To a suspension of iodine monochloride (6.3 ml) in 1 M hydrochloric acid (150 ml) were added successively the product obtained in Step 6 (7.3 g) and dropwise dichloromethane (150 ml) over 10 minutes. The mixture was stirred for 2.5 hours at room temperature. Under ice-cooling, to the solution was added saturated aqueous sodium sulfite solution and stirred for a while. The formed precipitate was separated by filtration and washed with successive water, ethanol and ether to give 4.8 g of the objective compound.

Melting point: 290.7°–292.0° C. (decomposition)

IR (KBr, $cm^{-1}$): 3256, 1742, 1391, 1356, 1168

NMR (DMSO-$d_6$, ppm): 4.47 (2H, s), 7.85 (2H, s), 7.98 (1H, s), 11.80 (1H, bs)

EXAMPLE 95

Preparation of
1-(5,6-dichlorobenzo[b]furan-2-ylsulfonyl)hydantoin
(compound 45)

Step 1

Preparation of
N-(5,6-dichlorobenzo[b]furan-2-ylsulfonyl)glycine
ethyl ester

To a solution of 5,6-dichlorobenzo[b]furan-2-ylsulfonyl chloride obtained in Step 3 of Example 64 (7.4 g) in dichleromethane (60 ml) was added glycine ethyl ester hydrochloride (7.95 g) and added slowly triethylamine (7.89 ml) under ice-cooling and nitrogen atmosphere. The resulting solution was poured into water (100 ml) and acidified with 1 M hydrochloric acid and extracted with ethyl acetate. The organic layer was washed with saturated aqueous NaCl solution and dried over anhydrous sodium sulfate. Ethyl acetate was removed in vacuo and the residue was washed with hexane to give 8.7 g of the objective compound.

Melting point: 132.7°–133.5° C.

IR (KBr, $cm^{-1}$): 3227, 1735, 1360. 1225, 1158

NMR (DMSO-$d_6$, ppm): 1.06 (3H, t, J= 6.9 Hz), 3.90 (2H, s), 3.95 (2H, q, J=6.9 Hz), 7.52 (1H, s), 8.08 (1H, s), 8.20 (1H, s), 9.05 (1H, b)

Step 2

Preparation of
N-(5,6-dichlorobenzo[b]furan-2-ylsulfonyl)glycine

Starting from the product obtained in Step 1 (8.6 g), the objective compound (7.8 g) was obtained in a manner similar to Step 3 of Example 91.

Melting point: 192.6°–201.8° C.

IR (KBr, $cm^{-1}$): 3367, 1719, 1359, 1248, 1159

NMR (DMSO-$d_6$, ppm): 3.80 (2H, d, J= 5.9 Hz), 7.51 (1H, d, J=1.0 Hz), 8.08 (1H, s), 8.19 (1H, d, J=-- 1.0 Hz), 8.92 (1H, t, J=5.9 Hz)

Step 3

Preparation of 1-(5,6-dichlorobenzo[b]furan-2-ylsulfonyl)-2-thiohydantoin

Starting from the product obtained in Step 2 (7.7 g), the objective compound (3.7 g) was obtained in a manner similar to Step 4 of Example 91.

Melting point: > 246.0° C. (decomposition)

IR (KBr, $cm^{-1}$): 3100, 1743, 1449, 1246, 1166

NMR (DMSO-$d_6$, ppm): 4.73 (2H, s), 8.02 (1H, d, J=1.0 Hz), 8.20 (1H, s), 8.26 (1H, d, J= 1.0 Hz), 12.82 (1H, bs)

Step 4

Preparation of
1-(5,6-dichlorobenzo[b]furan-2-ylsulfonyl)hydantoin

Starting from the product obtained in Step 3 (3.7 g), the objective compound (2.7 g) was obtained in a manner similar to Step 5 of Example 91.

Melting point: > 300° C. (decomposition)

IR (KBr, $cm^{-1}$): 1732, 1389, 1186, 1167

NMR (DMSO-$d_6$, ppm): 4.31 (2H, s), 7.82 (1H, d, J=0.7 Hz), 8.16 (1H, s), 8.27 (1H, d, J=0.7 Hz)

EXAMPLE 96

Preparation of 1-(3-bromo-7-fluorobenzo[b]furan-2-ylsulfonyl)hydantoin (compound 49)

Step 1

Preparation of
2,3-dibromo-2,3-dihydro-7-fluorobenzo[b]furan

To a solution of 7-fluorobenzo[b]furan (16 g) in carbon tetrachloride (40 ml) was added dropwise a solution of bromine (22 g) in carbon disulfide (40 ml) at –30° C. and the solution was stirred for 1 hour. At room temperature, the formed precipitate was separated by filtration to give 34.4 g of the objective compound.

IR (KBr, $cm^{-1}$): 1634, 1601, 1489, 1459, 1279, 1179

NMR ($CDCl_3$, ppm): 5.74 (1H, d, J=1.3 Hz), 6.93 (1H, s). 7.11–7.35 (3H, m)

Step 2

Preparation of 3-bromo-7-fluorobenzo[b]furan

To a solution of potassium hydroxide (12.7 g) in ethanol (180 ml) was slowly added the product obtained in Step 1 (34 g) and stirred for 3 hours. The resulting solution was neutralized by acetic acid, then extracted with ether. The organic layer was washed with successive water and saturated aqueous NaCl solution. After drying over anhydrous sodium sulfate, ether was removed in vacuo to give 24.1 g of the objective compound.

IR (neat, $cm^{-1}$): 3150, 1636, 1595, 1494, 1434, 1322

NMR ($CDCl_3$, ppm): 6.98–7.36 (3H, m), 7.68 (1H, s)

Step 3

Preparation of 3-bromo-7-fluorobenzo[b]furan-2-ylsulfonyl chloride

Starting from the product obtained in Step 2 (24.1 g), the objective compound (12.2 g) was obtained in a manner similar to Step 1 of Example 91.

IR (KBr, $cm^{-1}$): 1602, 1533, 1385, 1168

NMR (DMSO-$d_6$, ppm): 7.33–7.39 (3H, m)

Step 4

Preparation of N-(3-bromo-7-fluorobenzo[b]furan-2-ylsulfonyl)glycine ethyl ester Starting from the product obtained in Step 3 (12.2 g), the objective compound (10.2 g) was obtained in a manner similar to Step 2 of Example 91.

Melting point: 126.2°–126.4 C.

IR (KBr, $cm^{-1}$): 3200, 1731, 1366, 1237, 1142

NMR (DMSO-$d_6$, ppm): 1.01 (3H, t, J=7.1 Hz) 3.89 (2H, q, J=7.1 Hz), 3.96 (2H, d, J=5.6 Hz), 7.47–7.66 (3H, m), 9.32 (1H, t, J=5.6 Hz)

Step 5

Preparation of N-(3-bromo-7-fluorobenzo[b]furan-2-ylsulfonyl)glycine

Starting from the product obtained in Step 4 (10.2 the objective compound (7.25 g) was obtained in a manner similar to Step 3 of Example 91.

Melting point: 148.5°–159.6° C.

IR (KBr, $cm^{-1}$): 3223, 1716, 1373, 1246, 1163

NMR (DMSO-$d_6$, ppm): 3.86 (2H, s), 7.46–7.58 m), 9.18 (1H, bs)

Step 6

Preparation of 1-(3-bromo-7-fluorobenzo[b]furan-2-ylsulfonyl)-2-thiohydantoin

Starting from the product obtained in Step 5 (7.2 g), the objective compound (5.07 g) was obtained in a manner similar to Step 4 of Example 91.

Melting point: 224.3°–224.7° C. (decomposition)

IR (KBr, $cm^{-1}$): 3290, 1793, 1765, 1235, 1141

NMR (DMSO-$d_6$, ppm): 4.83 (2H, s), 7.57–7.72 (3H, m), 12.93 (1H, bs)

Step 7

Preparation of 1-(3-bromo-7-fluorobenzo[b]furan-2-ylsulfonyl)hydantoin

To a suspension of iodine monochloride (3.3 ml) in 1 M hydrochloric acid (110 ml) was added the product obtained in Step 6 (5 g) and dropwise dichloromethane (140 ml). The mixture was stirred for 6 hours at room temperature and then additive iodine monochloride (1.7 ml) was added to the mixture and the resulting mixture was stirred for 1 hour. To the resulting solution was added saturated aqueous sodium sulfite solution and formed precipitate was separated by filtration. The organic layer was washed with saturated aqueous NaCl solution and dried over anhydrous magnesium sulfate. Formed precipitate was suspended in 1 M hydrochloric acid (100 ml) and the suspension was extracted with ethyl acetate. The organic layer was washed with saturated aqueous NaCl solution and dried over anhydrous magnesium sulfate. Both extracts were combined and the solvent was removed in vacuo. The resulting residue was washed with successive ethanol and ether to give 1.66 g of the objective compound.

Melting point: 266.6°–270.6° C.

IR (KBr, $cm^{-1}$): 3160, 1725, 1393, 1184, 1149

NMR (DMSO-$d_6$, ppm): 4.50 (2H, s), 7.53–7.77 (3H, m), 11.85 (1H, bs)

Compounds of Example 97 to 102 prepared in a manner similar to Example 91 are summarized in the following table 11 together with corresponding IR, and NMR data and melting points.

TABLE 11

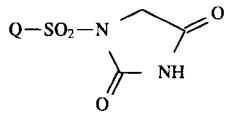

| Ex. No. | Q | IR(KBr, $cm^{-1}$) | NMR(DMSO)-$d_6$, ppm) | M.P. (°C.) |
|---|---|---|---|---|
| 97 | 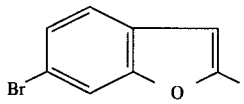 | 1732, 1389 1181, 1166 | 4.32(2H, s), 7.59(1H, dd, J=8.6, 1.7Hz), 7.82(1H, d, J=8.6Hz), 7.87(1H, d, J=1.7Hz), 8.12(1H, s) | >297 (dec.) |
| 98 | 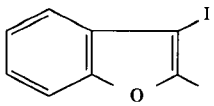 | 3216, 1734, 1397, 1363, 1175, 1151 | 4.54(2H, s), 7.51~7.75(4H, m), 11.82(1H, bs) | 292 (dec.) |

TABLE 11-continued
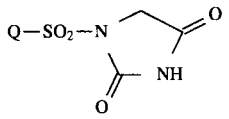
| Ex. No. | Q | IR(KBr, $cm^{-1}$) | NMR(DMSO)-$d_6$, ppm) | M.P. (°C.) |
|---|---|---|---|---|
| 99 | 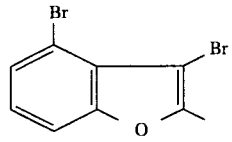 | 1742, 1394, 1183, 1174, 1153 | 4.55(2H, s), 7.55(1H, t, J=7.9Hz), 7.74(1H, dd, J=7.9, 1.3Hz), 7.91(1H, dd, J=7.9, 1.3Hz), 11.87(1H, bs) | 256.3~258.6 (dec.) |
| 100 | 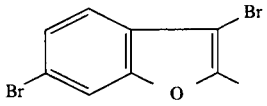 | 3262, 1734, 1397, 1352, 1178, 1170 | 4.44(2H, s), 7.70(1H, d, J=1.0Hz), 7.71(1H, s), 8.22(1H, d, J=1.0Hz) | >249.2 (dec.) |
| 101 | 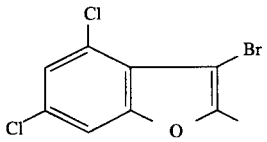 | 3279, 1744, 1404, 1176, 1148 | 4.51(2H, s), 7.74(1H, d, J=1.7Hz), 8.16(1H, d, J= 1.7Hz), 11.82(1H, bs) | 249.5~251.7 |
| 102 | 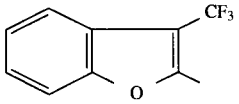 | 3220, 1745, 1407, 1357, 1181, 1152. | 4.48(2H, s), 7.58~7.97(4H, m) | 238.8~240.8 |
Another intermediate compounds of Example 29 to 39, 41 to 48, 50, 52, 54, 63 to 83, 97 to 102 are summarized in the following table 12 to 16 together with corresponding IR and NMR data and melting points.

TABLE 12
| Ex. No. | Q | IR(KBr, $cm^{-1}$) | NMR(DMSO-$d_6$, ppm) | M.P. (°C.) |
|---|---|---|---|---|
| | $Q-SO_2-Cl$ | | | |
| 29 | 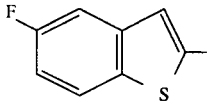 | 1500, 1392, 1216, 1174, 1001 | 7.12~8.00(3H, m), 7.43(1H, s) | |
| 30 | 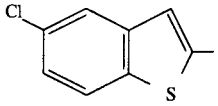 | 1588, 1493, 1169, 1078 | 7.55(1H, dd, J=8.9, 1.3Hz), 7.85(1H, d, J=8.9Hz), 7.95(1H, d, J=1.3Hz), 8.07(1H, s)* | |
| 31 | 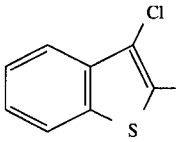 | 1592, 1480, 1391, 1248, 1180 | 7.37~8.01(4H, m) | |
| 32 | 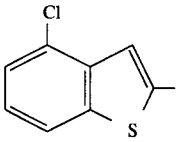 | 1584, 1544, 1493, 1388, 1170, 1007 | 7.35~7.95(3H, m), 7.42(1H, s) | |
| 33 | 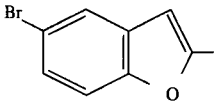 | 1530, 1372, 1275, 1240, 1160 | 7.46~7.92(3H, m), 7.58(1H, s)* | |
| 34 | 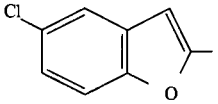 | 1531, 1394, 1164, 1080, 809 | 7.50~7.76(3H, m), 7.59(1H, s)* | |
| 35 | 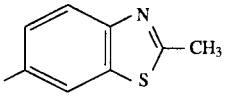 | 1508, 1406, 1375, 1320, 1180 | 2.81(3H, s), 7.74~8.24(3H, m) | |
| 37 | 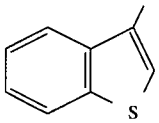 | 1423, 1375, 1172 | 7.38~7.72(2H, m), 7.84~8.01(1H, m), 8.26~8.46(1H, m), 8.51(1H, s)* | |
| 38 | 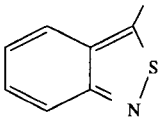 | 1383, 1170, 750, 590 | 7.53~7.72(2H, m), 7.87~8.03(1H, m), 8.07~8.23(1H, m)* | |
| 39 | 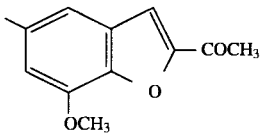 | | 2.67(3H, s), 4.13(3H, s), 7.51~8.03(3H, m)* | |
| 41 | 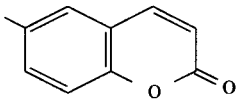 | 1734, 1375, 1169, 1102 | 6.51(1H, d, J=9.6Hz), 7.36(1H, d, J=8.6Hz), 7.85(1H, dd, J=8.6, 2.0Hz), 8.02(1H, d, J=2.0Hz), 8.16(1H, d, J=9.6Hz) | |
| 42 | 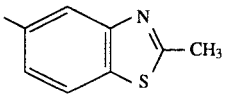 | 1415, 1381, 1371, 1237, 1172, 1151 | 2.81(3H, s), 7.60~8.06(3H, m), | |

TABLE 12-continued
| Ex. No. | Q | IR(KBr, $cm^{-1}$) | NMR(DMSO-$d_6$, ppm) | M.P. (°C.) |
|---|---|---|---|---|
| | $Q-SO_2-Cl$ | | | |
| 43 | 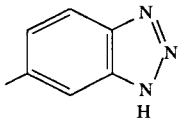 | 1617, 1383, 1371, 1216, 1173 | 7.70(1H, dd, J=8.6, 1.0Hz), 7.87(1H, d, J=8.6Hz), 8.08(1H, d, J=1.0Hz) | |
| 44 | 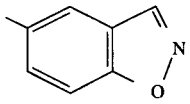 | 1604, 1380, 1192, 1161, 534 | 7.86(1H, d, J=8.9Hz), 8.27(1H, dd, J=8.9, 2.0Hz), 8.55(1H, d, J=2.0Hz), 8.93(1H, s)* | |
| 45 | 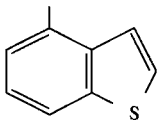 | 1379, 1368, 1314, 1171, 1158 | 7.50(1H, t, J=7.9Hz), 7.82(1H, d, J=5.6Hz), 8.00~8.28(3H, m)* | |
| 46 | 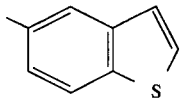 | 1375, 1311, 1202, 1169, 1043 | 7.47~8.15(5H, m) | |
| 47 | 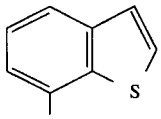 | | 7.35~7.90(5H, m) | |
| 48 | 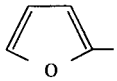 | 1457, 1395, 1214, 1166 | 7.05~7.14(2H, m), 8.21~8.24(1H, m) | |
| 50 | 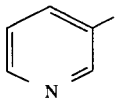 | 1625, 1590, 1522, 1377, 1175 | 8.00~8.98(4H, m) | |
| 52 | 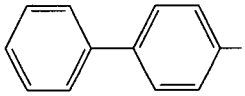 | 1590, 1374, 1178, 765 | 7.36~7.78(9H, m) | |
| 54 | 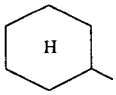 | 2945, 2941, 1453, 1373, 1161 | 1.23~2.50(10H, m), 3.39~3.65(1H, m)* | |
| 63 | 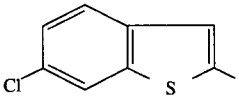 | 1479, 1380, 1166, 1000, 548 | 7.37(1H, dd, J=8.6, 1.3Hz), 7.44(1H, s), 7.84(1H, d, J=8.6Hz), 8.04(1H, d, J=1.3Hz) | |
| 64 | 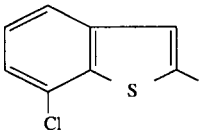 | 1493, 1454, 1390, 1167 | 7.32~7.53(2H, m), 7.62(1H, s), 7.82~7.97(1H, m) | |
| 65 | 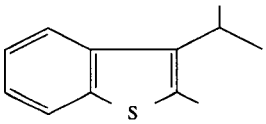 | 2968, 2935, 1503, 1465, 1375, 1167 | 1.59(3H, d, J=7.3Hz), 4,11~4.44(1H, m), 7.44~7.64(2H, m), 7.83~7.94(1H, m), 8.19~8.26(1H, m)* | |

TABLE 12-continued
| Ex. No. | Q | IR(KBr, $cm^{-1}$) | NMR(DMSO-$d_6$, ppm) | M.P. (°C.) |
|---|---|---|---|---|
| | $Q-SO_2-Cl$ | | | |
| 66 | 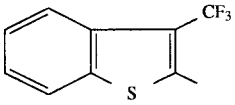 | | 7.42~8.06(4H, m) | |
| 67 | 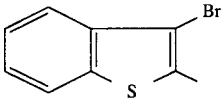 | 1473, 1389, 1177, 533 | 7.51~8.11(4H, m)* | |
| 68 | 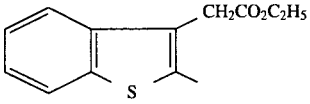 | 1737, 1371, 1329, 1201, 1174 | 1.17(3H, t, J=7.3Hz), 4.05(2H, q, J=7.3Hz), 4.20(2H, s), 7.29~7.39(2H, m), 7.58~7.64(1H, m), 7.82~7.88(1H, m) | 90.4~93.2 (dec.) |
| 70 | 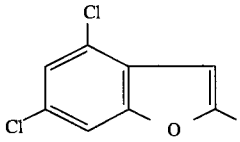 | 1575, 1530, 1394, 1384, 1174 | 7.47~7.69(3H, m)* | 116.0~116.9 |
| 71 | 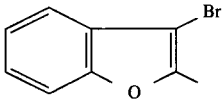 | 1520, 1395, 1231, 1148 | 7.31~7.67(4H, m) | |
| 72 | 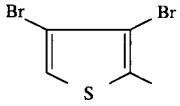 | 1396, 1178, 1049 | 7.73(1H, s) | 101.3~103.0 |
| 73 | 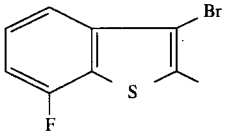 | 1488, 1384, 1174, 570 | 7.26~7.92(3H, m)* | 90.0~92.0 |
| 74 | 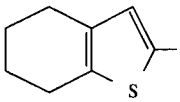 | 2948, 1436, 1417, 1166 | 1.79~1.94(4H, m), 2.62~2.85(4H, m), 7.55(1H, s)* | |
| 75 | 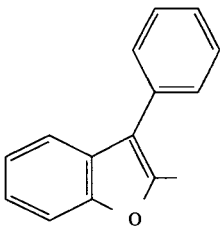 | 1398, 1242, 1182, 1147, 534 | 7.31~7.70(9H, m)* | 76.2~77.4 |
| 76 | 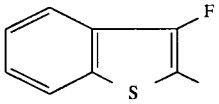 | 1526, 1389, 1370, 1179, 570, 538 | 7.42~8.27(4H, m)* | |
| 77 | 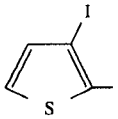 | | 6.96(1H, d, J=5.6Hz), 7.66~7.77(1H, m)* | |

TABLE 12-continued
| Ex. No. | Q | IR(KBr, $cm^{-1}$) | NMR(DMSO-$d_6$, ppm) | M.P. (°C.) |
|---|---|---|---|---|
| | $Q-SO_2-Cl$ | | | |
| 78 | 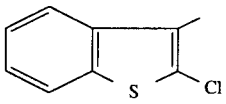 | 1478, 1419, 1383, 1178 | 7.42~8.41(4H, m)* | |
| 79 | 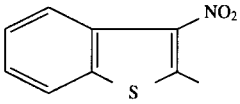 | | 7.45~7.85(3H, m), 8.40~8.50(1H, m)* | |
| 80 | 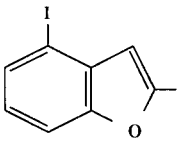 | 1381, 1161, 1086, 775 | 7.24~7.85(4H, m)* | |
| 82 | 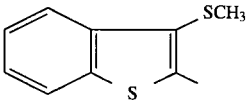 | 1377, 1172, 1164, 762, 567 | 2.58(3H, s), 7.46~8.25(4H, m)* | |
| 83 | 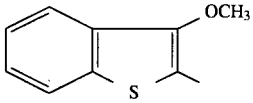 | 1510, 1377, 1348, 1175, 578 | 4.09(3H, s), 7.36~7.74(4H, m) | |
| 97 | 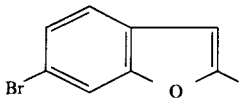 | 1533, 1385, 1168, 1077 | 7.49~7.71(3H, m), 7.86(1H, s)* | 82.1~82.9 |
| 98 | 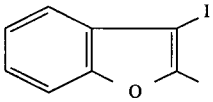 | 1507, 1501, 1391, 1225, 1139 | 7.38~7.88(4H, m)* | 88.3~91.6 |
| 101 | 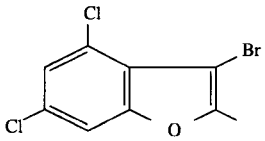 | | 7.46(1H, d, J=1.7Hz), 7.61(1H, d, J=1.7Hz)* | |
| 102 | 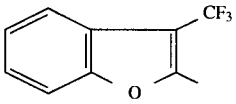 | | 7.46~7.99(4H, m)* | |
NMR data marked with asterisks (*) were measured in $CDCl_3$
TABLE 13
| Ex. No. | Q | IR(KBr, $cm^{-1}$) | NMR(DMSO-$d_6$, ppm) | M.P. (°C.) |
|---|---|---|---|---|
| | $Q-SO_2NHCH_2COOEt$ | | | |
| 97 | 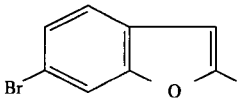 | 3340, 1742, 1357, 1204, 1161 | 1.18(3H, t, J=7.3Hz), 3.96(2H, d, J=5.6Hz), 4.10(2H, q, J=7.3Hz), 5.51(1H, t, J=5.6Hz), 7.35~7.73(4H m) | 81.2~81.5 |
| 98 | 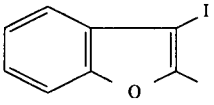 | 3184, 1738, 1364, 1225 | 1.00(3H, t, J=7.1Hz), 3.87(2H, q, J=7.1Hz), 3.92(2H, d, J=5.9Hz), 7.45~7.90(4H, m), 9.03(1H, t, J=5.9Hz) | 130.4~134.1 |

TABLE 13-continued

| Ex. No. | Q | IR(KBr, $cm^{-1}$) | NMR(DMSO-$d_6$, ppm) | M.P. (°C.) |
|---|---|---|---|---|
| | Q − $SO_2NHCH_2COOEt$ | | | |
| 99 | 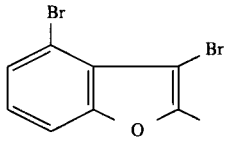 | 3197, 1737, 1366, 1229, 1162 | 1.19(3H, t, J=7.1Hz), 4.02(2H, d, J=6.6Hz), 4.10(2H, d, J=7.1Hz), 5.64(1H, t, J=6.6Hz), 7.24~7.63(3H, m) | 129.4~130.6 |
| 100 | 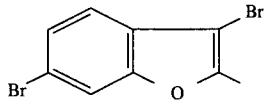 | 3295, 1732, 1366, 1232, 1147 | 1.18(3H, t, J=7.1Hz), 4.01(2H, d, J=6.6Hz), 4.08(2H, q, J=7.1Hz), 5.62(1H, t, J=6.6Hz), 7.52(2H, s), 7.74(1H, s) | 132.9~133.4 |
| 101 | 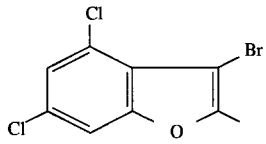 | 3236, 1731, 1365, 1233, 1148 | 1.20(3H, t, J=7.1Hz), 4.02(2H, d, J=4.9Hz), 4.11(2H, q, J=7.1Hz), 5.62(1H, t, J=4.9Hz), 7.38(1H, d, J=1.7Hz), 7.51(1H, d, J=1.7Hz) | 167.3~169.2 |
| 102 | 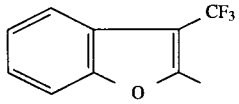 | 3202, 1739, 1371, 1228, 1171 | 1.00(3H, t, J=6.9Hz), 3.90(2H, q, J=6.9Hz), 3.99(2H, d, J=6.6Hz), 7.44~7.89(4H, m), 9.39(1H, t, J=6 6Hz) | 135.6~147.8 |

TABLE 14

| Ex. No. | Q | IR(KBr, $cm^{-1}$) | NMR(DMSO-$d_6$, ppm) | M.P. (°C.) |
|---|---|---|---|---|
| | Q − $SO_2NHCH_2CO_2H$ | | | |
| 63 | 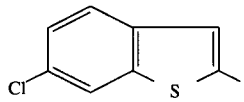 | | 3.74(2H, s), 7.48~8.27(4H, m), 8.55(1H, bs) | 210.1~213.3 |
| 64 | 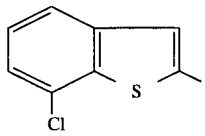 | 3270, 1732, 1394, 1354, 1260, 1160 | 3.76(2H, d, J=5.9Hz), 7.38~8.09(4H, m), 8.65(1H, t, J=5.9Hz), 12.74(1H, bs) | 193.0~205.0 |
| 65 | 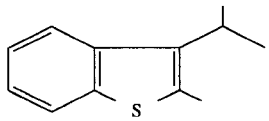 | 3312, 2980, 2968, 1726, 1321, 1143 | 1.45(6H, d, J=7.3Hz), 3.72(2H, d, J=4.3Hz), 3.84~4.17(1H, m), 7.42~8.30(4H, m), 8.61(1H, t, J=4.3Hz) | 110.0~115.5 |
| 66 | 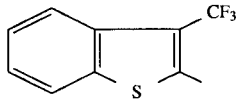 | 3354, 1730, 1421, 1361, 1214, 1164, 1122 | 3.73(2H, s), 7.57~8.25(4H, m) | 141.3~144.5 |
| 67 | 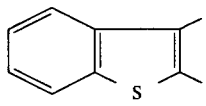 | 3304, 1725, 1709, 1487, 1353, 1249, 1160 | 3.86(2H, d, J=5.9Hz), 7.57~81.9(4H, m), 8.81(1H, t, J=5.9Hz) | 149.1~153.3 |
| 68 | 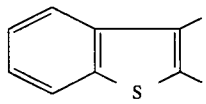 | 3294, 1735, 1158 | 1.17(3H, t, J=7.1Hz), 3.67(2H, d, J=6.3Hz), 4.08(2H, q, J=7.1Hz), 4.28(2H, s), 7.46~8.11(4H, m), 8.64(1H, t, J=6.3Hz) | 125.0~126.9 |

TABLE 14-continued
| Ex. No. | Q | IR(KBr, $cm^{-1}$) | NMR(DMSO-$d_6$, ppm) | M.P. (°C.) |
|---|---|---|---|---|
| | $Q-SO_2NHCH_2CO_2H$ | | | |
| 69 | 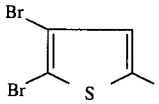 | 3280, 1734, 1372, 1347, 1312, 1255, 1167 | 3.72(2H, d, J=5.3Hz), 7.61(1H, s), 8.55(1H, t, J=5.3Hz), 12.85(1H, bs) | 200.5~202.0 |
| 70 | 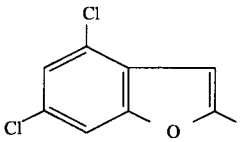 | 3275, 1718, 1364, 1161 | 3.82(2H, d, J=5.9Hz), 7.53(1H, s), 7.63(1H, d, J=1.6Hz), 7.99(1H, bs), 8.95(1H, t, J=5.9Hz) | 194.2~196.4 |
| 71 | 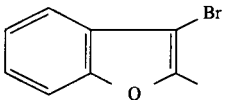 | 1717, 1709, 1437, 1369, 1150 | 3.82(2H, d, J=5.9Hz), 7.36~7.80(4H, m), 8.95(1H, t, J=5.9Hz). | 153.4~156.1 |
| 72 | 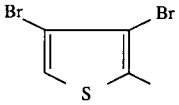 | 3340, 1718, 1321, 1252, 1153, 1141, 1130 | 3.79(2H, d, J=5.9Hz), 8.17(1H, s), 8.72(1H, t, J=5.9Hz), 12.82(1H, bs) | 203.5~205.2 |
| 73 | 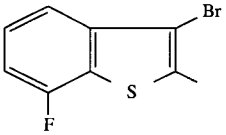 | 3344, 1713, 1498, 1341, 1247, 1163 | 3.88(2H, d, J=6.3Hz), 7.43~7.82(3H, m), 8.98(1H, t, J=6.3Hz) | 194.0~201.0 |
| 74 | 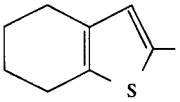 | 3315, 3201, 2433, 1752, 1443, 1326, 1187, 1158 | 1.50~1.98(4H, m), 2.40~2.88(4H, m), 3.59(2H, d, J=4.9Hz), 7.26(1H, s), 8.08(1H, t, J=4.9Hz) | 141.2~143.2 |
| 75 | 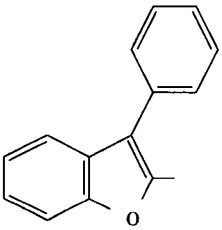 | 3265, 1716, 1352, 1236, 1169, 1139 | 3.74(2H, s), 7.08~7.81(9H, m), 8.72(1H, bs) | 151.4~153.7 |
| 76 | 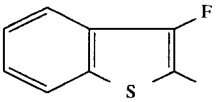 | 3290, 1742, 1375, 1255, 1173, 1118 | 3.82(2H, d, J=5.9Hz), 7.45~8.16(4H, m), 8.84(1H, t, J=5.9Hz), 12.72(1H, bs) | 129.7~134.2 |
| 77 | 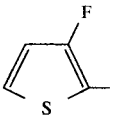 | 3306, 3117, 1732, 1546, 1424, 1412, 1336, 1160 | 3.73(2H, d, J=5.9Hz), 7.11(1H, d, J=5.6Hz), 7.86(1H, dd, J=5.6, 4.3Hz), 8.54(1H, t, J=5.9Hz), 12.72(1H, bs) | 167.4~169.4 |
| 78 | 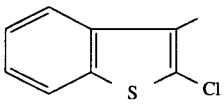 | 3264, 1725, 1420, 1350, 1249, 1160 | 3.74(2H, d, J=5.6Hz), 7.45~8.31(4H, m), 8.60(1H, t, J=5.6Hz), 12.51(1H, bs) | 126.0~129.5 |
| 79 | 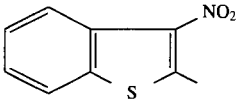 | 1747, 1589, 1367, 1198 | 4.30(2H, d, J=5.9Hz), 7.21~8.34(4H, m), 9.94(1H, t, J=5.9Hz) | 212.4 (dec.) |

TABLE 14-continued
| Ex. No. | Q | IR(KBr, $cm^{-1}$) | NMR(DMSO-$d_6$, ppm) | M.P. (°C.) |
|---|---|---|---|---|
| | $Q-SO_2NHCH_2CO_2H$ | | | |
| 80 | 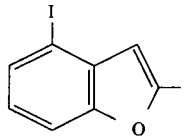 | 3265, 1717, 1362, 1248, 1159 | 3.83(2H, d, J=5.9Hz), 7.22~7.84(4H, m), 8.85(1H, t, J=5.9Hz), 12.66(1H, bs) | 222.9~227.1 |
| 81 | 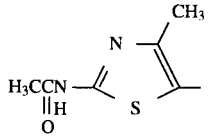 | 3290, 1707, 1560, 1338, 1167 | 2.16(3H, s), 2.43(3H, s), 3.65(2H, d, J=6.3Hz), 8.27(1H, t, J=6.3Hz), 12.45(1H, bs) | 247.0 (dec.) |
| 97 | 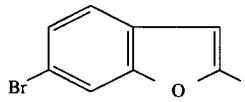 | 3312, 1719, 1353, 1249, 1165 | 3.77(2H, s), 7.49~7.79(3H, m), 8.04(1H, s), 8.79(1H, bs) | 186.5 |
| 98 | 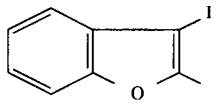 | 3230, 1709, 1368, 1238, 1173 | 3.82(2H, d, J=5.9Hz), 7.44~7.73(4H, m), 8.88(1H, t, J=5.9Hz) | 179.4~183.0 |
| 99 | 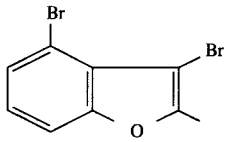 | 3280, 1716, 1369, 1238, 1168 | 3.85(2H, bs), 7.47(1H, dd, J=7.9, 7.6Hz), 7.68(1H, dd, J=7.6, 1.3Hz), 7.83(1H, dd, J=7.9, 1.3Hz), 9.00(1H, bs) | 222.9~227.1 |
| 100 | 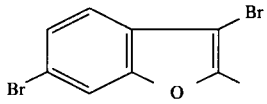 | 3338, 1731, 1365, 1234, 1166 | 3.83(2H, bs), 7.63(2H, s), 8.14(1H, s), 9.00(1H, bs) | 210.4~212.0 |
| 101 | 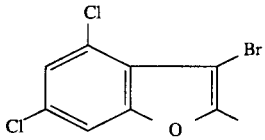 | 3238, 1717, 1369, 1171, 1151 | 3.86(2H, d, J=6.3Hz), 7.66(1H, d, J=1.7Hz), 8.07(1H, d, J=1.7Hz), 9.15(1H, t, J=6.3Hz) | 239.1~241.3 |
| 102 | 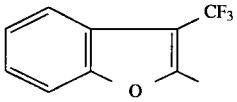 | 3247, 1716, 1373, 1239, 1173 | 3.89(2H, d, J=6.3Hz), 7.50~7.91(4H, m), 9.30(1H, t, J=6.3Hz) | 162.0~178.1 |
TABLE 15
| Ex. No. | Q | IR(KBr, $cm^{-1}$) | NMR(DMSO-$d_6$, ppm) | M.P. (°C.) |
|---|---|---|---|---|
| | $Q-SO_2NHCH_2CONH_2$ | | | |
| 82 | 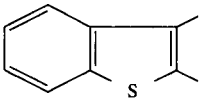 | 3434, 3308, 3188, 1703, 1366, 1155 | 2.46(3H, s), 3.67(2H, d, J=4.6Hz), 7.10(1H, bs), 7.30(1H, bs), 7.53~8.16(5H, m) | 180.4~181.1 |
| 83 | 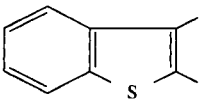 | 3392, 1672, 1522, 1354, 1333, 1153, 1139 | 3.60(2H, s), 4.10(3H, s), 7.05(1H, bs), 7.20(1H, bs), 7.53~8.16(5H, m) | 162.0~163.1 |

TABLE 16
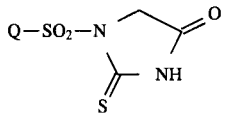
| Ex. No. | Q | IR(KBr, $cm^{-1}$) | NMR(DMSO-$d_6$, ppm) | M.P. (°C.) |
|---|---|---|---|---|
| 63 | 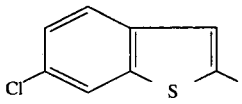 | 3320, 1800, 1769, 1458, 1370, 1230 | 4.74(2H, s), 7.58(1H, dd, J=8.6, 1.7Hz), 8.11(1H, d, J=8.6Hz), 8.36(1H, d, J=1.7Hz), 8.47(1H, s), 12.75(1H, bs) | 249.6 (dec.) |
| 64 | 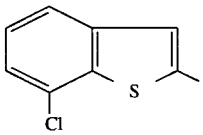 | 3110, 1791, 1751, 1745, 1381, 1180 | 4.76(2H, s), 7.50~7.82(1H, m), 8.11(1H, dd, J=7.6, 1.3Hz), 8.57(1H, s), 12.79(1H, bs) | 221.0 (dec.) |
| 65 | 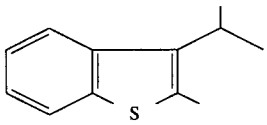 | 3140, 1791, 1757, 1459, 1346, 1177 | 1.43(6H, d, J=6.9Hz), 3.63~3.96(1H, m), 7.47~7.61(1H, m), 8.07~8.31(1H, m), 12.84(1H, bs) | 191.3~195.7 |
| 66 | 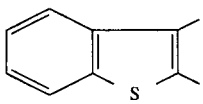 | 3120, 1756, 1465, 1366, 1175, 1164 | 4.76(2H, s), 7.60~8.38(4H, m), 13.01(1H, bs) | 232.1~233.5 |
| 67 | 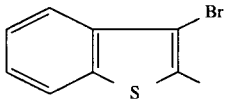 | 3180, 1782, 1755, 1455, 1372, 1170 | 4.95(2H, s), 7.56~8.32(4H, m), 12.92(1H, bs) | 222.8 (dec.) |
| 68 | 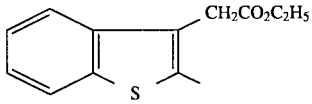 | 3220, 1756, 1726, 1376, 1173 | 1.14(3H, t, J=7.1Hz), 4.05(2H, q, J=7.1Hz), 4.41(2H, s), 4.77(2H, s), 7.55~7.72(2H, m), 8.02~8.20(2H, m), 12.81(1H, bs) | 204.7 (dec.) |
| 69 | 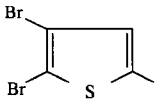 | 1793, 1473, 1392, 1191, 1174 | 4.69(2H, s), 8.07(1H, s), 12.78(1H, bs) | 203.0 (dec.) |
| 70 | 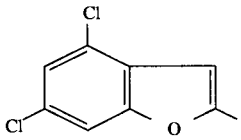 | 3292, 1795, 1765, 1464, 1381, 1185, 1176 | 4.74(2H, s), 7.73(1H, d, J=1.7Hz), 8.06~8.09(2H, m) 12.87(1H, bs) | 211.6 (dec.) |
| 71 | 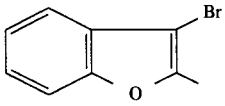 | 1795, 1759, 1460, 1384, 1149 | 4.83(2H, s), 7.43~7.89(4H, m), 12.96(1H, bs) | 212.8~219.9 (dec.) |
| 72 | 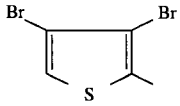 | 3350, 1793, 1764, 1458, 1362, 1174 | 4.87(2H, s), 8.44(1H, s), 12.88(1H, bs) | 242.0 (dec.) |

TABLE 16-continued
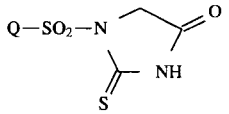
| Ex. No. | Q | IR(KBr, $cm^{-1}$) | NMR(DMSO-$d_6$, ppm) | M.P. (°C.) |
|---|---|---|---|---|
| 73 | 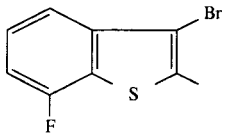 | 3289, 1795, 1770, 1492, 1458, 1359, 1180, 1156, 1085 | 4.97(2H, s), 7.55~7.88(3H, m), 13.01(1H, bs) | 254.0 (dec.) |
| 74 | 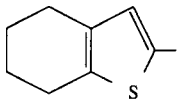 | 3157, 1794, 1765, 1376, 1352, 1161 | 1.50~1.94(4H, m), 2.46~2.94(4H, m), 4.65(2H, s), 7.72(1H, s), 12.61(1H, bs) | 245.0~246.8 |
| 75 | 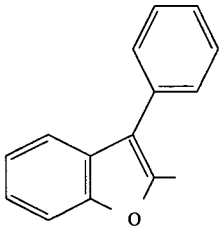 | 1786, 1750, 1446, 1370, 1348, 1178 | 4.37(2H, s), 7.13~7.90(9H, m), 12.82(1H, bs) | 183.8 (dec.) |
| 76 | 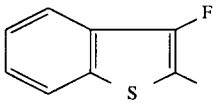 | 3130, 1790, 1759, 1383, 1182 | 4.73(2H, s), 7.57~8.15(4H, m), 12.81(1H, bs) | 230.5~223.8 |
| 77 | 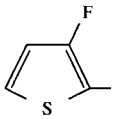 | 3107, 1755, 1537, 1469, 1423, 1376, 1248, 1173 | 4.66(2H, s), 7.21(1H, d, J=5.6Hz), 8.16(1H, dd, J=5.6, 4.3Hz). | 194.4 (dec.) |
| 78 | 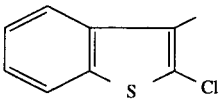 | 3268, 1790, 1765, 1459, 1348, 1178, 1160 | 4.93(2H, s), 7.50~7.73(2H, m), 8.04~8.29(2H, m), 12.82(1H, bs) | 244.0~246.0 |
| 79 | 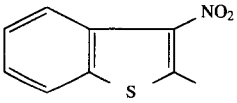 | 1790, 1763, 1460, 1348, 1182 | 4.68(2H, s), 7.59~7.70(2H, m), 8.14~8.40(2H, m), 12.68(1H, bs) | 710.0 (dec.) |
| 80 | 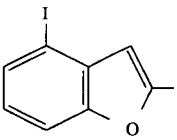 | 3215, 1744, 1456, 1332, 1162 | 4.77(2H, s), 7.30~7.91(4H, m), 12.85(1H, bs) | 210.9 (dec.) |
| 81 | 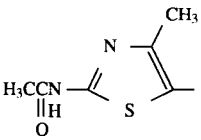 | 3180, 1761, 1535, 1371, 1170 | 2.19(3H, s), 2.54(3H, s), 4.68(2H, s), 12.64(1H, bs), 12.75(1H, bs) | 250.0 (dec.) |
| 97 | 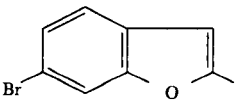 | 3319, 1794, 1766, 1461, 1163 | 4.73(2H, s), 7.63(1H, d, J=8.6Hz), 7.85(1H, d, J=8.6Hz), 8.05(1H, s), 8.12(1H, s) | 246.8~247.7 |

TABLE 16-continued

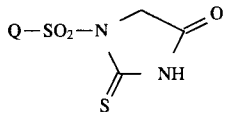

| Ex. No. | Q | IR(KBr, $cm^{-1}$) | NMR(DMSO-$d_6$, ppm) | M.P. (°C.) |
|---|---|---|---|---|
| 98 | 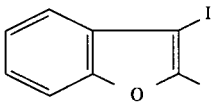 | 1735, 1397, 1228, 1173 | 4.88(2H, s), 7.56~7.90(4H, m), 13.04(1H, bs) | 195~198 |
| 99 | 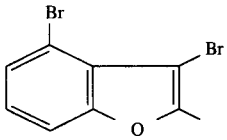 | 3330, 1792, 1764, 1456, 1174 | 4.86(2H, s), 7.57(1H, t, J=7.9Hz), 7.75(1H, dd, J=7.9, 1.3Hz), 7.93(1H, dd, J=7.9, 1.3Hz), 13.08(1H, bs) | 219.5~222.3 |
| 100 | 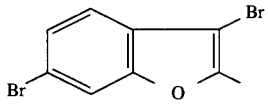 | 3084, 1749, 1388, 1266, 1182 | 4.81(2H, s), 7.70(1H, s), 7.72(1H, s), 8.22(1H, s) | >240 (dec.) |
| 101 | 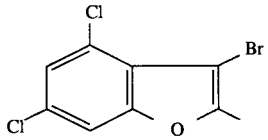 | 3568, 1752, 1382, 1244, 1177 | 4.84(2H, s), 7.76(1H, d, J=1.6Hz), 8.17(1H, d, J=1.6Hz), 13.15(1H, bs) | 220 (dec.) |
| 102 | 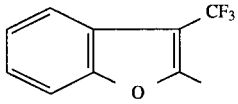 | 3110, 1752, 1239, 1178, 1174 | 4.83(2H, s), 7.60~7.99(4H, m) | 161.6~179.3 |

Formulation F (Capsules)

Compound 38, 250 g of weight, 730 g of lactose and 20 g of magnesium stearate were weighed and mixed until the mixture became homogeneous. The mixture was then filled in No. 1 hard gelatin capsule at 200 mg each to obtain capsule preparation.

Formulation G (Tables)

Compound 34, 300 g of weight, 550 g of lactose, 120 g of potato starch, 15 of polyvinyl alcohol and 15 g of magnesium stearate were weighed. The weighed amount of compound 34, lactose and potato starch were mixed until accomplishing homogeneity. Then aqueous solution of polyvinylalcohol was added to the mixture and granulated by wet process. The granules were then dried, mixed with magnesium stearate and pressed into tablets, each weighing 200 mg.

Formulation H (Powder)

Compound 46, 200 g of weight, 790 g of lactose and 10 g of magnesium stearate were weighed and mixed until the mixture became homogeneous to obtain 20% powder preparation.

Formulation I (Suppositories)

Compound 44, 100 g or weight were weighed and ground by a mortar until the compound became fine powder. Then 180 g of polyethylene glycol 1500 and 720 g of polyethylene glycol 4000 were added to the compound and melted. The mixture was then pressed at 1 g each to obtain suppository preparation.

What is claimed is:

1. A sulfonylglycine derivative represented by the formula (IV):

$$Q—SO_7NHCH_7CO—R \quad (IV)$$

wherein R represents a hydroxy group, an alkoxy group or an amino group which may be substituted with an alkoxycarbonyl group, Q represents a benzo[b]furan-2-yl group which may be substituted by one or more substituents which are the same or different and selected from the group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group other than a lower alkoxy group, an optionally protected amino group, a carbamoyl group and a phenyl group.

2. A sulfonylglycine derivative as claimed in claim 1, wherein said substituents are 1 to 3 halogen atoms.

[3. A sulfonylglycine derivative represented by the formula (IV):

$$Q—SO_2NHCH_2CO—R \quad (IV)$$

where R represents a hydroxy group, an alkoxy group or an amino group which may be substituted with an alkoxycarbonyl group, Q represents a thiazolyl group which may be substituted by one or more substituents which are the same or different and selected from the group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsufonyl group, an optionally protected hydroxy group other than a lower alkoxy group, an optionally protected amino group, and a carbamoyl group.]

[4. A sulfonylglycine derivative as claimed in claim 1 wherein Q represents a pyridyl group which may be substituted.]

5. A sulfonylglycine derivative as claimed in claim [1] *18* wherein Q represents an indolyl group which may be substituted.

6. A sulfonylglycine derivative as claimed in claim [1] *18* wherein Q represents a benzothiazolyl group which may be substituted.

7. A sulfonylglycine derivative as claimed in claim [1] *18* wherein Q represents a benzisothiazolyl group which may be substituted.

8. A sulfonylglycine derivative as claimed in claim [1] *18* wherein Q represents a coumarinyl group which may be substituted.

9. A sulfonylglycine derivative as claimed in claim [1] *18* wherein Q represents a chromonyl group which may be substituted.

10. A sulfonylglycine derivative as claimed in claim [1] *18* wherein Q represents a benzimidazolyl group which may be substituted.

11. A sulfonylglycine derivative as claimed in claim [1] *18* wherein Q represents a benzotriazolyl group which may be substituted.

12. A sulfonylglycine derivative as claimed in claim [1] *18* wherein Q represents a benzisoxazolyl group which may be substituted.

[13. A sulfonylglycine derivative represented by the formula (IV):

$$Q—SO_2NHCH_2CO—R \qquad (IV)$$

wherein

R represents a hydroxy group, an alkoxy group or an amino group which may be substituted with an alkoxycarbonyl group, Q represents a furyl group, a pyridyl group, an indolyl group, a benzothiazolyl group, a benzisothiazolyl group, a benzothienyl group, a coumarinyl group, a chromonyl group, a benzimidazolyl group, a benzotriazolyl group or a benzisoxazolyl group any one of which may be substituted by one or more substituents which are the same or different and selected from a group consisting of a halogen atom, a lower alkyl group, a nitro group, a cyano group, an optionally protected carboxy group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group other than a lower alkoxy group, an optionally protected amino group, a carbamoyl group and a phenyl group, or Q represents a benzo[b]furan-2-yl group which may be substituted by one or more substituents which are the same or different and are selected from the group consisting of a halogen atom, a cyano group, an optionally protected carboxymethyl group, a halogenated lower alkyl group, a lower alkylthio group, a lower alkylsulfinyl group, a lower alkylsulfonyl group, a carbamoyl group and a phenyl group.]

14. A sulfonylglycine derivative as claimed in claim [13] *18*, wherein Q represents a furyl group, a benzothienyl group or a benzo[b]furan-2-yl group.

15. A sulfonylglycine derivative as claimed in claim 14, wherein Q represents a benzo[b]thien-2-yl group which may b substituted.

16. A sulfonylglycine derivative as claimed in claim 14, wherein Q represents a benzo[b]furan-2-yl group which may b substituted.

17. A sulfonylglycine derivative as claimed in claim 16, wherein the said substituents are 1 to 3 halogen atoms.

*18. A sulfonylglycine derivative represented by the formula (IV):*

$$Q—SO_2NHCH_2CO—R \qquad (IV)$$

*where R represents a hydroxy group, an alkoxy group or an amino group which may be substituted with an alkoxycarbonyl group, Q represents a furyl group, an indolyl group, a benzothiazolyl group, a benzisothiazolyl group, a benzothienyl group, a coumarinyl group, a chromonyl group, a benzimidazolyl group, a benzotriazolyl group or a benzisoxazolyl group any one of which may be substituted by one or more substituents which are the same or different and are selected from the group consisting of a halogen atom, a lower alkyl group, a nitro group, a cyano group, an optionally protected carboxymethyl group, a halogenated lower alkyl group, a lower alkylthio group, a lower alkylcarbonyl group, a lower alkoxy group, a lower alkylsulfinyl group, a lower alkylsulfonyl group, an optionally protected hydroxy group other than a lower alkoxy group, an optionally protected amino group, a carbamoyl group, and a phenyl group, or Q represents a benzo[b]furan-2-yl group which may be substituted by one or more substituents which are the same or different and are selected from the group consisting of a halogen atom, a cyano group, an optionally protected carboxymethyl group, a halogenated lower alkyl group, a lower alkylthio group, a lower alkylsulfinyl group, a lower alkylsulfonyl group, a carbamoyl group and a phenyl group.*

* * * * *

UNITED STATES PATENT AND TRADEMARK OFFICE

CERTIFICATE OF CORRECTION

PATENT NO. : Re. 35,279

DATED : June 18, 1996

INVENTOR(S) : Ei MOCHIDA, Kimihiro MURAKAMI, Kazuo KATO, Katsuaki KATO, Jun OKUDA and Ichitomo MIWA

It is certified that error appears in the above-identified patent and that said Letters Patent is hereby corrected as shown below:

Please correct in Column 92, line 45, change "Q-$SO_7NHCH_7CO$-R (IV)" to

--Q-$SO_2NHCH_2CO$-R (IV)--.

Please correct in Column 94, line 22, change "b" to --be--; and line 25, change "b" to --be--.

Signed and Sealed this

Twenty-first Day of January, 1997

*Attest:*

*Attesting Officer*

BRUCE LEHMAN

*Commissioner of Patents and Trademarks*